(12) United States Patent
Niesman et al.

(10) Patent No.: US 9,980,965 B2
(45) Date of Patent: May 29, 2018

(54) TREATMENT OF AUTOIMMUNE DISEASE

(71) Applicant: MingSight Pharmaceuticals, Inc., San Diego, CA (US)

(72) Inventors: Michael Niesman, San Diego, CA (US); Kai Zhang, San Diego, CA (US)

(73) Assignee: MINGSIGHT PHARMACEUTICALS, INC., San Diego, CA (US)

( * ) Notice: Subject to any disclaimer, the term of this patent is extended or adjusted under 35 U.S.C. 154(b) by 0 days. days.

(21) Appl. No.: 15/788,678

(22) Filed: Oct. 19, 2017

(65) Prior Publication Data
US 2018/0098988 A1 Apr. 12, 2018

Related U.S. Application Data

(63) Continuation of application No. 15/313,031, filed as application No. PCT/US2015/032315 on May 22, 2015, now Pat. No. 9,814,716.

(60) Provisional application No. 62/002,724, filed on May 23, 2014.

(51) Int. Cl.
*A61K 31/506* (2006.01)

(52) U.S. Cl.
CPC .................. *A61K 31/506* (2013.01)

(58) Field of Classification Search
None
See application file for complete search history.

(56) References Cited

U.S. PATENT DOCUMENTS

| | | | |
|---|---|---|---|
| 8,114,871 B2 | 2/2012 | Botrous et al. | |
| 8,183,255 B2 | 5/2012 | Li et al. | |
| 8,877,761 B2 | 11/2014 | Li et al. | |
| 8,999,981 B2 | 4/2015 | Botrous et al. | |
| 9,518,060 B2 | 12/2016 | Li et al. | |
| 2010/0292231 A1 | 11/2010 | Ajami et al. | |
| 2017/0196865 A1 | 7/2017 | Niesman et al. | |

FOREIGN PATENT DOCUMENTS

| | | |
|---|---|---|
| CN | 1726217 A | 1/2006 |
| CN | 101641338 A | 2/2010 |
| CN | 101646673 A | 2/2010 |
| CN | 101675052 A | 3/2010 |
| CN | 102060857 A | 5/2011 |
| WO | WO-2008037266 A1 | 4/2008 |
| WO | WO-2008096260 A1 | 8/2008 |
| WO | WO-2008125945 A2 | 10/2008 |
| WO | WO-2010043561 A2 | 4/2010 |
| WO | WO-2015179847 A1 | 11/2015 |

OTHER PUBLICATIONS

Cohen et al. Lpr and gld: single gene models of systemic autoimmunity and lymphoproliferative disease. Annu Rev Immunol 9:243-269 (1991).
Das Evcimen et al. The role of protein kinase C activation and the vascular complications of diabetes. Pharmacol Res 55(6):498-510 (2007).
Grant et al. Discovery of a novel class of targeted kinase inhibitors that blocks protein kinase C signaling and ameliorates retinal vascular leakage in a diabetic rat model. Eur J Pharmacol 627(1-3):16-25 (2010).
Gruber et al. PKCθ cooperates with PKCα in alloimmune responses of T cells in vivo. Mol Immunol 46:2071-2079 (2009).
Hashim et al. Biological activity of region 65-102 of the myelin basic protein. J Neurosci Res 16(3):467-478 (1986).
Honigberg et al. The Bruton tyrosine kinase inhibitor PCI-32765 blocks B-cell activation and is efficacious in models of autoimmune disease and B-cell malignancy. PNAS USA 107:13075-13080 (2010).
Leitges et al. Immunodeficiency in protein kinase Cβ-deficient mice. Science 273:788-791 (1996).
Li et al. Identification of novel pyrrolopyrazoles as protein kinase C β II inhibitors. Bioorg Med Chem Lett. 21(1):584-587 (2011).
Marsland et al. T-cell fate and function: PKC-θ and beyond. Trends Immunol 29(4):179-185 (2008).
Mecklenbrauker et al. Protein kinase Cσ controls self-antigen-induced B-cell tolerance. Nature 416:860-865 (2002).
Miyamoto et al. Increased proliferation of B cells and auto-immunity in mice lacking protein kinase Cσ. Nature 416:865-869 (2002).
Mochizuki et al. Effects of cyclosporine and other immunosuppressive drugs on experimental autoimmune uveoretinitis in rats. Invest Ophthalmol Vis Sci 26(2):226-232 (1985).
Murphy et al. Systemic lupus erythematosus and other autoimmune rheumatic diseases: challenges to treatment. Lancet 382:809-818 (2013).
Newton. Protein kinase C: structural and spatial regulation by phosphorylation, cofactors, and macromolecular interactions. Chem Rev 101:2353-2364 (2001).
Nussenblatt et al. Cyclosporin a. Inhibition of experimental autoimmune uveitis in Lewis rats. J Clin Invest. 67(4):1228-1231 (1981).
Oleksyn et al. PKCβ is required for lupus development in Sle mice. Arthritis Rheum 65:1022-1031 (2013).
Patani et al. Bioisosterism: A Rational Approach in Drug Design. Chemical Reviews 96:3147-3176 (1996).
PCT/US2015/032315 International Preliminary Report on Patentability dated Dec. 8, 2016.
PCT/US2015/032315 International Search Report and Written Opinion dated Aug. 5, 2015.
Pfeifhofer et al. Defective IgG2a/2b class switching in PKC alpha-/- mice. J Immunol 176:6004-6011 (2006).
Saijo et al. Protein kinase C β controls nuclear factor κB activation in B cells through selective regulation of the IκB kinase α. J Exp Med 195:1647-1652 (2002).
Shlomchik et al. The role of B cells in lpr/lpr-induced autoimmunity. J Exp Med 180:1295-1306 (1994).
Su et al. PKC-β controls IκB kinase lipid raft recruitment and activation in response to BCR signaling. Nat Immunol 3:780-786 (2002).

(Continued)

*Primary Examiner* — Heidi Reese
(74) *Attorney, Agent, or Firm* — Wilson, Sonsini, Goodrich & Rosati

(57) ABSTRACT

Provided herein are compositions and methods for the treatment of autoimmune diseases, including lupus, uveitis and encephalitis. Said compositions useful for treating autoimmune diseases comprise pyrrolo-pyrazole PKC inhibitors.

13 Claims, 7 Drawing Sheets

(56) References Cited

OTHER PUBLICATIONS

Sun. Intervention of PKC-θ as an immunosuppressive regimen. Front Immunol 3:225 (2012).

Von Essen et al. Protein kinase C (PKC)α and PKCθ are the major PKC isotypes involved in TCR down-regulation. J Immunol 176:7502-7510 (2006).

Wahren-Herlenius et al. Immunopathogenic mechanisms of systemic autoimmune disease. Lancet 382:819-831 (2013).

TREATMENT OF AUTOIMMUNE DISEASE

CROSS REFERENCE

This is continuation application of U.S. application Ser. No. 15/313,031, filed Nov. 21, 2016, which is a national stage application of PCT/US2015/032315, filed May 22, 2015, which claims the benefit of U.S. Provisional Application No. 62/002,724, filed May 23, 2014, all of which are incorporated by reference herein in their entirety.

BACKGROUND

A need exists in the medical art for compounds and methods for the treatment of Lupus and other autoimmune mediated diseases.

BRIEF SUMMARY OF THE INVENTION

Provided herein are compositions and methods for the treatment of autoimmune diseases, including lupus, uveitis and encephalitis. Said compositions useful for treating autoimmune diseases comprise pyrrolo-pyrazole PKC inhibitors.

One embodiment provides a method of treating lupus erythematosus in a subject in need thereof comprising administering to the subject a composition comprising a compound having the formula 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof, and a pharmaceutically acceptable excipient.

One embodiment provides a method of treating uveitis in a subject in need thereof comprising administering to the subject a composition comprising a compound having the formula 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof, and a pharmaceutically acceptable excipient.

One embodiment provides a method of treating encephalitis in a subject in need thereof comprising administering to the subject a composition comprising a compound having the formula 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof, and a pharmaceutically acceptable excipient.

INCORPORATION BY REFERENCE

Figure 1:
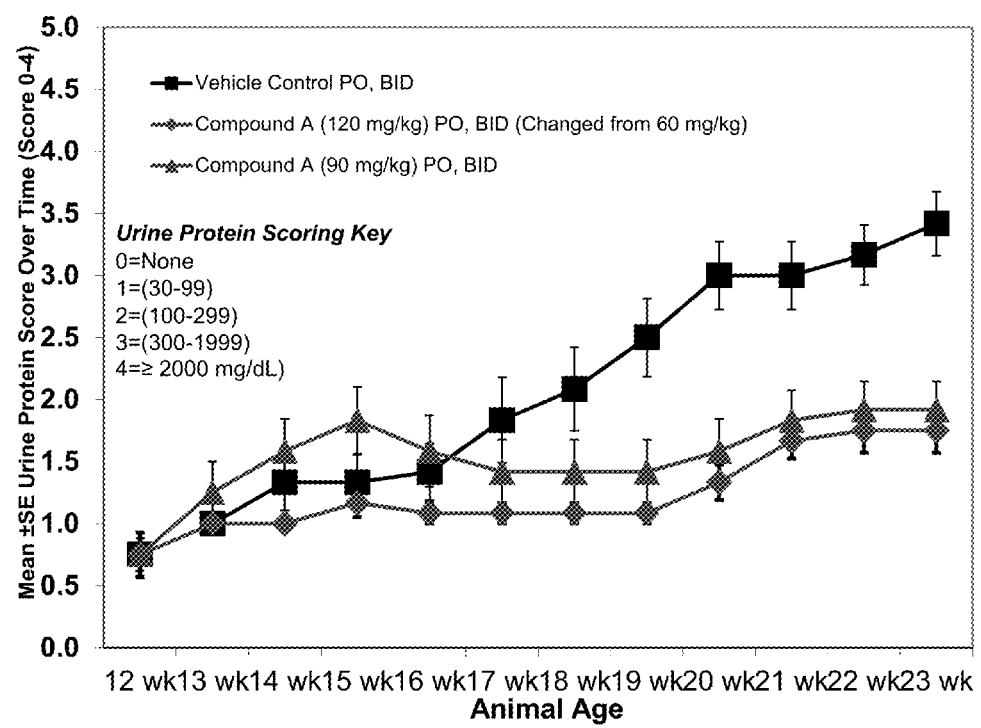
FIG. 1 illustrates efficacy of compound A in reducing urine score in a MRL/lpr lupus model.

All publications, patents, and patent applications mentioned in this specification are herein incorporated by reference for the specific purposes identified herein.

DETAILED DESCRIPTION OF THE INVENTION

Certain Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. Hence "about 5 µg" means "about 5 µg" and also "5 µg." Generally, the term "about" includes an amount that would be expected to be within experimental error.

As used herein, the terms "comprising" and "including" are used in their open, non-limiting sense. As used herein, the terms "$C_1$-$C_8$" or "$C_2$-$C_8$" and so forth, refer to moieties having 1 to 8 or 2 to 8 carbon atoms, respectively.

The term "alkyl", as used herein, unless otherwise indicated, includes saturated monovalent hydrocarbon radicals having straight or branched moieties. Exemplary alkyl moieties have carbon atoms in the range of 1 to 8 carbon atoms, 1 to 6 carbon atoms or 1 to 4 carbon atoms.

The term "alkenyl", as used herein, unless otherwise indicated, includes alkyl moieties having at least one carbon-carbon double bond wherein alkyl is as defined above and including E and Z isomers of said alkenyl moiety.

The term "alkynyl", as used herein, unless otherwise indicated, includes alkyl moieties having at least one carbon-carbon triple bond wherein alkyl is as defined above.

The term "alkoxyl", as used herein, unless otherwise indicated, includes O-alkyl groups wherein alkyl is as defined above.

The term "hydroxyl", as used herein, unless otherwise indicated, includes —OH.

The term "amino", as used herein, unless otherwise indicated, is intended to include the —NH2 radical, and any substitutions of the N atom.

The terms "halogen" and "halo", as used herein, unless otherwise indicated, represent chlorine, fluorine, bromine or iodine.

The term "trifluoromethyl", as used herein, unless otherwise indicated, is meant to represent a —$CF_3$ group.

The term "perfluoroalkyl", as used herein, is meant to represent an alkyl group in which all hydrogens attached to the carbons have been replaced by fluorine, such as $CF_3$, $CF_2$—$CF_3$, $C(CF_2)(CF_2)$ and so on.

The term "trifluoromethoxy", as used herein, unless otherwise indicated, is meant to represent a —$OCF_3$ group.

The term "cyano", as used herein, unless otherwise indicated, is meant to represent a —CN group.

The term "CH$_2$Cl$_2$", as used herein, unless otherwise indicated, is meant to represent dichloromethane.

The term "C$_3$-C$_{12}$ cycloalkyl" or "C$_5$-C$_8$ cycloalkyl", as used herein, unless otherwise indicated, refers to a non-aromatic, saturated or partially saturated, monocyclic or fused, spiro or unfused bicyclic or tricyclic hydrocarbon referred to herein containing a total of from 3 to 12 carbon atoms, or 5-8 ring carbon atoms, respectively. Exemplary cycloalkyls include rings having from 3-10 carbon atoms, such as cyclopropyl, cyclobutyl, cyclopentyl, cyclohexyl, cycloheptyl, and adamantyl. Illustrative examples of cycloalkyl are derived from, but not limited to, the following:

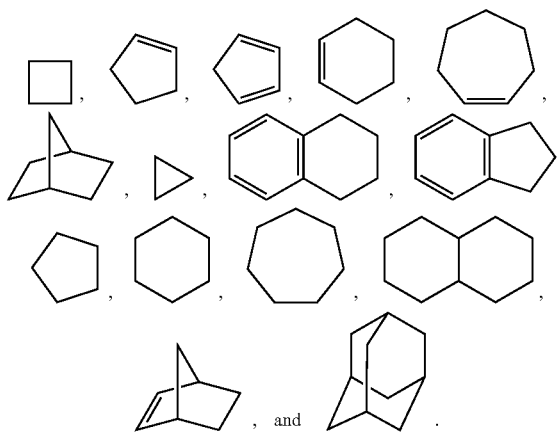

The term "aryl", as used herein, unless otherwise indicated, includes an organic radical derived from an aromatic hydrocarbon by removal of one hydrogen, such as phenyl or naphthyl.

The term "(3-15)-membered heterocycyl", "(3-7)-membered heterocyclyl", "(6-10)-membered heterocyclyl", or "(4 to 10)-membered heterocyclyl", as used herein, unless otherwise indicated, includes aromatic and non-aromatic heterocyclic groups containing one to four heteroatoms each selected from O, S and N, wherein each heterocyclic group has from 3-15, 3-7, 6-10, or 4 to 10 atoms, respectively, in its ring system, and with the proviso that the ring of said group does not contain two adjacent O or S atoms. Non-aromatic heterocyclic groups include groups having only 3 atoms in their ring system, but aromatic heterocyclic groups must have at least 5 atoms in their ring system. The heterocyclic groups include benzo-fused ring systems. An example of a 3 membered heterocyclic group is aziridine, an example of a 4 membered heterocyclic group is azetidinyl (derived from azetidine). An example of a 5 membered heterocyclic group is thiazolyl, an example of a 7 membered ring is azepinyl, and an example of a 10 membered heterocyclic group is quinolinyl. Examples of non-aromatic heterocyclic groups are pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Heterocycles include monocyclic and polycyclic aromatic ring structures, with "(5-12)-membered heteroaryls" referring to those that are heterocycles having 5 to 12 atoms in their ring system(s). Examples of "(5-12)-membered heteroaryls" are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the groups listed above, may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). The above-mentioned heterocyclic groups may be optionally substituted on any ring carbon, sulfur, or nitrogen atom(s) by one to two oxo, per ring. An example of a heterocyclic group wherein 2 ring carbon atoms are substituted with oxo moieties is 1,1-dioxo-thiomorpholinyl. Other Illustrative examples of 4 to 10 membered heterocyclic are derived from, but not limited to, the following:

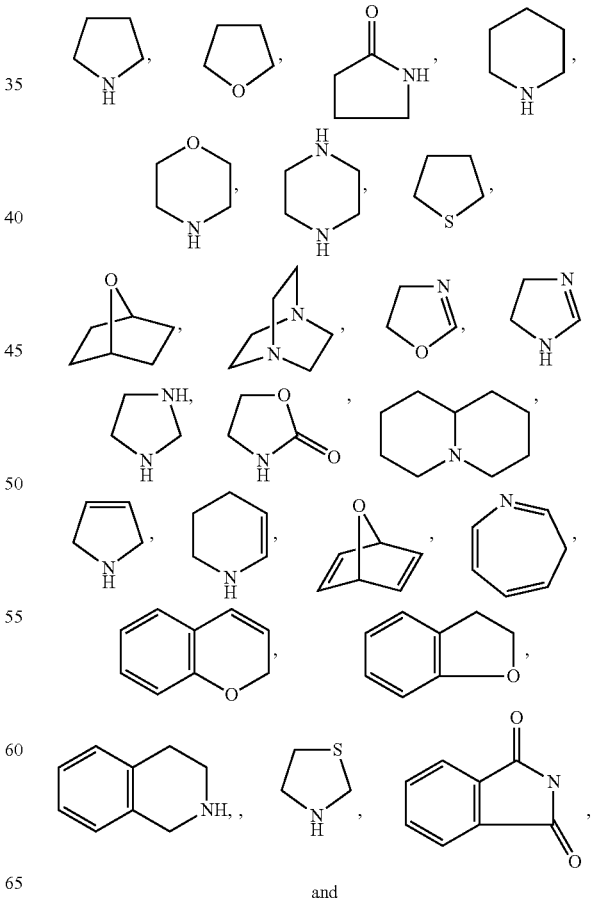

and

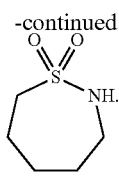

The term "(12-15)-membered heterocyclyl", as used herein, unless otherwise indicated, includes aromatic and non-aromatic heterocyclic groups that are in a partially fused or spirocyclic configuration and which contain at least one N and optionally additional 1 to 5 heteroatoms each selected from O, S and N, wherein the heterocyclic group has from 12 to 15 atoms, respectively, in its system, and with the proviso that any ring of said group does not contain two adjacent O or S atoms. The heterocyclic groups include tricyclic fused ring and spirocyclic systems. An example of a 13-membered tricyclic heterocyclic group is 3,4-dihydropyrazino[1,2-a]benzimidazole and an example of a 15-membered spirocyclic heterocyclic group is 3,4-dihydro-1'H-spirochromene.

Unless otherwise indicated, the term "oxo" refers to =O.

A "solvate" is intended to mean a pharmaceutically acceptable solvate form of a specified compound that retains the biological effectiveness of such compound. Examples of solvates include compounds of the invention in combination with water, isopropanol, ethanol, methanol, DMSO (dimethylsulfoxide), ethyl acetate, acetic acid, or ethanolamine.

The phrase "pharmaceutically acceptable salt(s)", as used herein, unless otherwise indicated, includes salts of acidic or basic groups which may be present in the compounds of formula (A) or formula (B). The compounds of formula (A) or formula (B) that are basic in nature are capable of forming a wide variety of salts with various inorganic and organic acids. The acids that may be used to prepare pharmaceutically acceptable acid addition salts of such basic compounds of formula (A) or formula (B) are those that form non-toxic acid addition salts, i.e., salts containing pharmacologically acceptable anions, such as the acetate, benzenesulfonate, benzoate, bicarbonate, bisulfate, bitartrate, borate, bromide, calcium edetate, camsylate, carbonate, chloride, clavulanate, citrate, dihydrochloride, edetate, edislyate, estolate, esylate, ethylsuccinate, fumarate, gluceptate, gluconate, glutamate, glycollylarsanilate, hexylresorcinate, hydrabamine, hydrobromide, hydrochloride, iodide, isothionate, lactate, lactobionate, laurate, malate, maleate, mandelate, mesylate, methylsulfate, mucate, napsylate, nitrate, oleate, oxalate, pamoate (embonate), palmitate, pantothenate, phospate/diphosphate, polygalacturonate, salicylate, stearate, subacetate, succinate, tannate, tartrate, teoclate, tosylate, triethiodode, and valerate salts.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as "treating" is defined immediately above.

The phrase "therapeutically effective amount", as used herein, refers to that amount of drug or pharmaceutical agent that will elicit the biological or medical response of a tissue, system, animal, or human that is being sought by a researcher, veterinarian, medical doctor or other.

The term "substituted" means that the specified group or moiety bears one or more substituents. The term "unsubstituted" means that the specified group bears no substituents.

The term "optionally substituted" means that the specified group is unsubstituted or substituted by one or more substituents.

In accordance with convention, in some structural formula herein, the carbon atoms and their bound hydrogen atoms are not explicitly depicted e.g.,  represents a methyl group, represents an ethyl group,

represents a cyclopentyl group, etc. Moreover, the depiction of any cyclic group (aryl, heterocyclic or cycloalkyl) with a bond that is not directly attached to a ring atom, e.g., indicates that the point of attachment may be on any available ring atom of the cyclic group.

Certain compounds of formula (A) or formula (B) may have asymmetric centers and therefore exist in different enantiomeric forms. All optical isomers and stereoisomers of the compounds of formula (A) or formula (B), and mixtures thereof, are considered to be within the scope of the invention. With respect to the compounds of formula (A) or formula (B), the invention includes the use of a racemate, one or more enantiomeric forms, one or more diastereomeric forms, or mixtures thereof. The compounds of formula (A) or formula (B) may also exist as tautomers. This invention relates to the use of all such tautomers and mixtures thereof.

Certain functional groups contained within the compounds of the present invention can be substituted for bioisosteric groups, that is, groups which have similar spatial or electronic requirements to the parent group, but exhibit differing or improved physicochemical or other properties. Suitable examples are well known to those of skill in the art, and include, but are not limited to moieties described in Patini et al., Chem. Rev, 1996, 96, 3147-3176 and references cited therein.

The subject invention also includes isotopically-labelled compounds, which are identical to those recited in formula (A) or formula (B), but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$ $^{18}O$, $^{17}O$, $^{31}P$, $^{32}P$, $^{35}S$, $^{18}F$, and $^{36}Cl$, respectively. Compounds of the present invention and pharmaceutically acceptable salts or solvates of said compounds which contain the aforementioned isotopes and/or other isotopes of other atoms are within the scope of this invention. Certain isotopically-labelled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of formula (A) or formula (B) of this invention thereof can generally be prepared by carrying out the procedures disclosed in the Schemes and/or in the Examples below, by substituting a readily available isotopically labeled reagent for a non-isotopically labeled reagent.

The term "mmol", as used herein, unless otherwise indicated, is intended to mean millimole. The term "equiv", as used herein, unless otherwise indicated, is intended to mean equivalent. The term "mL", as used herein, unless otherwise indicated, is intended to mean milliliter. The term "U", as used herein, unless otherwise indicated, is intended to mean units. The term "mm" as used herein, unless otherwise indicated, is intended to mean millimeter. The term "g", as used herein, unless otherwise indicated, is intended to mean gram. The term "kg", as used herein, unless otherwise indicated, is intended to mean kilogram. The term "h", as used herein, unless otherwise indicated, is intended to mean hour. The term "min", as used herein, unless otherwise indicated, is intended to mean minute. The term "μL", as used herein, unless otherwise indicated, is intended to mean microliter. The term "μM", as used herein, unless otherwise indicated, is intended to mean micromolar. The term "μm", as used herein, unless otherwise indicated, is intended to mean micrometer. The term "M", as used herein, unless otherwise indicated, is intended to mean molar. The term "N", as used herein, unless otherwise indicated, is intended to mean normal. The term "nm", as used herein, unless otherwise indicated, is intended to mean nanometer. The term "nM", as used herein, unless otherwise indicated, is intended to mean nanoMolar. The term "amu", as used herein, unless otherwise indicated, is intended to mean atomic mass unit. The term "° C.", as used herein, unless otherwise indicated, is intended to mean Celsius. The term "m/z", as used herein, unless otherwise indicated, is intended to mean, mass/charge ratio. The term "wt/wt", as used herein, unless otherwise indicated, is intended to mean weight/weight. The term "v/v", as used herein, unless otherwise indicated, is intended to mean volume/volume. The term "mL/min", as used herein, unless otherwise indicated, is intended to mean milliliter/minute. The term "UV", as used herein, unless otherwise indicated, is intended to mean ultraviolet. The term "APCI-MS", as used herein, unless otherwise indicated, is intended to mean atmospheric pressure chemical ionization mass spectroscopy. The term "HPLC", as used herein, unless otherwise indicated, is intended to mean high performance liquid chromatograph. The chromatography was performed at a temperature of about 20° C., unless otherwise indicated. The term "LC", as used herein, unless otherwise indicated, is intended to mean liquid chromatograph. The term "LCMS", as used herein, unless otherwise indicated, is intended to mean liquid chromatography mass spectroscopy. The term "TLC", as used herein, unless otherwise indicated, is intended to mean thin layer chromatography. The term "SFC", as used herein, unless otherwise indicated, is intended to mean supercritical fluid chromatography. The term "sat" as used herein, unless otherwise indicated, is intended to mean saturated. The term "aq" as used herein, is intended to mean aqueous. The term "ELSD" as used herein, unless otherwise indicated, is intended to mean evaporative light scattering detection. The term "MS", as used herein, unless otherwise indicated, is intended to mean mass spectroscopy. The term "HRMS (ESI)", as used herein, unless otherwise indicated, is intended to mean high-resolution mass spectrometry (electrospray ionization). The term "Anal.", as used herein, unless otherwise indicated, is intended to mean analytical. The term "Calcd", as used herein, unless otherwise indicated, is intended to mean calculated. The term "N/A", as used herein, unless otherwise indicated, is intended to mean not tested. The term "RT", as used herein, unless otherwise indicated, is intended to mean room temperature. The term "Mth.", as used herein, unless otherwise indicated, is intended to mean Method. The term "Celite®", as used herein, unless otherwise indicated, is intended to mean a white solid diatomite filter agent commercially available from World Minerals located in Los Angeles, Calif. USA. The term "Eg.", as used herein, unless otherwise indicated, is intended to mean example.

Terms such as —$(CR^3R^4)_t$ or —$(CR^{10}R^{11})_v$, for example, are used, $R^3$, $R^4$, $R^{10}$ and $R^{11}$ may vary with each iteration of t or v above 1. For instance, where t or v is 2 the terms-$(CR^3R^4)$ or —$(CR^{10}R^{11})_t$ may equal-$CH_2CH_2$—, or —$CH(CH_3)C(CH_2CH_3)(CH_2CH_2CH_3)$—, or any number of similar moieties falling within the scope of the definitions of $R^3$, $R^4$, $R^{10}$ and $R^{11}$.

The term "$K_i$", as used herein, unless otherwise indicated, is intended to mean values of enzyme inhibition constant. The term "$K_i$ app", as used herein, unless otherwise indicated, is intended to mean $K_i$ apparent. The term "$IC_{50}$", as used herein, unless otherwise indicated, is intended to mean concentrations required for at least 50% enzyme inhibition.

Other aspects, advantages, and features of the invention will become apparent from the detailed description below.

Protein Kinase C

The superfamily of kinases known as protein kinase C (PKC) are important kinases that are active in and that act as regulators in many cell signaling pathways. (Newton, 2001, Chem. Rev. 101, 2353-2364). Specific isoforms of PKC have been implicated in the response to hyperglycemia (e.g., PKCβ (beta) Das Evcimen and King, 2007, Pharmacol Res., 55(6): p. 498-510) and in T and B cell survival and function (e.g., PKCθ (theta): Sun, Z. 2012, Front Immunol 3, 225; PKCβ: Leitges, M. et al., 1996, Science 273, 788-791; PKCα (alpha): Gruber, T. et al., 2009, Mol Immunol 46, 2071-2079).

Both T lymphocytes and B lymphocytes (T cells and B cells) have been shown to contribute to autoimmune disease, often simultaneously (Wahren-Herlenius and Dörner T. 2013, Lancet. 382:819-31). Recent scientific reports have revealed that specific isoforms of PKC are crucial to the normal function of T and B cells and in their contribution to autoimmune disease.

Three isoforms, PKCθ, PKCα and PKCβ, appear to be most important for lymphocyte function. PKCθ is critical to T-cell function (Sun, 2012, Front Immunol 3, 225). Specifically, PKCθ is downstream of the T cell receptor complex and plays a critical role in T cell survival, function and autoimmune stimulation. Mouse models of autoimmune diseases have been used to illustrate PKCθ function in T cell-dependent autoimmunity (Marsland, B. J. and Kopf, M., 2008, Trends Immunol, 29(4) 179-85). PKCα plays a non-redundant role in T cell activation (Gruber, T., et al, 2009, Mol Immunol 46, 2071-2079; Pfeifhofer, C., et al, 2006, J Immunol 176, 6004-6011; von Essen, M., et al, 2006, J Immunol 176, 7502-75). And PKCβ plays a key role in B cell survival, function, and the dysfunction seen in autoimmunity (Leitges, M., et al, 1996, Science 273, 788-791; Saijo, K., et al, 2002, J Exp Med 195, 1647-1652; Su, T. T., et al., 2002, Nat Immunol 3, 780-786). Finally, it has been shown in mice that inhibition of PKCδ (delta) appears to have the potential to induce autoimmune disease in B cells. PKCδ knockout mice (PKCδ$^{-/-}$) have increased antibody production including auto-antibodies and actually display autoimmune phenotypes. (Mecklenbrauker, I., et al, 2002, Nature 416, 860-865; Miyamoto, A., et al., 2002, Nature 416, 865-869).

Pyrrolo-Pyrazole PKC Inhibitors

The pyrrolo-pyrazole PKC inhibitors used herein have been previously described in WO 2008/096260 and WO 2008/125945 and related patents and patent applications, e.g. U.S. Pat. No. 8,183,255, U.S. Pat. No. 8,877,761, U.S. patent application Ser. No. 14/506,470, U.S. Pat. No. 8,114, 871, and U.S. Pat. No. 8,999,981, each of which is incorporated by reference in their entirety. As used herein, the term compound A (or cmpd A) refers to 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, which was disclosed in WO 2008/096260 and has the chemical structure:

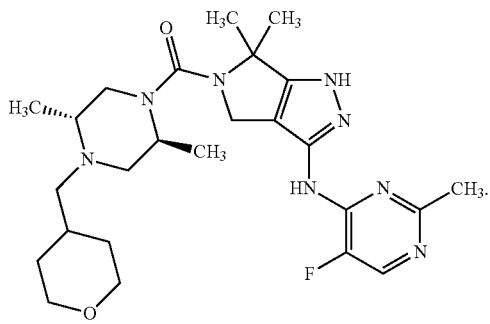 [SMILES: Cc1ncc(F)c(Nc2n[nH]c3c2CN(C(=O)N2C[C@@H](C)N(CC4CCOCC4)C[C@@H]2C)C3(C)C)n1]

Autoimmune Disease

Lupus

Lupus is a chronic inflammatory disease that occurs when the immune system attacks host tissues and organs. Inflammation caused by lupus can affect many different body systems, including joints, skin, kidneys, blood cells, brain, heart and lungs. Lupus can be difficult to diagnose because its signs and symptoms often mimic those of other ailments. The most distinctive sign of lupus is a facial rash that resembles the wings of a butterfly unfolding across both cheeks and occurs in many but not all cases of lupus. Some individuals are born with a tendency toward developing lupus, which may be triggered by infections, certain drugs or even sunlight. Currently available treatment can help control symptoms. Most individuals with lupus have mild disease characterized by episodes called flares, during which signs and symptoms are increased, then diminish or even disappear completely for a time. The signs and symptoms of lupus depend on which body systems are affected by the disease. The most common signs and symptoms include, fatigue and fever, joint pain, stiffness and swelling, butterfly-shaped rash on the face that covers the cheeks and bridge of the nose, skin lesions that appear or worsen with sun exposure, fingers and toes that turn white or blue when exposed to cold or during stressful periods (Raynaud's phenomenon), shortness of breath, chest pain, dry eyes, headaches, confusion and memory loss.

The origin lupus is suspected to result from a combination of genetics and environment causes. It appears that individuals with an inherited predisposition for lupus may develop the disease when they come into contact with environmental factors that can trigger lupus. Some potential triggers include sunlight, as exposure to the sun may bring on lupus skin lesions or trigger an internal response in susceptible individuals, and episodes of infection, as having an infection can initiate lupus or cause a relapse. Lupus can be triggered by certain types of anti-seizure medications, blood pressure medications and antibiotics. Individuals with drug-induced lupus usually see their symptoms go away when they stop taking the medication.

Systemic lupus erythematosus (SLE) is a severe disease in which autoreactive T cells and B cells make key contributions to the pathophysiology of the disease (Wahren-Herlenius and Dörner 2013, Lancet. 382:819-31; Murphy et al, 2013, Lancet. 31; 382:809-) Knockout of the PKCβ gene prevents the development of SLE in mice (Oleksyn D, et al., 2013, Arthritis Rheum 65:1022-31). This study supports the development of a selective inhibitor of PKCα, β and θ for autoimmune diseases.

Uveitis

Uveitis is a general term describing a group of inflammatory diseases that produces swelling and destroys eye tissues. The term "uveitis" is used because the diseases often affect a part of the eye called the uvea. Nevertheless, uveitis is not limited to the uvea. These diseases also affect the lens, retina, optic nerve, and vitreous, producing reduced vision or blindness. Common symptoms of uveitis include decreased vision, pain, light sensitivity, and increased floaters.

The uvea is the middle layer of the eye which contains much of the eye's blood vessels. This is one way that inflammatory cells can enter the eye. Located between the sclera, the white outer coat of the eye, and the inner layer of the eye, called the retina, the uvea consists of the iris, ciliary body, and choroid. Uveitis disrupts vision by primarily causing problems with the lens, retina, optic nerve, and vitreous. Specific types of Uveitis, classified by where it occurs in the eye, include, anterior uveitis, intermediate uveitis, posterior uveitis, and panuveitis uveitis.

Uveitis is primarily caused by inflammatory responses inside the eye. Exemplary inflammatory responses that lead to uveitis include an attack from the body's own immune system, infections or tumors occurring within the eye or in other parts of the body, bruises to the eye, and toxins that may penetrate the eye.

Diagnosis of uveitis may include a thorough examination and the recording of the patient's complete medical history. Laboratory tests may be done to rule out an infection or an autoimmune disorder. A central nervous system evaluation is often be performed on patients with a subgroup of intermediate uveitis, called pars planitis, to determine whether they have multiple sclerosis which is often associated with pars planitis. Exemplary eye exams used, include, an eye chart or visual acuity test which measures whether a patient's vision has decreased, a funduscopic exam where the pupil is dilated with eye drops and then a light is shown through with an instrument called an ophthalmoscope to noninvasively inspect the back, inside part of the eye, measurement of ocular pressure, and a slit lamp exam which noninvasively inspects much of the eye.

Uveitis treatments primarily try to eliminate inflammation, alleviate pain, prevent further tissue damage, and restore any loss of vision. Treatments depend on the type of uveitis a patient displays. Some, such as using corticosteroid eye drops and injections around the eye or inside the eye, may exclusively target the eye whereas other treatments, such immunosuppressive agents taken by mouth, may be used when the disease is occurring in both eyes, particularly in the back of both eyes.

Steroidal anti-inflammatory medications are also often prescribed, to be taken as eye drops, swallowed as a pill, injected around or into the eye, infused into the blood intravenously, or, released into the eye via a capsule that is surgically implanted inside the eye. In order to avoid undesired side effects arising from long term use of steroids, usually other agents are started if it appears that patients need moderate or high doses of oral steroids for more than 3 months.

Other immunosuppressive agents that are commonly used include medications such as methotrexate, mycophenolate, azathioprine, and cyclosporine. In some cases, biologic response modifiers (BRM), or biologics, such as, adalimumab, infliximab, daclizumab, abatacept, and rituximab are used. These drugs target specific elements of the immune system. Some of these drugs may increase the risk of having cancer.

Treatment can also depend on the specific type of uveitis the patient is suffering from. Anterior uveitis is treated, for example, taking eye drops that dilate the pupil to prevent muscle spasms in the iris and ciliary body or taking eye drops containing steroids, such as prednisone, to reduce inflammation. Intermediate, posterior, and pan-uveitis are often treated with injections around the eye, medications given by mouth, or, in some instances, time-release capsules that are surgically implanted inside the eye.

Encephalitis

The major role of the immune system is to recognize and fight infection. But due to dysfunction some components of the immune system may instead react with native proteins causing an autoimmune disease. When this reaction is against proteins in the brain it is termed autoimmune encephalitis (AE) and is a serious medical condition in which the immune system attacks the brain, impairing function. Autoimmune encephalitis is being increasingly recognized as important, and potentially reversible, non-infectious causes of an encephalitic syndrome. A variety autoimmune encephalitis have been described, including anti-LGI1 encephalitis (previously termed anti-voltage-gated potassium channel "anti-VGKC" antibody encephalitis) and anti-N-methyl-D-aspartic acid receptor (anti-NMDAR) encephalitis.

NMDA receptor antibody encephalitis is an autoimmune disease that causes psychiatric features, confusion, memory loss and seizures followed by a movement disorder, loss of consciousness and changes in blood pressure, heart rate and temperature. The disease can respond well to various therapies that dampen down the immune system and the removal of an underlying tumor if one is found, but improvement is often slow. The symptoms and signs seen in patients with NMDA receptor antibody associated encephalitis can be distinctive and prompt many clinicians to request the NMDA receptor antibody test to diagnose this condition. The disease mainly affects young people, with around 30% of cases under 18 years of age. Women are affected more often than men. Once a patient has been diagnosed with NMDA receptor antibody encephalitis, an underlying tumor is usually looked for. While very few males have tumors detected, recent reports suggest that between 20 and 57% of females may have an underlying tumor. The most common tumor found in women is called an ovarian teratoma. This is a non-cancerous tumor but it is thought to stimulate the production of NMDA receptor antibody.

Treatment consists of immune therapies and removal of a tumor, if present. The immune therapies use medicines to dampen down the immune system. These include steroids, immunoglobulins and plasma exchange therapies. In addition, some patients are treated with other drugs which dampen down the immune system, such as cyclophosphamide and rituximab.

When the antibodies target the voltage-gated potassium channel complex in the brain, they cause 'Voltage-gated Potassium Channel-complex Antibody-associated Limbic Encephalitis' (VGKC-LE). Men are roughly affected twice as often as women, with anti-LG1 antibody encephalitis. Initially, family members usually notice that their relative becomes forgetful, drowsy and withdrawn. Patients can also develop mood disorders, like depression, or bizarre thoughts and behaviors. In addition, seizures frequently occur. These may take the form of brief 'absences' when patients glaze over for a few seconds, also called 'temporal lobe epilepsy', or full blown arm and leg jerking which can be very disturbing for observers, also known as generalized seizures. Finally, patients may develop brief jerks of the face and arm, also called faciobrachial seizures. The last symptom is an important feature and highly suggestive of VGKC antibodies.

It has recently been discovered that the VGKC-antibodies do not actually target the potassium channel. They target proteins called LGI1, and less frequently CASPR2, which are tightly associated with the potassium channels in the brain. Therefore, various reports, diagnostic tests and doctors now use the terms VGKC, VGKC-complex, LGI1 and/or CASPR2 antibodies. In practice, there is usually little difference between these antibodies but this is an area currently under active research which may change the way we diagnose this disease in the future. VGKC-LE can be treated by dampening down the immune reaction that is causing the inflammation using immunosuppression, however, no single set of medications is proven to be superior to others and research into new or optimal treatments is ongoing. Nevertheless, most clinicians opt to use immunosuppression with oral or intravenous doses of steroids intravenous immunoglobulin and/or plasma exchange therapies.

Autoimmune encephalitis may also be triggered by infection in which case the term "Post-infectious Encephalitis" is used. Acute Disseminated Encephalomyelitis (ADEM) is a Post-infectious Encephalitis. The illness usually follows in the wake of a mild viral infection, such as those that cause rashes in childhood, or immunizations. Typically there is a delay of days to two to three weeks between the triggering infection and development of the Encephalitis. ADEM accounts for around 10% of all known cases of Encephalitis. ADEM usually affects children and begins after a childhood rash, exanthema, other viral infections or immunizations. There is usually a latent period of days to two to three weeks before symptoms emerge. The illness has been poorly understood and a variety of terminologies used to describe it, these including post-viral, post-infectious or para-infectious. The illness usually begins with less-specific symptoms such as fever, headache, stiff neck, vomiting and anorexia. These are rapidly followed by depression of consciousness in which the patient may become confused and occasionally comatose. Neurological features which may be detected include visual deterioration, clumsiness in arms and legs, paralysis down one side and seizures. The duration of these symptoms is variable. Some cases last a few weeks to a month, while other fatal cases have a rapid progressive course over a number of days.

There is a general agreement that a causative organism cannot be isolated from the brain of patients with ADEM. The association of the disease with a previous infection or immunization suggests an immunological process. Detailed laboratory studies involving measurement of anti-brain antibodies and of cellular immune responses to specific brain antigens suggest that these patients have developed an allergic response against their own brain constituents and this is an 'autoimmune' response.

The ideal form of treatment is immunomodulation which should be instituted once the diagnosis is made and has more benefit when given early. The diagnosis, however, may be difficult to make swiftly. High doses of steroids can often lead to a rapid resolution of symptoms with an excellent prognosis.

Methods of Treatment

Lupus

One embodiment provides a method of treating lupus in a subject in need thereof comprising administering to the subject a composition comprising a compound, or a pharmaceutically acceptable salt thereof, selected from the group consisting of:

$N^4$-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-N2-ethyl-5-fluoropyrimidine-2,4-diamine, $N^4$-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-5-fluoro-$N^2,N^2$-dimethylpyrimidine-2,4-diamine, $N^2$-cyclopropyl-N4-(6,6-dimethyl-5-{[(2 S)-2,4,5,5-tetramethylpiperazin-1-yl]carbonyl}-1,4,5,6-tetrahydropyrrolo[3,4-c]pyrazol-3-yl)-5-fluoropyrimidine-2,4-diamine, $N^4$-(6,6-dimethyl-5-{[(2 S)-2,4,5,5-tetramethylpiperazin-1-yl]carbonyl}-1,4,5,6-tetrahydropyrrolo[3,4-c]pyrazol-3-yl)-5-fluoro-$N^2$-methylpyrimidine-2,4-diamine, $N^4$-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-5-fluoro-$N^2$-isopropylpyrimidine-2,4-diamine, $N^4$-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-$N^2$-ethylpyrimidine-2,4-diamine, $N^4$-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-$N^2,N^2$-dimethylpyrimidine-2,4-diamine, 5-{[(8S)-6,8-dimethyl-6,9-diazaspiro[4.5]dec-9-yl]carbonyl}-N-(5-fluoro-2-methylpyrimidin-4-yl)-6,6-dimethyl-1,4,5,6-tetrahydropyrrolo[3,4-c]pyrazol-3-amine, $N^4$-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-$N^2$-ethyl-5-fluoropyrimidine-2,4-diamine, $N^4$-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)-$N^2$-ethyl-5-fluoropyrimidine-2,4-diamine, $N^2$-ethyl-5-fluoro-$N^4$-(5-{[(2S,5R)-4-(3-methoxypropyl)-2,5-dimethylpiperazin-1-yl]carbonyl})-6,6-dimethyl-1,4,5,6-tetrahydropyrrolo[3,4-c]pyrazol-3-yl)pyrimidine-2,4-diamine, $N^4$-(6,6-dimethyl-5-{[(2S,5R)-2,4,5-trimethylpiperazin-1-yl]carbonyl}-1,4,5,6-tetrahydropyrrolo[3,4-c]pyrazol-3-yl)-$N^2$-ethyl-5-fluoropyrimidine-2,4-diamine, 4-[(6,6-dimethyl-5-{[(2S,5R)-2,4,5-trimethylpiperazin-1-yl]carbonyl}-1,4,5,6-tetrahydropyrrolo[3,4-c]pyrazol-3-yl)amino]pyrimidine-2-carbonitrile, N-(2-ethyl-5-fluoropyrimidin-4-yl)-6,6-dimethyl-5-{[(2S)-2,4,5,5-tetramethylpiperazin-1-yl]carbonyl})-1,4,5,6-tetrahydropyrrolo[3,4-c]pyrazol-3-amine, N-(2-ethyl-5-fluoropyrimidin-4-yl)-5-{[(2S,5R)-4-(3-methoxypropyl)-2,5-dimethylpiperazin-1-yl]carbonyl}-6,6-dimethyl-1,4,5,6-tetrahydropyrrolo[3,4-c]pyrazol-3-amine, 2-((5S)-4-{[3-[(2-ethyl-5-fluoropyrimidin-4-yl)amino]-6,6-dimethyl-4,6-dihydropyrrolo[3,4-c]pyrazol-5(1H)-yl]carbonyl}-1,5-dimethylpiperazin-2-yl)ethanol, 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, N-(5-fluoro-2-methylpyrimidin-4-yl)-6,6-dimethyl-5-{[(2S)-2,4,5,5-tetramethylpiperazin-1-yl]carbonyl})-1,4,5,6-tetrahydropyrrolo[3,4-c]pyrazol-3-amine, N-(5-fluoro-2-propylpyrimidin-4-yl)-6,6-dimethyl-5-{[(2 S)-2,4,5,5-tetramethylpiperazin-1-yl]carbonyl})-1,4,5,6-tetrahydropyrrolo[3,4-c]pyrazol-3-amine, N-(5-fluoro-2-isopropylpyrimidin-4-yl)-6,6-dimethyl-5-{[(2S)-2,4,5,5-tetramethylpiperazin-1-yl]carbonyl})-1,4,5,6-tetrahydropyrrolo[3,4-c]pyrazol-3-amine, N-[5-fluoro-2-(methoxymethyl)pyrimidin-4-yl]-6,6-dimethyl-5-{[(2S)-2,4,5,5-tetramethylpiperazin-1-yl]carbonyl})-1,4,5,6-tetrahydropyrrolo[3,4-c]pyrazol-3-amine, 5-{[(2S,5R)-2,5-dimethyl-4-(tetrahydro-2H-pyran-4-ylmethyl)piperazin-1-yl]carbonyl}-N-(2-ethyl-5-fluoropyrimidin-4-yl)-6,6-dimethyl-1,4,5,6-tetrahydropyrrolo[3,4-c]pyrazol-3-amine, 5-{[(2S,5R)-2,5-dimethyl-4-(tetrahydro-2H-pyran-4-yl)piperazin-1-yl]carbonyl)}-N-(4-methoxypyrimidin-2-yl)-6,6-dimethyl-1,4,5,6-tetrahydropyrrolo[3,4-c]pyrazol-3-amine, 5-{[(2S,5R)-2,5-dimethyl-4-(tetrahydro-2H-pyran-4-yl)piperazin-1-yl]carbonyl}-6,6-dimethyl-N-(4-methylpyrimidin-2-yl)-1,4,5,6-tetrahydropyrrolo[3,4-c]pyrazol-3-amine, 5-{[(2S,5R)-2,5-dimethyl-4-(tetrahydro-2H-pyran-4-yl)piperazin-1-yl]carbonyl}-6,6-dimethyl-N-[4-(trifluoromethyl)pyrimidin-2-yl]-1,4,5,6-tetrahydropyrrolo[3,4-c]pyrazol-3-amine, 5-{[(2S,5R)-2,5-dimethyl-4-(tetrahydro-2H-pyran-4-ylmethyl)piperazin-1-yl]carbonyl}-6,6-dimethyl-N-(4-methylpyrimidin-2-yl)-1,4,5,6-tetrahydropyrrolo[3,4-c]pyrazol-3-amine, N-(2-ethoxy-5-fluoropyrimidin-4-yl)-6,6-dimethyl-5-{[(2S,5R)-2,4,5-trimethylpiperazin-1-yl]carbonyl})-1,4,5,6-tetrahydropyrrolo[3,4-c]pyrazol-3-amine, N-(2-ethoxy-5-fluoropyrimidin-4-yl)-6,6-dimethyl-5-{[4-ethyl(2S,5R)-2,5-dimethylpiperazin-1-yl]carbonyl})-1,4,5,6-tetrahydropyrrolo[3,4-c]pyrazol-3-amine, N-(2-ethoxy-5-fluoropyrimidin-4-yl)-6,6-dimethyl-5-{[(2S)-2,4,5,5-tetramethylpiperazin-1-yl]carbonyl})-1,4,5,6-tetrahydropyrrolo[3,4-c]pyrazol-3-amine, N-(2-ethoxy-5-fluoropyrimidin-4-yl)-5-{[(2S,5R)-4-(2-methoxyethyl)-2,5-dimethylpiperazin-1-yl]carbonyl}-6,6-dimethyl-1,4,5,6-tetrahydropyrrolo[3,4-c]pyrazol-3-amine, N-(2-ethoxy-5-fluoropyrimidin-4-yl)-5-{[(2S,5R)-4-(3-methoxypropyl)-2,5-dimethylpiperazin-1-yl]carbonyl}-6,6-dimethyl-1,4,5,6-tetrahydropyrrolo[3,4-c]pyrazol-3-amine, N-[5-fluoro-2-(2,2,2-trifluoroethoxy)pyrimidin-4-yl]-5-{[(2S,5R)-4-(3-methoxypropyl)-2,5-dimethylpiperazin-1-yl]carbonyl}-6,6-dimethyl-1,4,5,6-tetrahydropyrrolo[3,4-c]pyrazol-3-amine, N-[5-fluoro-2-(2,2,2-trifluoroethoxy)pyrimidin-4-yl]-6,6-dimethyl-5-{[(2S,5R)-2,4,5-trimethylpiperazin-1-yl]carbonyl}-1,4,5,6-tetrahydropyrrolo[3,4-c]pyrazol-3-amine, N-[5-fluoro-2-(2,2,2-trifluoroethoxy)pyrimidin-4-yl]-6,6-dimethyl-5-{[(2S)-2,4,5,5-tetramethylpiperazin-1-yl]carbonyl})-1,4,5,6-tetrahydropyrrolo[3,4-c]pyrazol-3-amine, 5-{[(2S,5R)-2,5-dimethyl-4-(tetrahydro-2H-pyran-4-ylmethyl)piperazin-1-yl]carbonyl}-N-(2-ethoxy-5-fluoropyrimidin-4-yl)-6,6-dimethyl-1,4,5,6-tetrahydropyrrolo[3,4-c]pyrazol-3-amine, 5-{[(2S,5R)-2,5-dimethyl-4-(tetrahydro-2H-pyran-4-yl)piperazin-1-yl]carbonyl}-N-(2-ethoxy-5-fluoropyrimidin-4-yl)-6,6-dimethyl-1,4,5,6-tetrahydropyrrolo[3,4-c]pyrazol-3-amine, 2-((5S)-4-{[3-[(2-ethoxy-5-fluoropyrimidin-4-yl)amino]-6,6-dimethyl-4,6-dihydropyrrolo[3,4-c]pyrazol-5(1H)-yl]carbonyl}-1,5-dimethylpiperazin-2-yl)ethanol, 2-((5S)-4-{[3-[(2-ethoxy-5-fluoropyrimidin-4-yl)amino]-6,6-dimethyl-4,6-dihydropyrrolo[3,4-c]pyrazol-5(1H)-yl]carbonyl}-1,5-dimethylpiperazin-2-yl)ethanol, 5-[(4-fluoro-1-methylpiperidin-4-yl)carbonyl]-N-[5-fluoro-2-(2,2,2-trifluoroethoxy)pyrimidin-4-yl]-6,6-dimethyl-1,4,5,6-tetrahydropyrrolo[3,4-c]pyrazol-3-amine, 5-{[(2S,5R)-2,5-dimethyl-4-(tetrahydro-2H-pyran-4-ylmethyl)piperazin-1-yl]carbonyl}-N-[5-fluoro-2-(methoxymethyl)pyrimidin-4-yl]-6,6-dimethyl-1,4,5,6-tetrahydropyrrolo[3,4-c]pyrazol-3-amine, and 2-((5S)-4-{[3-{[5-fluoro-2-(methoxymethyl)pyrimidin-4-yl]amino}-6,6-dimethyl-4,6-dihydropyrrolo[3,4-c]pyrazol-5(1H)-yl]carbonyl}-1,5-dimethylpiperazin-2-yl)ethanol.

Another embodiment provides the method of treating lupus, wherein the compound is $N^4$-(5-{[(2S,5R)-2,5-dimethyl-4-(tetrahydro-2H-pyran-4-ylmethyl)piperazin-1-yl]carbonyl})-6,6-dimethyl-1,4,5,6-tetrahydropyrrolo[3,4-c]pyrazol-3-yl)-$N^2$-ethyl-5-fluoropyrimidine-2,4-diamine, or a pharmaceutically acceptable salt thereof. Another embodiment provides the method of treating lupus, wherein the compound is $N^4$-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)-$N^2$-ethyl-5-fluoropyrimidine-2,4-diamine, or a pharmaceutically acceptable salt thereof. Another embodiment provides the method of treating lupus, wherein the compound is 5-{[(2S,5R)-2,5-dimethyl-4-(tetrahydro-2H-pyran-4-ylmethyl)piperazin-1-yl]carbonyl}-N-(5-fluoro-2-methoxypyrimidin-4-yl)-6,6-dimethyl-1,4,5,6-tetrahydropyrrolo[3,4-c]pyrazol-3-amine, or a pharmaceutically acceptable salt thereof. Another embodiment provides the method of treating lupus, wherein the compound is 5-{[(2S,5R)-2,5-dimethyl-4-(tetrahydro-2H-pyran-4-ylmethyl)piperazin-1-yl]carbonyl}-N-(2-ethyl-5-fluoropyrimidin-4-yl)-6,6-dimethyl-1,4,5,6-tetrahydropyrrolo[3,4-c]pyrazol-3-amine, or a pharmaceutically acceptable salt thereof. Another embodiment provides the method of treating lupus, wherein the compound is 5-{[(2S,5R)-2,5-dimethyl-4-(tetrahydro-2H-pyran-4-yl)piperazin-1-yl]carbonyl}-N-(4-methoxypyrimidin-2-yl)-6,6-dimethyl-1,4,5,6-tetrahydropyrrolo[3,4-c]pyrazol-3-amine, or a pharmaceutically acceptable salt thereof. Another embodiment provides the method of treating lupus, wherein the compound is 5-{[(2S,5R)-2,5-dimethyl-4-(tetrahydro-2H-pyran-4-yl)piperazin-1-yl]carbonyl)}-6,6-dimethyl-N-[4-(trifluoromethyl)pyrimidin-2-yl]-1,4,5,6-tetrahydropyrrolo[3,4-c]pyrazol-3-amine, or a pharmaceutically acceptable salt thereof. Another embodiment provides the method of treating lupus, wherein the compound is 5-{[(2S,5R)-2,5-dimethyl-4-(tetrahydro-2H-pyran-4-yl)piperazin-1-yl]carbonyl}-N-(2-ethoxy-5-fluoropyrimidin-4-yl)-6,6-dimethyl-1,4,5,6-tetrahydropyrrolo[3,4-c]pyrazol-3-amine, or a pharmaceutically acceptable salt thereof. Another embodiment provides the method of treating lupus, wherein the compound is $N^4$-(6,6-dimethyl-5-{[(2 S)-2,4,5,5-tetramethylpiperazin-1-yl]carbonyl}-1,4,5,6-tetrahydropyrrolo[3,4-c]pyrazol-3-yl)-N2-ethyl-5-fluoropyrimidine-2,4-diamine, or a pharmaceutically acceptable salt thereof. Another embodiment provides the method of treating lupus, wherein the compound is $N^4$-(6,6-dimethyl-5-{[(2 S)-2,4,5,5-tetramethylpiperazin-1-yl]carbonyl}-1,4,5,6-tetrahydropyrrolo[3,4-c]pyrazol-3-yl)-$N^2$-ethylpyrimidine-2,4-diamine, or a pharmaceutically acceptable salt thereof. Another embodiment provides the method of treating lupus, wherein the lupus is lupus erythematosus.

One embodiment provides a method of treating lupus erythematosus in a subject in need thereof comprising administering to the subject a composition comprising a compound having the formula 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof, and a pharmaceutically acceptable excipient.

One embodiment provides a method of treating lupus in a subject in need thereof comprising administering to the subject a composition comprising a compound, or a pharmaceutically acceptable salt thereof, selected from the group consisting of:

$N^2$-(cyclopropylmethyl)-$N^4$-(6,6-dimethyl-5-{[(2 S)-2,4,5,5-tetramethylpiperazin-1-yl]carbonyl}-1,4,5,6-tetrahydropyrrolo[3,4-c]pyrazol-3-yl)-5-fluoropyrimidine-2,4-diamine;

$N^4$-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-5-fluoro-$N^2$-isobutylpyrimidine-2,4-diamine;

5-{[(2S,5R)-4-ethyl-2,5-dimethylpiperazin-1-yl]carbonyl)}-N-(5-fluoro-2-methoxypyrimidin-4-yl)-6,6-dimethyl-1,4,5,6-tetrahydropyrrolo[3,4-c]pyrazol-3-amine;

5-{[(2S,5R)-4-ethyl-2,5-dimethylpiperazin-1-yl]carbonyl)}-N-(5-fluoro-2-methylpyrimidin-4-yl)-6,6-dimethyl-1,4,5,6-tetrahydropyrrolo[3,4-c]pyrazol-3-amine;

5-{[(2S,5R)-4-ethyl-2,5-dimethylpiperazin-1-yl]carbonyl)}-N-(5-fluoro-2,6-dimethylpyrimidin-4-yl)-6,6-dimethyl-1,4,5,6-tetrahydropyrrolo[3,4-c]pyrazol-3-amine;

2(S),5(S)-{[dimethyl-4-methylpiperazin-1-yl]carbonyl}-N-(5-fluoro-2-methylpyrimidin-4-yl)-6,6-dimethyl-1,4,5,6-tetrahydropyrrolo[3,4-c]pyrazol-3-amine;

[3-(5-fluoro-2-methyl-pyrimidin-4-ylamino)-6,6-dimethyl-4,6-dihydro-1H-pyrrolo[3,4-c]pyrazol-5-yl]-[4-(3-hydroxy-propyl)-2,5-dimethyl-piperazin-1-yl]-methanone;

$N^4$-(6,6-dimethyl-5-{[(3S,8aS)-3-methylhexahydropyrrolo[1,2-a]pyrazin-2(1H)-yl]carbonyl})-1,4,5,6-tetrahydropyrrolo[3,4-c]pyrazol-3-yl)-N2-ethyl-5-fluoropyrimidine-2,4-diamine;

$N^2$-ethyl-5-fluoro-$N^4$-(5-{[(2S,5R)-4-(2-methoxyethyl)-2,5-dimethylpiperazin-1-yl]carbonyl}-6,6-dimethyl-1,4,5,6-tetrahydropyrrolo[3,4-c]pyrazol-3-yl)pyrimidine-2,4-diamine;

N4-(5-{[(2S,5R)-2,5-dimethyl-4-(3,3,3-trifluoropropyl)piperazin-1-yl]carbonyl}-6,6-dimethyl-1,4,5,6-tetrahydropyrro[3,4-c]pyrazol-3-yl)-N2-ethyl-5-fluoropyrimidine-2,4-diamine;

N-(5-fluoro-2-morpholin-4-ylpyrimidin-4-yl)-6,6-dimethyl-5-{[(2S,5R)-2,4,5-trimethylpiperazin-1-yl]carbonyl}-1,4,5,6-tetrahydropyrrolo[3,4-c]pyrazol-3-amine;

$N^2$-ethyl-5-fluoro-$N^4$-{5-[(4-fluoro-1-methylpiperidin-4-yl)carbonyl]-6,6-dimethyl-1,4,5,6-tetrahydropyrrolo[3,4-c]pyrazol-3-yl}pyrimidine-2,4-diamine;

N-(2-ethyl-5-fluoropyrimidin-4-yl)-6,6-dimethyl-5-{[(2S,5R)-2,4,5-trimethylpiperazin-1-yl]carbonyl}-1,4,5,6-tetrahydropyrrolo[3,4-c]pyrazol-3-amine;

N-(2-ethoxypyrimidin-4-yl)-6,6-dimethyl-5-{[(2S,5R)-2,4,5-trimethylpiperazin-1-yl]carbonyl})-1,4,5,6-tetrahydropyrrolo[3,4-c]pyrazol-3-amine;

5-{[(2S,5R)-2,5-dimethyl-4-(3,3,3-trifluoropropyl)piperazin-1-yl]carbonyl)}-N-(2-ethyl-5-fluoropyrimidin-4-yl)-6,6-dimethyl-1,4,5,6-tetrahydropyrrolo[3,4-c]pyrazol-3-amine;

5-[(4-fluoro-1-methylpiperidin-4-yl)carbonyl]-N-(5-fluoro-2-methylpyrimidin-4-yl)-6,6-dimethyl-1,4,5,6-tetrahydropyrrolo[3,4-c]pyrazol-3-amine;

N-(2-ethyl-5-fluoropyrimidin-4-yl)-5-[(4-fluoro-1-methylpiperidin-4-yl)carbonyl]-6,6-dimethyl-1,4,5,6-tetrahydropyrrolo[3,4-c]pyrazol-3-amine;

N-(5-fluoro-2-methylpyrimidin-4-yl)-6,6-dimethyl-5-{[(3S,8aS)-3-methylhexahydropyrrolo[1,2-a]pyrazin-2(1H)-yl]carbonyl}-1,4,5,6-tetrahydropyrrolo[3,4-c]pyrazol-3-amine;

N-(5-fluoro-2-methylpyrimidin-4-yl)-6,6-dimethyl-5-{[(2S,5R)-2,4,5-trimethylpiperazin-1-yl]carbonyl}-1,4,5,6-tetrahydropyrrolo[3,4-c]pyrazol-3-amine;

5-{[(3S)-3-ethyl-4-methylpiperazin-1-yl]carbonyl}-N-(5-fluoro-2-methylpyrimidin-4-yl)-6,6-dimethyl-1,4,5,6-tetrahydropyrrolo[3,4-c]pyrazol-3-amine;

5-{[(3R)-3-ethyl-4-methylpiperazin-1-yl]carbonyl}-N-(5-fluoro-2-methylpyrimidin-4-yl)-6,6-dimethyl-1,4,5,6-tetrahydropyrrolo[3,4-c]pyrazol-3-amine;

5-{[(2S,5R)-2,5-dimethyl-4-(tetrahydro-2H-pyran-4-yl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine;

4-[((2R,5S)-4-{[3-[(5-fluoro-2-methylpyrimidin-4-yl)amino]-6,6-dimethyl-4,6-dihydropyrrolo[3,4-c]pyrazol-5(1H)-yl]carbonyl}-2,5-dimethylpiperazin-1-yl)methyl]tetrahydro-2H-pyran-4-ol;

2-((5S)-4-{[3-[(5-fluoro-2-methylpyrimidin-4-yl)amino]-6,6-dimethyl-4,6-dihydropyrrolo[3,4-c]pyrazol-5(1H)-yl]carbonyl}-1,5-dimethylpiperazin-2-yl)ethanol;

2-((5S)-4-{[3-[(5-fluoro-2-methylpyrimidin-4-yl)amino]-6,6-dimethyl-4,6-dihydropyrrolo[3,4-c]pyrazol-5(1H)-yl]carbonyl}-1,5-dimethylpiperazin-2-yl)ethanol;

5-{[(2S,5R)-2,5-dimethyl-4-(tetrahydro-2H-pyran-4-ylmethyl)piperazin-1-yl]carbonyl}-N-(4-methoxypyrimidin-2-yl)-6,6-dimethyl-1,4,5,6-tetrahydropyrrolo[3,4-c]pyrazol-3-amine;

N-(4, 6-dimethylpyrimidin-2-yl)-5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-amine;

N-[5-fluoro-2-(3-methoxypropoxy)pyrimidin-4-yl]-6,6-dimethyl-5-{[(2 S)-2,4,5,5-tetramethylpiperazin-1-yl]carbonyl}-1,4,5,6-tetrahydropyrrolo[3,4-c]pyrazol-3-amine;

N-[5-fluoro-2-(3-methoxypropoxy)pyrimidin-4-yl]-6,6-dimethyl-5-{[(2S,5R)-2,4,5-trimethylpiperazin-1-yl]carbonyl}-1,4,5,6-tetrahydropyrrolo[3,4-c]pyrazol-3-amine;

N-[5-fluoro-2-(2-methoxyethoxy)pyrimidin-4-yl]-6,6-dimethyl-5-{[(2S)-2,4,5,5-tetramethylpiperazin-1-yl]carbonyl}-1,4,5,6-tetrahydropyrrolo[3,4-c]pyrazol-3-amine;

N-[5-fluoro-2-(2-methoxyethoxy)pyrimidin-4-yl]-6,6-dimethyl-5-{[(2S,5R)-2,4,5-trimethylpiperazin-1-yl]carbonyl}-1,4,5,6-tetrahydropyrrolo[3,4-c]pyrazol-3-amine;

2(S), 5(S)-{[dimethyl-4-methylpiperazin-1-yl]carbonyl}-N-(5-fluoro-2-ethoxypyrimidin-4-yl)-6,6-dimethyl-1,4,5,6-tetrahydropyrrolo[3,4-c]pyrazol-3-amine;

[3-(2-Ethoxy-5-fluoro-pyrimidin-4yl-amino)-6,6-dimethyl-4,6-dihydro-1H-pyrrolo[3,4-c]pyrazol-5-yl]-(R)-hexahydro-pyrrolo[1,2-a]pyrazin-2-yl-methanone;

5-{[(3S,8aS)-3,8a-dimethylhexahydropyrrolo[1,2-a]pyrazin-2(1H)-yl]carbonyl)}-N-(2-ethoxy-5-fluoropyrimidin-4-yl)-6,6-dimethyl-1,4,5,6-tetrahydropyrrolo[3,4-c]pyrazol-3-amine;

5-{[(3S)-3,4-dimethylpiperazin-1-yl]carbonyl}-N-(2-ethoxy-5-fluoropyrimidin-4-yl)-6,6-dimethyl-1,4,5,6-tetrahydropyrrolo[3,4-c]pyrazol-3-amine;

5-{[(3R)-3,4-dimethylpiperazin-1-yl]carbonyl}-N-(2-ethoxy-5-fluoropyrimidin-4-yl)-6,6-dimethyl-1,4,5,6-tetrahydropyrrolo[3,4-c]pyrazol-3-amine;

5-{[(2S,5R)-2,5-dimethyl-4-(3,3,3-trifluoropropyl)piperazin-1-yl]carbonyl)}-N-(2-ethoxy-5-fluoropyrimidin-4-yl)-6,6-dimethyl-1,4,5,6-tetrahydropyrrolo[3,4-c]pyrazol-3-amine;

N-(2-ethoxy-5-fluoropyrimidin-4-yl)-5-{[(3S,8aS)-3-isopropylhexahydropyrrolo[1,2-a]pyrazin-2(1H)-yl]carbonyl}-6,6-dimethyl-1,4,5,6-tetrahydropyrrolo[3,4-c]pyrazol-3-amine;

4-[((2R,5S)-4-{[3-[(2-ethoxy-5-fluoropyrimidin-4-yl)amino]-6,6-dimethyl-4,6-dihydropyrrolo[3,4-c]pyrazol-5(1H)-yl]carbonyl}-2,5-dimethylpiperazin-1-yl)methyl]tetrahydro-2H-pyran-4-ol;

2-((5S)-4-{[3-[(5-fluoro-2-methoxypyrimidin-4-yl)amino]-6,6-dimethyl-4,6-dihydropyrrolo[3,4-c]pyrazol-5(1H)-yl]carbonyl}-1,5-dimethylpiperazin-2-yl)ethanol;

2-((5S)-4-{[3-[(5-fluoro-2-methoxypyrimidin-4-yl)amino]-6,6-dimethyl-4,6-dihydropyrrolo[3,4-c]pyrazol-5(1H)-yl]carbonyl}-1,5-dimethylpiperazin-2-yl)ethanol;

N-(2-ethoxy-5-fluoropyrimidin-4-yl)-5-[(4-fluoro-1-methylpiperidin-4-yl)carbonyl]-6,6-dimethyl-1,4,5,6-tetrahydropyrrolo[3,4-c]pyrazol-3-amine;

N-[5-fluoro-2-(2-methoxyethoxy)pyrimidin-4-yl]-5-[(4-fluoro-1-methylpiperidin-4-yl)carbonyl]-6,6-dimethyl-1,4,5,6-tetrahydropyrrolo[3,4-c]pyrazol-3-amine;

N-[5-fluoro-2-(3-methoxypropoxy)pyrimidin-4-yl]-5-[(4-fluoro-1-methylpiperidin-4-yl)carbonyl]-6,6-dimethyl-1,4,5,6-tetrahydropyrrolo[3,4-c]pyrazol-3-amine;

N-(2-ethoxy-5-fluoropyrimidin-4-yl)-6,6-dimethyl-5-{[1-(3,3,3-trifluoropropyl)piperidin-4-yl]carbonyl}-1,4,5,6-tetrahydropyrrolo[3,4-c]pyrazol-3-amine;

N-(2-ethoxy-5-fluoropyrimidin-4-yl)-6,6-dimethyl-5-{[1-(tetrahydro-2H-pyran-4-yl)piperidin-4-yl]carbonyl}-1,4,5,6-tetrahydropyrrolo[3,4-c]pyrazol-3-amine;

N-(4-ethoxypyrimidin-2-yl)-6,6-dimethyl-5-{[(2S,5R)-2,4,5-trimethylpiperazin-1-yl]carbonyl})-1,4,5,6-tetrahydropyrrolo[3,4-c]pyrazol-3-amine;

N-(4-ethoxypyrimidin-2-yl)-5-{[(2S,5R)-4-(3-methoxypropyl)-2,5-dimethylpiperazin-1-yl]carbonyl}-6,6-dimethyl-1,4,5,6-tetrahydropyrrolo[3,4-c]pyrazol-3-amine; or 2-((5S)-4-{[3-{[5-fluoro-2-(methoxymethyl)pyrimidin-4-yl]amino}-6,6-dimethyl-4,6-dihydropyrrolo[3,4-c]pyrazol-5(1H)-yl]carbonyl}-1,5-dimethylpiperazin-2-yl)ethanol.

Another embodiment provides the method of treating lupus, wherein the compound is N-(4-ethoxypyrimidin-2-yl)-6,6-dimethyl-5-{[(2S,5R)-2,4,5-trimethylpiperazin-1-yl]carbonyl}-1,4,5,6-tetrahydropyrrolo[3,4-c]pyrazol-3-amine, or a pharmaceutically acceptable salt thereof. Another embodiment provides the method of treating lupus, wherein the compound is 5-{[(3S,8aS)-3,8a-dimethylhexahydropyrrolo[1,2-a]pyrazin-2(1H)-yl]carbonyl)}-N-(2-ethoxy-5-fluoropyrimidin-4-yl)-6,6-dimethyl-1,4,5,6-tetrahydropyrrolo[3,4-c]pyrazol-3-amine, or a pharmaceutically acceptable salt thereof. Another embodiment provides the method of treating lupus, wherein the compound is N-(4,6-dimethylpyrimidin-2-yl)-5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-amine, or a pharmaceutically acceptable salt thereof. Another embodiment provides the method of treating lupus, wherein the compound is N-[5-fluoro-2-(3-methoxypropoxy)pyrimidin-4-yl]-6,6-dimethyl-5-{[(2 S)-2,4,5,5-tetramethylpiperazin-1-yl]carbonyl}-1,4,5,6-tetrahydropyrrolo[3,4-c]pyrazol-3-amine, or a pharmaceutically acceptable salt thereof. Another embodiment provides the method of treating lupus, wherein the compound is N-(2-ethoxypyrimidin-4-yl)-6,6-dimethyl-5-{[(2S,5R)-2,4,5-trimethylpiperazin-1-yl]carbonyl}-1,4,5,6-tetrahydropyrrolo[3,4-c]pyrazol-3-amine, or a pharmaceutically acceptable salt thereof. Another embodiment provides the method of treating lupus, wherein the compound is N-(2-ethyl-5-fluoropyrimidin-4-yl)-6,6-dimethyl-5-{[(2S,5R)-2,4,5-trimethylpiperazin-1-yl]carbonyl}-1,4,5,6-tetrahydropyrrolo[3,4-c]pyrazol-3-amine, or a pharmaceutically acceptable salt thereof. Another embodiment provides the method of treating lupus, wherein the compound is $N^2$-ethyl-5-fluoro-$N^4$-(5-{[(2S,5R)-4-(2-methoxyethyl)-2,5-dimethylpiperazin-1-yl]carbonyl})-6,6-dimethyl-1,4,5,6-tetrahydropyrrolo[3,4-c]pyrazol-3-yl)pyrimidine-2,4-diamine, or a pharmaceutically acceptable salt thereof. Another embodiment provides the method of treating lupus, wherein the compound is 5-{[(2S,5R)-2,5-dimethyl-4-(tetrahydro-2H-pyran-4-yl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof. Another embodiment provides the method of treating lupus, wherein the compound is 5-{[(2S,5R)-4-ethyl-2,5-dimethylpiperazin-1-yl]carbonyl}-N-(5-fluoro-2,6-dimethylpyrimidin-4-yl)-6,6-dimethyl-1,4,5,6-tetrahydropyrrolo[3,4-c]pyrazol-3-amine, or a pharmaceutically acceptable salt thereof. Another embodiment provides the method of treating lupus, wherein the compound is N-(2-ethoxy-5-fluoropyrimidin-4-yl)-5-[(4-fluoro-1-methylpiperidin-4-yl)carbonyl]-6,6-dimethyl-1,4,5,6-tetrahydropyrrolo[3,4-c]pyrazol-3-amine, or a pharmaceutically acceptable salt thereof. Another embodiment provides the method of treating lupus, wherein the compound is 4-[((2R,5S)-4-{[3-[(2-ethoxy-5-fluoropyrimidin-4-yl)amino]-6,6-dimethyl-4,6-dihydropyrrolo[3,4-c]pyrazol-5(1H)-yl]carbonyl}-2,5-dimethylpiperazin-1-yl)methyl] tetrahydro-2H-pyran-4-ol, or a pharmaceutically acceptable salt thereof. Another embodiment provides the method of treating lupus, wherein the compound is N-[5-fluoro-2-(2-methoxyethoxy)pyrimidin-4-yl]-6,6-dimethyl-5-{[(2S,5R)-2,4,5-trimethylpiperazin-1-yl]carbonyl}-1,4,5,6-tetrahydropyrrolo[3,4-c]pyrazol-3-amine, or a pharmaceutically acceptable salt thereof. Another embodiment provides the method of treating lupus, wherein the compound is 5-{[(2S,5R)-2,5-dimethyl-4-(tetrahydro-2H-pyran-4-ylmethyl)piperazin-1-yl]carbonyl}-N-(4-methoxypyrimidin-2-yl)-6,6-dimethyl-1,4,5,6-tetrahydropyrrolo[3,4-c]pyrazol-3-amine, or a pharmaceutically acceptable salt thereof. Another embodiment provides the method of treating lupus, wherein the compound is N-(5-fluoro-2-methylpyrimidin-4-yl)-6,6-dimethyl-5-{[(2S,5R)-2,4,5-trimethylpiperazin-1-yl]carbonyl}-1,4,5,6-tetrahydropyrrolo[3,4-c]pyrazol-3-amine, or a pharmaceutically acceptable salt thereof. Another embodiment provides the method of treating lupus, wherein the compound is $N^2$-(cyclopropylmethyl)-$N^4$-(6,6-dimethyl-5-{[(2 S)-2,4,5,5-tetramethylpiperazin-1-yl]carbonyl})-1,4,5,6-tetrahydropyrrolo[3,4-c]pyrazol-3-yl)-5-fluoropyrimidine-2,4-diamine, or a pharmaceutically acceptable salt thereof.

One embodiment provides a method of treating lupus in a subject in need thereof comprising administering to the subject a composition comprising a compound, or a pharmaceutically acceptable salt thereof, selected from the group consisting of:

N-(5-{[(8 S)-6, 8-dimethyl-6,9-diazaspiro[4.5]dec-9-yl]carbonyl}-6,6-dimethyl-1,4,5,6-tetrahydropyrrolo[3,4-c]pyrazol-3-yl)pyridine-2-carboxamide;

N-(5-((3S,8aS)-3-benzyl-octahydropyrrolo[1,2-a]pyrazine-2-carbonyl)-6,6-dimethyl-1,4,5,6-tetrahydropyrrolo[3,4-c]pyrazol-3-yl)benzamide;

N-(5-((3S,8aS)-3-benzyl-octahydropyrrolo[1,2-a]pyrazine-2-carbonyl)-6,6-dimethyl-1,4,5,6-tetrahydropyrrolo[3,4-c]pyrazol-3-yl)-3-methoxybenzamide;

3,4-dichloro-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)benzamide;

N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-4,6-dimethylpicolinamide;

N-(5-((3S,8aS)-3-(cyclohexylmethyl)-octahydropyrrolo[1,2-a]pyrazine-2-carbonyl)-6,6-dimethyl-1,4,5,6-tetrahydropyrrolo[3,4-c]pyrazol-3-yl)picolinamide;

3-cyano-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)benzamide;

N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-2,3-dihydrobenzofuran-5-carboxamide;

4,5-dichloro-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)thiazole-2-carboxamide;

N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)H-pyrrolo[1,2-f]pyrimidine-3-carboxamide;

N-(5-((2R,5S)-2-(2-hydroxyethyl)-5-methyl-1-propylpiperazine-4-carbonyl)-6,6-dimethyl-1,4,5,6-tetrahydropyrrolo[3,4-c]pyrazol-3-yl)picolinamide;

N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-5-nitropicolinamide;

N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)quinoline-2-carboxamide;

N-(5-((+/−)-trans-1-allyl-2,5-dimethylpiperazine-4-carbonyl)-6,6-dimethyl-1,4,5,6-tetrahydropyrrolo[3,4-c]pyrazol-3-yl)picolinamide;

5-bromo-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)picolinamide;

N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-5-fluoropicolinamide;

N-(5-((+/−)-trans-1-ethyl-2,5-dimethylpiperazine-4-carbonyl)-6,6-dimethyl-1,4,5,6-tetrahydropyrrolo[3,4-c]pyrazol-3-yl)picolinamide;

N-(5-((+/−)-trans-1-(cyclopropylmethyl)-2,5-dimethylpiperazine-4-carbonyl)-6,6-dimethyl-1,4,5,6-tetrahydropyrrolo[3,4-c]pyrazol-3-yl)picolinamide;

N-(5-(1-(3-hydroxypropyl)-2,5-dimethylpiperazine-4-carbonyl)-6,6-dimethyl-1,4,5,6-tetrahydropyrrolo[3,4-c]pyrazol-3-yl)picolinamide;

N-(5-((3S,8aS)-3-isopropyl-octahydropyrrolo[1,2-a]pyrazine-2-carbonyl)-6,6-dimethyl-1,4,5,6-tetrahydropyrrolo[3,4-c]pyrazol-3-yl)picolinamide;

2-bromo-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)thiazole-4-carboxamide;

N-(6,6-dimethyl-5-((2R,5S)-1,2,5-trimethylpiperazine-4-carbonyl)-1,4,5,6-tetrahydropyrrolo[3,4-c]pyrazol-3-yl)picolinamide;

N-(5-((2R,5S)-1-ethyl-2,5-dimethylpiperazine-4-carbonyl)-6,6-dimethyl-1,4,5,6-tetrahydropyrrolo[3,4-c]pyrazol-3-yl)picolinamide;

N-(5-((2R,5S)-2,5-dimethyl-1-propylpiperazine-4-carbonyl)-6,6-dimethyl-1,4,5,6-tetrahydropyrrolo[3,4-c]pyrazol-3-yl)picolinamide;

N-(5-((2R,5S)-1-(cyclopropylmethyl)-2,5-dimethylpiperazine-4-carbonyl)-6,6-dimethyl-1,4,5,6-tetrahydropyrrolo[3,4-c]pyrazol-3-yl)picolinamide;

N-(5-((2R,5S)-1-butyl-2,5-dimethylpiperazine-4-carbonyl)-6,6-dimethyl-1,4,5,6-tetrahydropyrrolo[3,4-c]pyrazol-3-yl)picolinamide;

N-(6,6-dimethyl-5-{[(2S)-2,4,5,5-tetramethylpiperazin-1-yl]carbonyl}-1,4,5,6-tetrahydropyrrolo[3,4-c]pyrazol-3-yl)pyridine-2-carboxamide;

N-(5-{[(7S)-5,7-dimethyl-5,8-diazaspiro[3.5]non-8-yl]carbonyl}-6,6-dimethyl-1,4,5,6-tetrahydropyrrolo[3,4-c]pyrazol-3-yl)pyridine-2-carboxamide;

N-(5-{[(2S,5R)-4-(3-methoxypropyl)-2,5-dimethylpiperazin-1-yl]carbonyl}-6,6-dimethyl-1,4,5,6-tetrahydropyrrolo[3,4-c]pyrazol-3-yl)pyridine-2-carboxamide;

N-(5-((2R,5S)-2,5-dimethyl-1-(2(tetradhydro-2H-pyran-4-yl)ethyl)piperazine-4-carbonyl)-6,6-dimethyl-1,4,5,6-tetrahydropyrrolo[3,4-c]pyrazol-3-yl)picolinamide;

N-(5-((2R,5S)-2,5-dimethyl-1-(tetrahydro-2H-pyran-4-yl)piperazine-4-carbonyl)-6,6-dimethyl-1,4,5,6-tetrahydropyrrolo[3,4-c]pyrazol-3-yl)picolinamide;

N-(5-{[(2S,5R)-2,5-dimethyl-4-(tetrahydrofuran-3-ylmethyl)piperazin-1-yl]carbonyl})-6,6-dimethyl-1,4,5,6-tetrahydropyrrolo[3,4-c]pyrazol-3-yl)pyridine-2-carboxamide;

N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)isoquinoline-3-carboxamide;

N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-1,6-naphthyridine-2-carboxamide;

3-cyclopropyl-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-1H-pyrazole-5-carboxamide;

N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)quinoxaline-2-carboxamide;

3-tert-butyl-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-1-methyl-1H-pyrazole-5-carboxamide;

3-cyclopropyl-N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-1H-pyrazole-5-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-5-fluoropyridine-2-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-5-methoxypyridine-2-carboxamide;

5-chloro-N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)pyridine-2-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-6-methylpyridine-2-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-3-ethyl-1-methyl-1H-pyrazole-5-carboxamide;

2-cyclopropyl-N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-1,3-oxazole-4-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-3-methylbenzamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-4-fluorobenzamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-3-fluorobenzamide;

N-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)-5-ethylpyridine-2-carboxamide;

N-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)-5-methylpyridine-2-carboxamide;

N-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)-5-methoxypyridine-2-carboxamide;

5-chloro-N-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)pyridine-2-carboxamide;

2-(3,5-dimethylisoxazol-4-yl)-N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)acetamide;

5-cyano-N-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)pyridine-2-carboxamide;

and 5-cyano-N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)pyridine-2-carboxamide.

One embodiment provides a method of treating lupus in a subject in need thereof comprising administering to the subject a composition comprising a compound, or a pharmaceutically acceptable salt thereof, having the formula (I):

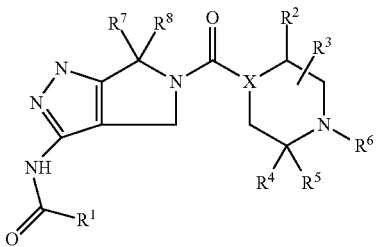

(I)

wherein:
X is C or N;
R$^1$ is selected from an aryl or

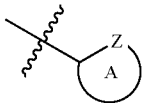

wherein ring A is a 5 to 6 membered heterocyclyl containing Z, wherein Z is an O, S or N heteroatom which is adjacent to the point of attachment, and wherein R$^1$ is optionally further substituted with 0 to 3 R$^9$ groups and wherein two of the R$^9$ groups may optionally cyclize to form an aryl or a 5-6 membered heterocyclyl ring containing N or S fused to the aryl or heterocyclyl to which it is attached;

R$^2$ is H or C$_1$-C$_6$ alkyl optionally further substituted with 0 to 3 R$^9$ groups;

when X is N, R$^3$ may be attached to any carbon on the ring and is selected from H, C$_1$-C$_6$ alkyl, halide, or perfluoroalkyl;

when X is C, R$^3$ is a fluoro and is attached to X;

R$^4$ and R$^5$ are each independently selected from H, R$^a$—O—R$^b$, C$_1$-C$_8$ alkyl, C$_2$-C$_8$ alkenyl, C$_2$-C$_8$ alkynyl, —(R$^d$)$_m$—(C$_3$-C$_{12}$ cycloalkyl), —(R$^d$)$_m$-aryl, —(R$^d$)$_m$-(3-15 membered heterocyclyl), —(R$^d$)$_m$—(C$_1$-C$_6$ perfluoroalkyl), —(R$^d$)$_m$-halide, —(R$^d$)$_m$—CN, —(R$^d$)$_m$—C(O)R$^a$, —(R$^d$)$_m$—C(O)OR$^a$, —(R$^d$)$_m$—C(O)NR$^a$R$^b$, —(R$^d$)$_m$—OR$^a$, —(R$^d$)$_m$—OC(O)R$^a$, —(R$^d$)$_m$—OC(O)NR$^a$R$^b$, —(R$^d$)$_m$—O—S(O)R$^a$, —(R$^d$)$_m$—OS(O)$_2$R$^a$, —(R$^d$)$_m$—OS(O)$_2$NR$^a$R$^b$, —(R$^d$)$_m$—OS(O)NR$^a$R$^b$, —(R$^d$)$_m$—NO$_2$, —(R$^d$)$_m$—NR$^a$R$^b$, —(R$^d$)$_m$—N(R$^a$)C(O)R$^b$, —(R$^d$)$_m$—N(R$^a$)C(O)OR$^b$, —(R$^d$)$_m$—N(R$^c$)C(O)NR$^a$R$^b$, —(R$^d$)$_m$—N(R$^a$)S(O)$_2$R$^b$, —(R$^d$)$_m$—N(R$^a$)S(O)R$^b$, —(R$^d$)$_m$—SR$^a$, —(R$^d$)$_m$—S(O)R$^a$, —(R$^d$)$_m$—S(O)$_2$R$^a$, —(R$^d$)$_m$—S(O)NR$^a$R$^b$, —(R$^d$)$_m$—S(O)$_2$NR$^a$R$^b$, —(R$^d$)$_m$—O—(R$^e$)$_m$—NR$^a$R$^b$ or —(R$^d$)$_m$—NR$^a$—(R$^e$)—OR$^b$, or R$^4$ and R$^5$ may together cyclize to form a 3- to- 5-membered spirocycloalkyl; wherein any of the said C$_3$-C$_{12}$ cycloalkyl, aryl, heterocyclyl, or heteroaryl are independently optionally further substituted by 0 to 3 R$_9$ groups;

R$^6$ is selected from R$^a$—O—R$^b$, C$_1$-C$_8$ alkyl, C$_2$-C$_8$ alkenyl, C$_2$-C$_8$ alkynyl, —(R$^d$)$_m$—(C$_3$-C$_{12}$ cycloalkyl), —(R$^d$)$_m$-aryl, —(R$^d$)$_m$-(3-15 membered heterocyclyl), —(R$^d$)$_m$—(C$_1$-C$_6$ perfluoroalkyl), —(R$^d$)$_m$-halide, —(R$^d$)$_m$—CN, —(R$^d$)$_m$—C(O)R$^a$, —(R$^d$)$_m$—C(O)OR$^a$, —(R$^d$)$_m$—C(O)NR$^a$R$^b$, —(R)$_m$—OR$^a$, —(R$^d$)$_m$—OC(O)R$^a$, —(R$^d$)$_m$—OC(O)NR$^a$R$^b$, —(R$^d$)$_m$—O—S(O)R$^a$, —(R$^d$)$_m$—OS(O)$_2$R$^a$, —(R$^d$)$_m$—OS(O)$_2$NR$^a$R$^b$, —(R)$_m$—OS(O)NR$^a$R$^b$, —(R$^d$)$_m$—NO$_2$, —(R$^d$)$_m$—NR$^a$R$^b$, —(R$^d$)$_m$—N(R$^a$)C(O)R$^b$, —(R$^d$)$_m$—N(R$^a$)C(O)OR$^b$, —(R$^d$)$_m$—N(R$^c$)C(O)NR$^a$R$^b$, —(R$^d$)$_m$—N(R$^a$)S(O)$_2$R$^b$, —(R$^d$)$_m$—N(R$^a$)S(O)R$^b$, —(R$^d$)$_m$—SR$^a$, —(R$^d$)$_m$—S(O)R$^a$, —(R$^d$)$_m$—S(O)$_2$R$^a$, —(R$^d$)$_m$—S(O)NR$^a$R$^b$, —(R$^d$)$_m$—S(O)$_2$NR$^a$R$^b$, —(R$^d$)$_m$—O—(R$^e$)$_m$—NR$^a$R$^b$ or —(R$^d$)$_m$—NR$^a$—(R$^e$)—OR$^b$; or R$^6$ may together with R$^4$ cyclize to form a 4- to 7-membered heterocyclyl ring fused to the piperazine or piperadine to which they are attached; and wherein any of the said alkyl, alkenyl, alkynyl, cycloalkyl, aryl, heterocyclyl, and heteroaryl may independently be further substituted with 0 to 3 R$^9$ groups;

each R$^7$ and R$^8$ is independently C$_1$-C$_2$ alkyl, or R$^7$ and R$^8$ together cyclize to form a cyclopropyl or cyclobutyl;

each R$^9$ is independently selected from H, R$^a$—O—R$^b$, C$_1$-C$_8$ alkyl, C$_2$-C$_8$ alkenyl, C$_2$-C$_8$ alkynyl, —(R$^d$)$_m$—(C$_3$-C$_{12}$ cycloalkyl), —(R$^d$)$_m$-aryl, —(R$^d$)$_m$-(3-15 membered heterocyclyl), —(R$^d$)$_m$—(C$_1$-C$_6$ perfluoroalkyl), —(R$^d$)$_m$-halide, —(R$^d$)$_m$—CN, —(R$^d$)$_m$—C(O)R$^a$, —(R$^d$)$_m$—C(O)OR$^a$, —(R$^d$)$_m$—C(O)NR$^a$R$^b$, —(R$^d$)$_m$—OR$^a$, —(R$^d$)$_m$—OC(O)R$^a$, —(R$^d$)$_m$—OC(O)NR$^a$R$^b$, —(R$^d$)$_m$—O—S(O)R$^a$, —(R$^d$)$_m$—OS(O)$_2$R$^a$, —(R$^d$)$_m$—OS(O)$_2$NR$^a$R$^b$, —(R$^d$)$_m$—OS(O)NR$^a$R$^b$, —(R$^d$)$_m$—NO$_2$, —(R$^d$)$_m$—NR$^a$R$^b$, —(R$^d$)$_m$—N(R$^a$)C(O)R$^b$, —(R$^d$)$_m$—N(R$^a$)C(O)OR$^b$, —(R$^d$)$_m$—N(R$^c$)C(O)NR$^a$R$^b$, —(R$^d$)$_m$—N(R$^a$)S(O)$_2$R$^b$, —(R$^d$)$_m$—N(R$^a$)S(O)R$^b$, —(R$^d$)$_m$—SR$^a$, —(R$^d$)$_m$—S(O)R$^a$, —(R$^d$)$_m$—S(O)$_2$R$^a$, —(R$^d$)$_m$—S(O)NR$^a$R$^b$, —(R$^d$)$_m$—S(O)$_2$NR$^a$R$^b$, —(R$^d$)$_m$—O—(R$^e$)$_m$—NR$^a$R$^b$ or —(R$^d$)$_m$—NR$^a$—(R$^e$)—OR$^b$; and wherein any of the said alkyl, alkenyl, alkynyl, R$^d$, R$^e$, C$_3$-C$_{12}$ cycloalkyl, aryl or 3-15 membered heterocyclyl are independently optionally further substituted by 1-3 groups selected from -halide, C$_1$-C$_6$ alkyl, C$_1$-C$_6$ perfluoroalkyl, C$_1$-C$_6$alkoxyl, C$_1$-C$_6$alkylamino, CN or oxo;

each R$^a$, R$^b$ and R$^c$ is independently selected from H, C$_1$-C$_6$perfluoroalkyl, C$_1$-C$_8$ alkyl, C$_2$-C$_8$ alkenyl, —(C$_1$-C$_3$ alkylene)$_m$-(C$_3$-C$_8$ cycloalkyl), —(C$_1$-C$_3$ alkylene)$_m$-(C$_3$-C$_8$ cycloalkenyl), C$_2$-C$_8$ alkynyl, —(C$_1$-C$_3$ alkylene)$_m$-aryl, or —(C$_1$-C$_3$ alkylene)$_m$-(3-8 member heterocyclyl), and each R$^a$, R$^b$ and R$^c$ is independently optionally further substituted by 0 to 3 groups selected from halide, hydroxyl, —CN, C$_1$-C$_6$ alkyl, C$_1$-C$_6$ perfluoroalkyl, C$_1$-C$_6$ alkoxyl and C$_1$-C$_6$ alkylamino; or, when connected to the same nitrogen, R$^a$ and R$^b$ may optionally form a -(3-8 membered heterocyclyl), and said 3-8 membered heterocyclyl is optionally further substituted by 0 to 3 groups selected from halide, hydroxyl, —CN, C$_1$-C$_6$ alkyl, C$_1$-C$_6$ perfluoroalkyl, C$_1$-C$_6$ alkoxyl or C$_1$-C$_6$ alkylamino;

each R$^d$ and R$^e$ is independently —(C$_1$-C$_3$ alkylene)-, —(C$_2$-C$_5$ alkenylene)-, or —(C$_2$-C$_5$ alkynylene)-;

each m is independently 0 or 1; and with the proviso that if X=N, then R$^2$, R$^3$, R$^4$ and R$^5$ are not all H.

Another embodiment provides the method of treating lupus, wherein R$^7$ and R$^8$ are both methyl. Another embodiment provides the method of treating lupus, wherein X is N. Another embodiment provides the method of treating lupus, wherein R$^1$ is a pyridine or a piperazine. Another embodiment provides the method of treating lupus, wherein R$^1$ is a 5-membered heterocyclyl. Another embodiment provides the method of treating lupus, wherein R$^1$ is selected from the group consisting of oxazole, isoxazole, thiazole or imidazole. Another embodiment provides the method of treating lupus, wherein R$^2$ or R$^4$ is methyl. Another embodiment provides the method of treating lupus, wherein R$^6$ is —(R$^d$)$_m$- (3-15 membered heterocyclyl). Another embodiment provides the method of treating lupus, wherein R$^6$ is —(R$^d$)$_m$tetrahydropyran. Another embodiment provides the method of treating lupus, wherein R$^6$ is tetrahydro-2H-pyran-4-ylmethyl. Another embodiment provides the method of treating lupus 1, wherein R$^2$ is —CH$_3$ in (S) configuration. Another embodiment provides the method of treating lupus, wherein R$^6$ is —(R$^d$)$_m$—OR$^a$.

One embodiment provides a method of treating lupus in a subject in need thereof comprising administering to the subject a composition comprising a compound, or a pharmaceutically acceptable salt thereof, selected from the group consisting of:

N-(5-((2R,5S)-2,5-dimethyl-1-((tetrahydro-2H-pyran-4-yl)methyl)piperazine-4-carbonyl)-6,6-dimethyl-1,4,5,6-tetrahydropyrrolo[3,4-c]pyrazol-3-yl)picolinamide;

N-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)-5-fluoropyridine-2-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-5-ethylisoxazole-3-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-2,4-dimethyl-1,3-oxazole-5-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-2-methyl-1,3-thiazole-4-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-2-ethyl-4-methyl-1,3-oxazole-5-carboxamide;

1-cyclobutyl-N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-1H-imidazole-4-carboxamide N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-1-isopropyl-1H-imidazole-4-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-2-ethyl-1,3-oxazole-4-carboxamide;

N-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)-5-morpholin-4-ylpyridine-2-carboxamide; and N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-5-(trifluoromethyl)pyridine-2-carboxamide.

One embodiment provides a method of treating lupus in a subject in need thereof comprising administering to the subject a composition comprising a compound, or a pharmaceutically acceptable salt thereof, having formula (A):

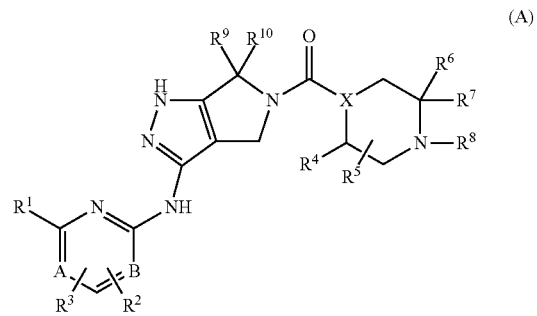

(A)

wherein
X is C—R$^{11}$ or N, wherein R$^{11}$ is H, halo, OH, C$_1$-C$_3$alkyl, CF$_3$, or CN;
A and B are independently C or N;
R$^1$, R$^2$ and R$^3$ are each independently selected from H, R$^a$—O—R$^b$, C$_1$-C$_8$ alkyl, C$_2$-C$_8$ alkenyl, C$_2$-C$_8$ alkynyl, —(R$^d$)$_m$—(C$_3$-C$_{12}$ cycloalkyl), —(R$^d$)$_m$-phenyl, —(R$^d$)$_m$-(3-15 membered heterocyclyl), —(R$^d$)$_m$—(C$_1$-C$_6$ perfluoroalkyl), —(R$^d$)$_m$-halide, —(R$^d$)$_m$—CN, —(R$^d$)$_m$—C(O)R$^a$, —(R$^d$)$_m$—C(O)OR$^a$, —(R$^d$)$_m$—C(O)NR$^a$R$^b$, —(R$^d$)$_m$—OR$^a$, —(R$^d$)$_m$—OC(O)R$^a$, —(R$^d$)$_m$—OC(O)NR$^a$R$^b$, —(R$^d$)$_m$—O—S(O)R$^a$, —(R$^d$)$_m$—OS(O)$_2$R$^a$, —(R$^d$)$_m$—OS(O)$_2$NR$^a$R$^b$, —(R$^d$)$_m$—OS(O)NR$^a$R$^b$, —(R$^d$)$_m$—NO$_2$, —(R$^d$)$_m$—NR$^a$R$^b$, —(R$^d$)$_m$—N(R$^a$)C(O)R$^b$, —(R$^d$)$_m$—N(R$^a$)C(O)OR$^b$, —(R$^d$)$_m$—N(R$^c$)C(O)NR$^a$R$^b$, —(R$^d$)$_m$—N(R$^a$)S(O)$_2$R$^b$, —(R$^d$)$_m$—N(R$^a$)S(O)R$^b$, —(R$^d$)$_m$—SR$^a$, —(R$^d$)$_m$—S(O)R$^a$, —(R$^d$)$_m$—S(O)$_2$R$^a$, —(R$^d$)$_m$—S(O)NR$^a$R$^b$, —(R$^d$)$_m$—S(O)$_2$NR$^a$R$^b$, —(R$^d$)$_m$—O—(R$^e$)$_m$—NR$^a$R$^b$ or —(R$^d$)$_m$—NR$^a$—(R$^e$)—OR$^b$;
wherein R$^2$ and R$^3$ may together optionally cyclize to form a saturated or unsaturated 3-7 membered heterocyclyl fused to the 6-membered N-containing heteroaryl to which they are attached; and wherein any of the said alkyl, alkenyl, alkynyl, R$^a$, R$^b$, R$^c$, R$^d$, R$^e$, C$_3$-C$_{12}$ cycloalkyl, phenyl or 3-15 membered heterocyclyl, may independently be further optionally substituted by 0-3 R$^{12}$ groups;
R$^4$ and R$^5$ are each independently selected from H, R$^a$—O—R$^b$, C$_1$-C$_8$ alkyl, C$_2$-C$_8$ alkenyl, C$_2$-C$_8$ alkynyl, —(R$^d$)$_m$—(C$_3$-C$_{12}$ cycloalkyl), —(R$^d$)$_m$-phenyl, —(R$^d$)$_m$-(3-15 membered heterocyclyl), —(R$^d$)$_m$—(C$_1$-C$_6$ perfluoroalkyl), —(R$^d$)$_m$-halide, —(R$^d$)$_m$—CN, —(R$^d$)$_m$—C(O)R$^a$, —(R$^d$)$_m$—C(O)OR$^a$, —(R$^d$)$_m$—C(O)NR$^a$R$^b$, —(R$^d$)$_m$—OR$^a$, —(R$^d$)$_m$—OC(O)R$^a$, —(R$^d$)$_m$—OC(O)NR$^a$R$^b$, —(R$^d$)$_m$—O—S(O)R$^a$, —(R$^d$)$_m$—OS(O)$_2$R$^a$, —(R$^d$)$_m$—OS(O)$_2$NR$^a$R$^b$, —(R$^d$)$_m$—OS(O)NR$^a$R$^b$, —(R$^d$)$_m$—NO$_2$, —(R$^d$)$_m$—NR$^a$R$^b$, —(R$^d$)$_m$—N(R$^a$)C(O)R$^b$, —(R$^d$)$_m$—N(R$^a$)C(O)OR$^b$, —(R$^d$)$_m$—N(R)C(O)NR$^a$R$^b$, —(R$^d$)$_m$—N(R$^a$)S(O)$_2$R$^b$, —(R$^d$)$_m$—N(R$^a$)S(O)R$^b$, —(R$^d$)$_m$—SR$^a$, —(R$^d$)$_m$—S(O)R$^a$, —(R$^d$)$_m$—S(O)$_2$R$^a$, —(R$^d$)$_m$—S(O)NR$^a$R$^b$, —(R$^d$)$_m$—S(O)$_2$NR$^a$R$^b$, —(R$^d$)$_m$—O—(R$^e$)$_m$—NR$^a$R$^b$ or —(R$^d$)$_m$—NR$^a$—(R$^e$)—OR$^b$;
wherein any of the said alkyl, alkenyl, alkynyl, R$^a$, R$^b$, R$^c$, R$^d$, R$^e$, C$_3$-C$_{12}$ cycloalkyl, aryl or 3-15 membered heterocyclyl are independently optionally further substituted by 0-3 R$^{12}$ groups,
R$^6$ and R$^7$ are each independently H, R$^a$—O—R$^b$, C$_1$-C$_8$ alkyl, C$_2$-C$_8$ alkenyl, C$_2$-C$_8$ alkynyl, —(R$^d$)$_m$—(C$_3$-C$_{12}$ cycloalkyl), —(R$^d$)$_m$-phenyl, —(R$^d$)$_m$-(3-15 membered heterocyclyl), —(R$^d$)$_m$—(C$_1$-C$_6$ perfluoroalkyl), —$(R^d)_m$-halide, —$(R^d)_m$—CN, —$(R^d)_m$—C(O)R$^a$, —$(R^d)_m$—C(O)OR$^a$, —$(R)_m$—C(O)NR$^a$R$^b$, —$(R^d)_m$—OR$^a$, —$(R^d)_m$—OC(O)R$^a$, —$(R^d)_m$—OC(O)NR$^a$R$^b$, —$(R^d)_m$—O—S(O)R$^a$, —$(R^d)_m$—OS(O)$_2$R$^a$, —$(R^d)_m$—OS(O)$_2$NR$^a$R$^b$, —$(R^d)_m$—OS(O)NR$^a$R$^b$, —$(R^d)_m$—NO$_2$, —$(R^d)_m$—N$^a$R$^b$, —$(R^d)_m$—N(R$^a$)C(O)R$^b$, —$(R^d)_m$—N(R$^a$)C(O)OR$^b$, —$(R^d)_m$—N(R$^c$)C(O)NR$^a$R$^b$, —$(R^d)_m$—N(R$^a$)S(O)$_2$R$^b$, —$(R^d)_m$—N(R$^a$)S(O)R$^b$, —$(R^d)_m$—SR$^a$, —$(R^d)_m$—S(O)R$^a$, —$(R^d)_m$—S(O)$_2$R$^a$, —$(R^d)_m$—S(O)NR$^a$R$^b$, —$(R^d)_m$—S(O)$_2$NR$^a$R$^b$, —$(R^d)_m$—O—$(R^e)_m$—NR$^a$R$^b$ or —$(R^d)_m$—NR$^a$—$(R^e)$—OR$^b$; wherein R$^6$ and R$^7$ may together optionally cyclize to form a C$_3$-C$_7$ cycloalkyl and wherein any of the said alkyl, alkenyl, alkynyl, R$^a$, R$^b$, R$^c$, R$^d$, R$^e$, C$_3$-C$_{12}$ cycloalkyl, aryl or 3-15 membered heterocyclyl are independently optionally further substituted by 0-3 R$^{12}$ groups;

R$^8$ is H, R$^a$—O—R$^b$, C$_1$-C$_8$ alkyl, C$_2$-C$_8$ alkenyl, C$_2$-C$_8$ alkynyl, —$(R^d)_m$—(C$_3$-C$_{12}$ cycloalkyl), —$(R^d)_m$-phenyl, —$(R^d)_m$-(3-15 membered heterocyclyl), —$(R^d)_m$—(C$_1$-C$_6$ perfluoroalkyl), —$(R^d)_m$-halide, —$(R^d)_m$—CN, —$(R^d)_m$—C(O)R$^a$, —$(R^d)_m$—C(O)OR$^a$, —$(R^d)_m$—C(O)NR$^a$R$^b$, —$(R^d)_m$—OR$^a$, —$(R^d)_m$—OC(O)R$^a$, —$(R^d)_m$—OC(O)NR$^a$R$^b$, —$(R^d)_m$—O—S(O)R$^a$, —$(R^d)_m$—OS(O)$_2$R$^a$, —$(R^d)_m$—OS(O)$_2$NR$^a$R$^b$, —$(R^d)_m$—OS(O)NR$^a$R$^b$, —$(R^d)_m$—NO$_2$, —$(R^d)_m$—N$^a$R$^b$, —$(R^d)_m$—N(R$^a$)C(O)R$^b$, —$(R^d)_m$—N(R$^a$)C(O)OR$^b$, —$(R^d)_m$—N(R$^c$)C(O)NR$^a$R$^b$, —$(R^d)_m$—N(R$^a$)S(O)$_2$R$^b$, —$(R^d)_m$—N(R$^a$)S(O)R$^b$, —$(R^d)_m$—SR$^a$, —$(R^d)_m$—S(O)R$^a$, —$(R^d)_m$—S(O)$_2$R$^a$, —$(R^d)_m$—S(O)NR$^a$R$^b$, —$(R^d)_m$—S(O)$_2$NR$^a$R$^b$, —$(R^d)_m$—O—$(R^e)_m$—NR$^a$R$^b$ or —$(R^d)_m$—NR$^a$—$(R^e)$—OR$^b$; and wherein any of the said alkyl, alkenyl, alkynyl, R$^a$, R$^b$, R$^c$, R$^d$, R$^e$, C$_3$-C$_{12}$ cycloalkyl, phenyl, or 3-15 membered heterocyclyl are independently optionally further substituted by 1-3 groups selected from —F, C$_1$-C$_3$ alkyl, C$_1$-C$_3$ perfluoroalkyl, hydroxyl, C$_1$-C$_6$alkoxyl, or oxo;

R$^9$ and R$^{10}$ are each independently C$_1$-C$_2$ alkyl or can together cyclize to form a cyclopropyl or cyclobutyl;

each R$^{12}$ is independently H, R$^a$—O—R$^b$, C$_1$-C$_8$ alkyl, C$_2$-C$_8$ alkenyl, C$_2$-C$_8$ alkynyl, —$(R^d)_m$—(C$_3$-C$_{12}$ cycloalkyl), —$(R^d)_m$-phenyl, —$(R^d)_m$-(3-15 membered heterocyclyl), —$(R^d)_m$—(C$_1$-C$_6$ perfluoroalkyl), —$(R^d)_m$-halide, —$(R^d)_m$—CN, —$(R^d)_m$—C(O)R$^a$, —$(R^d)_m$—C(O)OR$^a$, —$(R^d)_m$—C(O)NR$^a$R$^b$, —$(R^d)_m$—OR$^a$, —$(R^d)_m$—OC(O)R$^a$, —$(R^d)_m$—OC(O)NR$^a$R$^b$, —$(R^d)_m$—O—S(O)R$^a$, —$(R^d)_m$—OS(O)$_2$R$^a$, —$(R^d)_m$—OS(O)$_2$NR$^a$R$^b$, —$(R^d)_m$—OS(O)NR$^a$R$^b$, —$(R^d)_m$—NO$_2$, —$(R^d)_m$—N$^a$R$^b$, —$(R^d)_m$—N(R$^a$)C(O)R$^b$, —$(R^d)_m$—N(R$^a$)C(O)OR$^b$, —$(R^d)_m$—N(R$^c$)C(O)NR$^a$R$^b$, —$(R^d)_m$—N(R$^a$)S(O)$_2$R$^b$, —$(R^d)_m$—N(R$^a$)S(O)R$^b$, —$(R^d)_m$—SR$^a$, —$(R^d)_m$—S(O)R$^a$, —$(R^d)_m$—S(O)$_2$R$^a$, —$(R^d)_m$—S(O)NR$^a$R$^b$, —$(R^d)_m$—S(O)$_2$NR$^a$R$^b$, —$(R^d)_m$—O—$(R^e)_m$—NR$^a$R$^b$ or —$(R^d)_m$—NR$^a$—$(R^e)$—OR$^b$; and wherein any of the said alkyl, alkenyl, alkynyl, R$^a$, R$^b$, R$^c$, R$^d$, R$^e$, C$_3$-C$_{12}$ cycloalkyl, phenyl, or 3-15 membered heterocyclyl, are independently optionally further substituted by 1-3 groups selected from —F, C$_1$-C$_3$ alkyl, C$_1$-C$_3$ perfluoroalkyl, hydroxyl, C$_1$-C$_6$alkoxyl or oxo;

each R$^a$, R$^b$ and R$^c$ is independently selected from H, C$_1$-C$_8$ alkyl, C$_2$-C$_8$ alkenyl, —$(R^d)_m$—(C$_3$-C$_8$ cycloalkyl), —$(R^d)_m$—(C$_3$-C$_8$ cycloalkenyl), C$_2$-C$_8$ alkynyl, —$(R^d)_m$-phenyl, or —$(R^d)_m$-(3-7 membered heterocyclyl), and each R$^a$, R$^b$ and R$^c$ is independently optionally further substituted by 1-3 groups selected from halide, hydroxyl, —CN, C$_1$-C$_6$ alkyl, C$_1$-C$_6$ perfluoroalkyl, C$_1$-C$_6$ alkoxyl and C$_1$-C$_6$ alkylamino; or, when connected to the same nitrogen, R$^a$ and R$^b$ may together optionally form a 3-7 membered heterocyclyl, which may optionally be further substituted by 0-3 groups selected from halide, hydroxyl, —CN, C$_1$-C$_6$ alkyl, C$_1$-C$_6$ perfluoroalkyl, C$_1$-C$_6$ alkoxyl or C$_1$-C$_6$ alkylamino;

each R$^d$ and R$^e$ is independently-(C$_1$-C$_3$ alkylene)-, —(C$_2$-C$_5$ alkenylene)-, or —(C$_2$-C$_5$ alkynylene)-;

and each m is independently 0 or 1;

with the proviso that when X is N, R$^6$ and R$^7$ are not both H, and that when X is C—R$^{11}$, R$^6$ and R$^7$ are both H;

or a pharmaceutically acceptable salt thereof.

Another embodiment provides a method of treating lupus, wherein for the compound of Formula (A), R$^9$ and R$^{10}$ are both methyl. Another embodiment provides a method of treating lupus, wherein for the compound of Formula (A), X is N and R$^6$ and R$^7$ are each independently H or C$_1$-C$_6$alkyl but are not both H. Another embodiment provides a method of treating lupus, wherein for the compound of Formula (A), A is N and B is C. Another embodiment provides a method of treating lupus, wherein for the compound of Formula (A), A is C and B is N. Another embodiment provides a method of treating lupus, wherein for the compound of Formula (A), R$^6$ and R$^7$ are both methyl. Another embodiment provides a method of treating lupus, wherein for the compound of Formula (A), R$^6$ is H and R$^7$ is methyl. Another embodiment provides a method of treating lupus, wherein for the compound of Formula (A), R$^4$ is R$^a$—O—R$^b$, C$_1$-C$_8$ alkyl, C$_2$-C$_8$ alkenyl, C$_2$-C$_8$ alkynyl, —$(R^d)_m$—(C$_3$-C$_{12}$cycloalkyl), —$(R^d)_m$-phenyl, —$(R^d)_m$-(3-15 membered heterocyclyl), —$(R^d)_m$—(C$_1$-C$_6$perfluoroalkyl), —$(R^d)_m$-halide, —$(R^d)_m$—CN, —$(R^d)_m$—C(O)R$^a$, —$(R^d)_m$—C(O)OR$^a$, —$(R^d)_m$—C(O)NR$^a$R$^b$, —$(R^d)_m$—OR$^a$, —$(R^d)_m$—C(O)R$^a$, —$(R^d)_m$—OC(O)NR$^a$R$^b$, —$(R^d)_m$—O—S(O)R$^a$, —$(R^d)_m$—OS(O)$_2$R$^a$, —$(R^d)_m$—OS(O)$_2$NR$^a$R$^b$, —$(R^d)_m$—OS(O)NR$^a$R$^b$, —$(R^d)_m$—NO$_2$, —$(R^d)_m$—NR$^a$R$^b$, —$(R^d)_m$—N(R$^a$)C(O)R$^b$, —$(R^d)_m$—N(R$^a$)C(O)OR$^b$, —$(R^d)_m$—N(R$^c$)C(O)NR$^a$R$^b$, —$(R^d)_m$—N(R$^a$)S(O)$_2$R$^b$, —$(R^d)_m$—N(R$^a$)S(O)R$^b$, —$(R^d)_m$—SR$^a$, —$(R^d)_m$—S(O)R$^a$, —$(R^d)_m$—S(O)$_2$R$^a$, —$(R^d)_m$—S(O)NR$^a$R$^b$, —$(R^d)_m$—S(O)$_2$NR$^a$R$^b$, —$(R^d)_m$—O—$(R^e)_m$—NR$^a$R$^b$ or —$(R^d)_m$—NR$^a$—$(R^e)$—OR$^b$; wherein the said R$^a$, R$^b$, R$^c$, R$^d$, R$^e$, C$_3$-C$_{12}$ cycloalkyl, aryl, 3-15 membered heterocyclyl, are independently optionally further substituted by 0-3 R$^{12}$ groups.

Another embodiment provides a method of treating lupus, wherein for the compound of Formula (A), R$^4$ is methyl. Another embodiment provides a method of treating lupus, wherein for the compound of Formula (A), R$^1$ is R$^a$—O—R$^b$, C$_1$-C$_8$ alkyl, C$_2$-C$_8$ alkenyl, C$_2$-C$_8$ alkynyl, —$(R^d)_m$—(C$_3$-C$_{12}$ cycloalkyl), —$(R^d)_m$-phenyl, —$(R^d)_m$-(3-15 membered heterocyclyl), —$(R^d)_m$—(C$_1$-C$_6$ perfluoroalkyl), —$(R^d)_m$-halide, —$(R^d)_m$—CN, —$(R^d)_m$—C(O)R$^a$, —$(R^d)_m$—C(O)OR$^a$, —$(R^d)_m$—C(O)NR$^a$R$^b$, —$(R^d)_m$—OR$^a$, —$(R^d)_m$—OC(O)R$^a$, —$(R^d)_m$—OC(O)NR$^a$R$^b$, —$(R^d)_m$—O—S(O)R$^a$, —$(R^d)_m$—OS(O)$_2$R$^a$, —$(R^d)_m$—OS(O)$_2$NR$^a$R$^b$, —$(R^d)_m$—OS(O)NR$^a$R$^b$, —$(R^d)_m$—NO$_2$, —$(R^d)_m$—NR$^a$R$^b$, —$(R^d)_m$—N(R$^a$)C(O)R$^b$, —$(R^d)_m$—N(R$^a$)C(O)OR$^b$, —$(R^d)_m$—N(R$^c$)C(O)NR$^a$R$^b$, —$(R^d)_m$—N(R$^a$)S(O)$_2$R$^b$, —$(R^d)_m$—N(R$^a$)S(O)R$^b$, —$(R^d)_m$—SR$^a$, —$(R^d)_m$—S(O)R$^a$, —$(R^d)_m$—S(O)$_2$R$^a$, —$(R^d)_m$—S(O)NR$^a$R$^b$, —$(R^d)_m$—S(O)$_2$NR$^a$R$^b$, —$(R^d)_m$—O—$(R^e)_m$—NR$^a$R$^b$ or —$(R^d)_m$—NR$^a$—$(R^e)$—OR$^b$; wherein the said —R$^a$, R$^b$, R$^c$, R$^d$, R$^e$, C$_3$-C$_{12}$ cycloalkyl, aryl, the said 3-15 membered heterocyclyl, are independently optionally further substituted by 0-3 R$^{12}$ groups.

Another embodiment provides a method of treating lupus, wherein for the compound of Formula (A), $R^1$ is —$(R^d)_m$—$OR^a$, $C_1$-$C_8$ alkyl, or —$(R^d)_m$—$NR^aR^b$. Another embodiment provides a method of treating lupus, wherein for the compound of Formula (A), $R^8$ is $R^a$—O—$R^b$, $C_1$-$C_8$ alkyl, $C_2$-$C_8$ alkenyl, $C_2$-$C_8$ alkynyl, —$(R^d)_m$—($C_3$-$C_{12}$ cycloalkyl), —$(R^d)_m$-phenyl, —$(R^d)_m$-(3-15 membered heterocyclyl), —$(R^d)_m$—($C_1$-$C_6$ perfluoroalkyl), —$(R^d)_m$-halide, —$(R^d)_m$—CN, —$(R^d)_m$—$OR^a$, or —$(R^d)_m$—$NR^aR^b$. Another embodiment provides a method of treating lupus, wherein for the compound of Formula (A), each $R^d$ and $R^e$ is independently an —($C_1$-$C_3$ alkylene).

One embodiment provides a method of treating lupus in a subject in need thereof comprising administering to the subject a composition comprising a compound, or a pharmaceutically acceptable salt thereof, having formula (B):

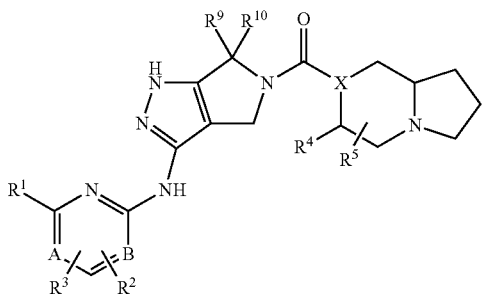

(B)

wherein

X is C—$R^{11}$ or N, wherein $R^{11}$ is H, halo, OH, $C_1$-$C_3$alkyl, $CF_3$, or CN;

A and B are independently C or N;

$R^1$ is $R^a$—O—$R^b$, $C_1$-$C_8$ alkyl, $C_2$-$C_8$ alkenyl, $C_2$-$C_8$ alkynyl, —$(R^d)_m$—($C_3$-$C_{12}$ cycloalkyl), —$(R^d)_m$-phenyl, —$(R^d)_m$-(3-15 membered heterocyclyl), —$(R^d)_m$—($C_1$-$C_6$ perfluoroalkyl), —$(R^d)_m$-halide, —$(R^d)_m$—CN, —$(R^d)_m$—C(O)$R^a$, —$(R^d)_m$—C(O)O$R^a$, —$(R^d)_m$—C(O)N$R^aR^b$, —$(R^d)_m$—O$R^a$, —$(R^d)_m$—OC(O)$R^a$, —$(R^d)_m$—OC(O)N$R^aR^b$, —$(R^d)_m$—O—S(O)$R^a$, —$(R^d)_m$—OS(O)$_2R^a$, —$(R^d)_m$—OS(O)$_2$N$R^aR^b$, —$(R^d)_m$—OS(O)N$R^aR^b$, —$(R^d)_m$—NO$_2$, —$(R^d)_m$—N$R^aR^b$, —$(R^d)_m$—N($R^a$)C(O)$R^b$, —$(R^d)_m$—N($R^a$)C(O)O$R^b$, —$(R^d)_m$—N($R^c$)C(O)N$R^aR^b$, —$(R^d)_m$—N($R^a$)S(O)$_2R^b$, —$(R^d)_m$—N($R^a$)S(O)$R^b$, —$(R^d)_m$—S$R^a$, —$(R^d)_m$—S(O)$R^a$, —$(R^d)_m$—S(O)$_2R^a$, —$(R^d)_m$—S(O)N$R^aR^b$, —$(R^d)_m$—S(O)$_2$N$R^aR^b$, —$(R^d)_m$—O—$(R^e)_m$—N$R^aR^b$ or —$(R^d)_m$—N$R^a$—$(R^e)$—O$R^b$; and wherein any of the said alkyl, alkenyl, alkynyl, $R^a$, $R^b$, $R^c$, $R^d$, $R^e$, $C_3$-$C_{12}$ cycloalkyl, phenyl or 3-15 membered heterocyclyl, may independently be further optionally substituted by 0-3 $R^{12}$ groups;

$R^2$ and $R^3$ are each independently selected from H, $R^a$—O—$R^b$, $C_1$-$C_8$ alkyl, $C_2$-$C_8$ alkenyl, $C_2$-$C_8$ alkynyl, —$(R^d)_m$—($C_3$-$C_{12}$ cycloalkyl), —$(R^d)_m$-phenyl, —$(R^d)_m$-(3-15 membered heterocyclyl), —$(R^d)_m$—($C_1$-$C_6$ perfluoroalkyl), —$(R^d)_m$-halide, —$(R^d)_m$—CN, —$(R^d)_m$—C(O)$R^a$, —$(R^d)_m$—C(O)O$R^a$, —$(R^d)_m$—C(O)N$R^aR^b$, —$(R^d)_m$—O$R^a$, —$(R^d)_m$—OC(O)$R^a$, —$(R^d)_m$—OC(O)N$R^aR^b$, —$(R^d)_m$—O—S(O)$R^a$, —$(R^d)_m$—OS(O)$_2R^a$, —$(R^d)_m$—OS(O)$_2$N$R^aR^b$, —$(R^d)_m$—OS(O)N$R^aR^b$, —$(R^d)_m$—NO$_2$, —$(R^d)_m$—N$R^aR^b$, —$(R^d)_m$—N($R^a$)C(O)$R^b$, —$(R^d)_m$—N($R^a$)C(O)O$R^b$, —$(R^d)_m$—N($R^c$)C(O)N$R^aR^b$, —$(R^d)_m$—N($R^a$)S(O)$_2R^b$, —$(R^d)_m$—N($R^a$)S(O)$R^b$, —$(R^d)_m$—S$R^a$, —$(R^d)_m$—S(O)$R^a$, —$(R^d)_m$—S(O)$_2R^a$, —$(R^d)_m$—S(O)N$R^aR^b$, —$(R^d)_m$—S(O)$_2$N$R^aR^b$, —$(R^d)_m$—O—$(R^e)_m$—N$R^aR^b$ or —$(R^d)_m$—N$R^a$—$(R^e)$—O$R^b$;

wherein $R^2$ and $R^3$ may together optionally cyclize to form a saturated or unsaturated 3-7 membered heterocyclyl fused to the 6-membered N-containing heteroaryl to which they are attached; and wherein any of the said alkyl, alkenyl, alkynyl, $R^a$, $R^b$, $R^c$, $R^d$, $R^e$, $C_3$-$C_{12}$ cycloalkyl, phenyl or 3-15 membered heterocyclyl, may independently be further optionally substituted by 0-3 $R^{12}$ groups;

$R^4$ and $R^5$ are each independently selected from H, $R^a$—O—$R^b$, $C_1$-$C_8$ alkyl, $C_2$-$C_8$ alkenyl, $C_2$-$C_8$ alkynyl, —$(R^d)_m$—($C_3$-$C_{12}$ cycloalkyl), —$(R^d)_m$-phenyl, —$(R^d)_m$-(3-15 membered heterocyclyl), —$(R^d)_m$—($C_1$-$C_6$ perfluoroalkyl), —$(R^d)_m$-halide, —$(R^d)_m$—CN, —$(R^d)_m$—C(O)$R^a$, —$(R^d)_m$—C(O)O$R^a$, —$(R^d)_m$—C(O)N$R^aR^b$, —$(R^d)_m$—O$R^a$, —$(R^d)_m$—OC(O)$R^a$, —$(R^d)_m$—OC(O)N$R^aR^b$, —$(R^d)_m$—O—S(O)$R^a$, —$(R^d)_m$—OS(O)$_2R^a$, —$(R^d)_m$—OS(O)$_2$N$R^aR^b$, —$(R^d)_m$—OS(O)N$R^aR^b$, —$(R^d)_m$—NO$_2$, —$(R^d)_m$—N$R^aR^b$, —$(R^d)_m$—N($R^a$)C(O)$R^b$, —$(R^d)_m$—N($R^a$)C(O)O$R^b$, —$(R^d)_m$—N($R^c$)C(O)N$R^aR^b$, —$(R^d)_m$—N($R^a$)S(O)$_2R^b$, —$(R^d)_m$—N($R^a$)S(O)$R^b$, —$(R^d)_m$—S$R^a$, —$(R^d)_m$—S(O)$R^a$, —$(R^d)_m$—S(O)$_2R^a$, —$(R^d)_m$—S(O)N$R^aR^b$, —$(R^d)_m$—S(O)$_2$N$R^aR^b$, —$(R^d)_m$—O—$(R^e)_m$—N$R^aR^b$ or —$(R^d)_m$—N$R^a$—$(R^e)$—O$R^b$;

wherein any of the said alkyl, alkenyl, alkynyl, $R^a$, $R^b$, $R^c$, $R^d$, $R^e$, $C_3$-$C_{12}$ cycloalkyl, aryl or 3-15 membered heterocyclyl are independently optionally further substituted by 0-3 $R^{12}$ groups, $R^8$ is H, $R^a$—O—$R^b$, $C_1$-$C_8$ alkyl, $C_2$-$C_8$ alkenyl, $C_2$-$C_8$ alkynyl, —$(R^d)_m$—($C_3$-$C_{12}$ cycloalkyl), —$(R^d)_m$-phenyl, —$(R^d)_m$-(3-15 membered heterocyclyl), —$(R^d)_m$—($C_1$-$C_6$ perfluoroalkyl), —$(R^d)_m$-halide, —$(R^d)_m$—CN, —$(R^d)_m$—C(O)$R^a$, —$(R^d)_m$—C(O)O$R^a$, —$(R^d)_m$—C(O)N$R^aR^b$, —$(R^d)_m$—O$R^a$, —$(R^d)_m$—OC(O)$R^a$, —$(R^d)_m$—OC(O)N$R^aR^b$, —$(R^d)_m$—O—S(O)$R^a$, —$(R^d)_m$—OS(O)$_2R^a$, —$(R^d)_m$—OS(O)$_2$N$R^aR^b$, —$(R^d)_m$—OS(O)N$R^aR^b$, —$(R^d)_m$—NO$_2$, —$(R^d)_m$—N$R^aR^b$, —$(R^d)_m$—N($R^a$)C(O)$R^b$, —$(R^d)_m$—N($R^a$)C(O)O$R^b$, —$(R^d)_m$—N($R^c$)C(O)N$R^aR^b$, —$(R^d)_m$—N($R^a$)S(O)$_2R^b$, —$(R^d)_m$—N($R^a$)S(O)$R^b$, —$(R^d)_m$—S$R^a$, —$(R^d)_m$—S(O)$R^a$, —$(R^d)_m$—S(O)$_2R^a$, —$(R^d)_m$—S(O)N$R^aR^b$, —$(R^d)_m$—S(O)$_2$N$R^aR^b$, —$(R^d)_m$—O—$(R^e)_m$—N$R^aR^b$ or —$(R^d)_m$—N$R^a$—$(R^e)$—O$R^b$; and wherein any of the said alkyl, alkenyl, alkynyl, $R^a$, $R^b$, $R^c$, $R^d$, $R^e$, $C_3$-$C_{12}$ cycloalkyl, phenyl, or 3-15 membered heterocyclyl are independently optionally further substituted by 1-3 groups selected from —F, $C_1$-$C_3$ alkyl, $C_1$-$C_3$ perfluoroalkyl, hydroxyl, $C_1$-$C_6$alkoxyl, or oxo;

$R^9$ and $R^{10}$ are each independently $C_1$-$C_2$ alkyl or can together cyclize to form a cyclopropyl or cyclobutyl;

each $R^{12}$ is independently H, $R^a$—O—$R^b$, $C_1$-$C_8$ alkyl, $C_2$-$C_8$ alkenyl, $C_2$-$C_8$ alkynyl, —$(R^d)_m$—($C_3$-$C_{12}$ cycloalkyl), —$(R^d)_m$-phenyl, —$(R^d)_m$-(3-15 membered heterocyclyl), —$(R^d)_m$—($C_1$-$C_6$ perfluoroalkyl), —$(R^d)_m$-halide, —$(R^d)_m$—CN, —$(R^d)_m$—C(O)$R^a$, —$(R^d)_m$—C(O)O$R^a$, —$(R^d)_m$—C(O)N$R^aR^b$, —$(R^d)_m$—O$R^a$, —$(R^d)_m$—OC(O)$R^a$, —$(R^d)_m$—OC(O)N$R^aR^b$, —$(R^d)_m$—O—S(O)$R^a$, —$(R^d)_m$—OS(O)$_2R^a$, —$(R^d)_m$—OS(O)$_2$N$R^aR^b$, —$(R^d)_m$—OS(O)N$R^aR^b$, —$(R^d)_m$—NO$_2$, —$(R^d)_m$—N$R^aR^b$, —$(R^d)_m$—N($R^a$)C(O)$R^b$, —$(R^d)_m$—N($R^a$)C(O)O$R^b$, —$(R^d)_m$—N($R^c$)C(O)

NR$^a$R$^b$, —(R$^d$)$_m$—N(R$^a$)S(O)$_2$R$^b$, —(R$^d$)$_m$—N(R$^a$)S(O)R$^b$, —(R$^d$)$_m$—SR$^a$, —(R$^d$)$_m$—S(O)R$^a$, —(R$^d$)$_m$—S(O)$_2$R$^a$, —(R$^d$)$_m$—S(O)NR$^a$R$^b$, —(R$^d$)$_m$—S(O)$_2$NR$^a$R$^b$, —(R$^d$)$_m$—O—(R$^e$)$_m$—NR$^a$R$^b$ or —(R$^d$)$_m$—NR$^a$—(R$^e$)—OR$^b$; and wherein any of the said alkyl, alkenyl, alkynyl, R$^a$, R$^b$, R$^c$, R$^d$, R$^e$, C$_3$-C$_{12}$ cycloalkyl, phenyl, or 3-15 membered heterocyclyl, are independently optionally further substituted by 1-3 groups selected from —F, C$_1$-C$_3$ alkyl, C$_1$-C$_3$ perfluoroalkyl, hydroxyl, C$_1$-C$_6$alkoxyl or oxo;

each R$^a$, R$^b$ and R$^c$ is independently selected from H, C$_1$-C$_8$ alkyl, C$_2$-C$_8$ alkenyl, —(R$^d$)$_m$—(C$_3$-C$_8$ cycloalkyl), —(R$^d$)$_m$—(C$_3$-C$_8$ cycloalkenyl), C$_2$—C alkynyl, —(R$^d$)$_m$-phenyl, or —(R$^d$)$_m$-(3-7 membered heterocyclyl), and each R$^a$, R$^b$ and R$^c$ is independently optionally further substituted by 1-3 groups selected from halide, hydroxyl, —CN, C$_1$-C$_6$ alkyl, C$_1$-C$_6$ perfluoroalkyl, C$_1$-C$_6$ alkoxyl and C$_1$-C$_6$ alkylamino; or, when connected to the same nitrogen, R$^a$ and R$^b$ may together optionally form a 3-7 membered heterocyclyl, which may optionally be further substituted by 0-3 groups selected from halide, hydroxyl, —CN, C$_1$-C$_6$ alkyl, C$_1$-C$_6$ perfluoroalkyl, C$_1$-C$_6$ alkoxyl or C$_1$-C$_6$ alkylamino;

each R$^d$ and R$^e$ is independently-(C$_1$-C$_3$ alkylene)-, —(C$_2$-C$_5$ alkenylene)-, or —(C$_2$-C$_5$ alkynylene)-;

and each m is independently 0 or 1, or a pharmaceutically acceptable salt thereof.

Another embodiment provides a method of treating lupus, wherein for the compound of Formula (B), A is N and B is C. Another embodiment provides a method of treating lupus, wherein for the compound of Formula (B), R$^9$ and R$^{10}$ are both methyl. Another embodiment provides a method of treating lupus, wherein for the compound of Formula (B), R$^4$ is —(R$^d$)$_m$—OR$^a$, C$_1$-C$_8$ alkyl, C$_2$-C$_8$ alkenyl or C$_2$-C$_8$ alkynyl. Another embodiment provides a method of treating lupus, wherein for the compound of Formula (B), R$^4$ is methyl. Another embodiment provides a method of treating lupus, wherein for the compound of Formula (B), R$^1$ is —(R$^d$)$_m$—OR$^a$, C$_1$-C$_8$ alkyl, or —(R$^d$)$_m$—NR$^a$R$^b$. Another embodiment provides a method of treating lupus, wherein for the compound of Formula (B), each R$^d$ and R$^e$ is independently an —(C$_1$-C$_3$ alkylene)-.

Lupus Erythematosus

Disclosed herein is a method of treating lupus (lupus erythematosus, LE) in a subject in need thereof comprising administering to the subject a compound having the formula 5-{[(2S,5R)-2,5-dimethyl-4-(tetrahydro-2H-pyran-4-ylmethyl)piperazin-1-yl]carbonyl)}-N-(5-fluoro-2-methylpyrimidin-4-yl)-6,6-dimethyl-1,4,5,6-tetrahydropyrrolo[3,4-c]pyrazol-3-amine. In some embodiments, lupus is a multisystem autoimmune disease wherein the body's immune system attacks its own tissues and organs including the heart, joints, skin, lungs, blood vessels, liver, kidneys and the nervous system. In some embodiments, lupus is categorized into systemic lupus erythematosus, cutaneous lupus erythematosus and drug-induced lupus erythematosus. In some embodiments, cutaneous LE is further categorized into hypertrophicus LE, tumidus LE, discoid LE, subacute LE, profundus LE, neonatal LE and acute cutaneous LE.

In some embodiments, lupus is a systemic lupus erythematosus (SLE). In some embodiments, SLE is characterized by an abnormal B cell behavior such as decreased threshold for B lymphocyte activation, abnormal clearance of apoptotic cells and immune complexes and production of autoantibodies to self antigen. In some embodiments, PKCβ participates in B cell activation and in B cell-mediated humoral responses. For example, PKCβ$^{-/-}$ mice have defects in antibody production after a challenge with T cell-dependent or T cell-independent antigens (see Leitges, M., et al, "Immunodeficiency in protein kinase Cbeta-deficient mice," *Science* 273: 788-791 (1996)). Further, in a mouse model, deficiency of PKCβ induced an anergic B cell phenotype and preferentially inhibited autoreactive plasma cells and autoantibodies in mice (see Oleksyn D, et al, "PKCβ is required for lupus development in Sle mice," *Arthritis Rheum.* 65:1022-31(2013)). In some embodiments, SLE is a relapsed or refractory SLE.

In some embodiments, SLE is associated with a plurality of clinical manifestations. In some embodiments, the plurality of clinical manifestations include, but are not limited to, malar rash (butterfly rash); discoid lupus; alopecia; mouth, nasal, urinary tract and vaginal ulcers; joint pain; osteoarticular tuberculosis; anemia; antiphospholipid antibody syndrome; pericarditis; myocarditis; endocarditis; atherosclerosis; pleuritis; pleural effusion; lupus pneumonitis, chronic diffuse interstitial lung disease; pulmonary hypertension, pulmonary emboli; pulmonary hemorrhage; shrinking lung syndrome; proteinuria; hematuria; lupus nephritis; membranous glomerulonephritis; neuropsychiatric syndromes (headache, cognitive dysfunction, mood disorder, cerebrovascular disease, seizures, polyneuropathy, anxiety disorder, psychosis, intracranial hypertension syndrome); acute confusional state; Guillain-Barre syndrome; aseptic meningitis; autonomic disorder; demyelinating syndrome; mononeuropathy; movement disorder; myasthenia gravis; myelopathy; cranial neuropathy; plexopathy; or any combinations thereof.

Disclosed herein, in some embodiments, is a method of treating SLE in a subject in need thereof comprising administering to the subject a compound of having the formula 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

Disclosed herein, in some embodiments, is a method of reducing the progression of systemic lupus erythematosus (SLE) or reducing the rate of relapses in SLE in a subject in need thereof comprising administering to the subject a compound having the formula 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine.

Uveitis

One embodiment provides a method of treating uveitis in a subject in need thereof comprising administering to the subject a composition comprising a compound, or a pharmaceutically acceptable salt thereof, selected from the group consisting of:

N$^4$-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-N2-ethyl-5-fluoropyrimidine-2,4-diamine, N$^4$-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-5-fluoro-N$^2$,N$^2$-dimethylpyrimidine-2,4-diamine, N$^2$-cyclopropyl-N4-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-5-fluoropyrimidine-2,4-diamine, N$^4$-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-5-fluoro-N$^2$-methylpyrimidine-2,4-diamine, N$^4$-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-5-fluoro-N$^2$-isopropylpyrimidine-2,4-diamine, N$^4$-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-N$^2$-ethylpyrimidine-2,4-diamine, N$^4$-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-N$^2$,N$^2$-dimethylpyrimidine-2,4-diamine, 5-{[(8S)-6,8-dimethyl-6,9-diazaspiro[4.5]dec-9-yl]carbonyl}-N-(5-fluoro-2-methylpyrimidin-4-yl)-6,6-dimethyl-1,4,5,6-tetrahydropyrrolo[3,4-c]pyrazol-3-amine, N$^4$-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-N$^2$-ethyl-5-fluoropyrimidine-2,4-diamine, N$^4$-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)-N$^2$-ethyl-5-fluoropyrimidine-2,4-diamine, N$^2$-ethyl-5-fluoro-N$^4$-(5-{[(2S,5R)-4-(3-methoxypropyl)-2,5-dimethylpiperazin-1-yl]carbonyl})-6,6-dimethyl-1,4,5,6-tetrahydropyrrolo[3,4-c]pyrazol-3-yl)pyrimidine-2,4-diamine, N$^4$-(6,6-dimethyl-5-{[(2S,5R)-2,4,5-trimethylpiperazin-1-yl]carbonyl}-1,4,5,6-tetrahydropyrrolo[3,4-c]pyrazol-3-yl)-N$^2$-ethyl-5-fluoropyrimidine-2,4-diamine, 4-[(6,6-dimethyl-5-{[(2S,5R)-2,4,5-trimethylpiperazin-1-yl]carbonyl}-1,4,5,6-tetrahydropyrrolo[3,4-c]pyrazol-3-yl)amino]pyrimidine-2-carbonitrile, N-(2-ethyl-5-fluoropyrimidin-4-yl)-6,6-dimethyl-5-{[(2S)-2,4,5,5-tetramethylpiperazin-1-yl]carbonyl})-1,4,5,6-tetrahydropyrrolo[3,4-c]pyrazol-3-amine, N-(2-ethyl-5-fluoropyrimidin-4-yl)-5-{[(2S,5R)-4-(3-methoxypropyl)-2,5-dimethylpiperazin-1-yl]carbonyl}-6,6-dimethyl-1,4,5,6-tetrahydropyrrolo[3,4-c]pyrazol-3-amine, 2-((5S)-4-{[3-[(2-ethyl-5-fluoropyrimidin-4-yl)amino]-6,6-dimethyl-4,6-dihydropyrrolo[3,4-c]pyrazol-5(1H)-yl]carbonyl}-1,5-dimethylpiperazin-2-yl)ethanol, 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, N-(5-fluoro-2-methylpyrimidin-4-yl)-6,6-dimethyl-5-{[(2S)-2,4,5,5-tetramethylpiperazin-1-yl]carbonyl})-1,4,5,6-tetrahydropyrrolo[3,4-c]pyrazol-3-amine, N-(5-fluoro-2-propylpyrimidin-4-yl)-6,6-dimethyl-5-{[(2S)-2,4,5,5-tetramethylpiperazin-1-yl]carbonyl})-1,4,5,6-tetrahydropyrrolo[3,4-c]pyrazol-3-amine, N-(5-fluoro-2-isopropylpyrimidin-4-yl)-6,6-dimethyl-5-{[(2S)-2,4,5,5-tetramethylpiperazin-1-yl]carbonyl})-1,4,5,6-tetrahydropyrrolo[3,4-c]pyrazol-3-amine, N-[5-fluoro-2-(methoxymethyl)pyrimidin-4-yl]-6,6-dimethyl-5-{[(2S)-2,4,5,5-tetramethylpiperazin-1-yl]carbonyl})-1,4,5,6-tetrahydropyrrolo[3,4-c]pyrazol-3-amine, 5-{[(2S,5R)-2,5-dimethyl-4-(tetrahydro-2H-pyran-4-ylmethyl)piperazin-1-yl]carbonyl}-N-(2-ethyl-5-fluoropyrimidin-4-yl)-6,6-dimethyl-1,4,5,6-tetrahydropyrrolo[3,4-c]pyrazol-3-amine, 5-{[(2S,5R)-2,5-dimethyl-4-(tetrahydro-2H-pyran-4-yl)piperazin-1-yl]carbonyl})-N-(4-methoxypyrimidin-2-yl)-6,6-dimethyl-1,4,5,6-tetrahydropyrrolo[3,4-c]pyrazol-3-amine, 5-{[(2S,5R)-2,5-dimethyl-4-(tetrahydro-2H-pyran-4-yl)piperazin-1-yl]carbonyl}-6,6-dimethyl-N-(4-methylpyrimidin-2-yl)-1,4,5,6-tetrahydropyrrolo[3,4-c]pyrazol-3-amine, 5-{[(2S,5R)-2,5-dimethyl-4-(tetrahydro-2H-pyran-4-yl)piperazin-1-yl]carbonyl}-6,6-dimethyl-N-[4-(trifluoromethyl)pyrimidin-2-yl]-1,4,5,6-tetrahydropyrrolo[3,4-c]pyrazol-3-amine, 5-{[(2S,5R)-2,5-dimethyl-4-(tetrahydro-2H-pyran-4-ylmethyl)piperazin-1-yl]carbonyl}-6,6-dimethyl-N-(4-methylpyrimidin-2-yl)-1,4,5,6-tetrahydropyrrolo[3,4-c]pyrazol-3-amine, N-(2-ethoxy-5-fluoropyrimidin-4-yl)-6,6-dimethyl-5-{[(2S,5R)-2,4,5-trimethylpiperazin-1-yl]carbonyl})-1,4,5,6-tetrahydropyrrolo[3,4-c]pyrazol-3-amine, N-(2-ethoxy-5-fluoropyrimidin-4-yl)-6,6-dimethyl-5-{[4-ethyl(2S,5R)-2,5-dimethylpiperazin-1-yl]carbonyl})-1,4,5,6-tetrahydropyrrolo[3,4-c]pyrazol-3-amine, N-(2-ethoxy-5-fluoropyrimidin-4-yl)-6,6-dimethyl-5-{[(2S)-2,4,5,5-tetramethylpiperazin-1-yl]carbonyl})-1,4,5,6-tetrahydropyrrolo[3,4-c]pyrazol-3-amine, N-(2-ethoxy-5-fluoropyrimidin-4-yl)-5-{[(2S,5R)-4-(2-methoxyethyl)-2,5-dimethylpiperazin-1-yl]carbonyl}-6,6-dimethyl-1,4,5,6-tetrahydropyrrolo[3,4-c]pyrazol-3-amine, N-(2-ethoxy-5-fluoropyrimidin-4-yl)-5-{[(2S,5R)-4-(3-methoxypropyl)-2,5-dimethylpiperazin-1-yl]carbonyl}-6,6-dimethyl-1,4,5,6-tetrahydropyrrolo[3,4-c]pyrazol-3-amine, N-[5-fluoro-2-(2,2,2-trifluoroethoxy)pyrimidin-4-yl]-5-{[(2S,5R)-4-(3-methoxypropyl)-2,5-dimethylpiperazin-1-yl]carbonyl}-6,6-dimethyl-1,4,5,6-tetrahydropyrrolo[3,4-c]pyrazol-3-amine, N-[5-fluoro-2-(2,2,2-trifluoroethoxy)pyrimidin-4-yl]-6,6-dimethyl-5-{[(2S,5R)-2,4,5-trimethylpiperazin-1-yl]carbonyl}-1,4,5,6-tetrahydropyrrolo[3,4-c]pyrazol-3-amine, N-[5-fluoro-2-(2,2,2-trifluoroethoxy)pyrimidin-4-yl]-6,6-dimethyl-5-{[(2S)-2,4,5,5-tetramethylpiperazin-1-yl]carbonyl})-1,4,5,6-tetrahydropyrrolo[3,4-c]pyrazol-3-amine, 5-{[(2S,5R)-2,5-dimethyl-4-(tetrahydro-2H-pyran-4-ylmethyl)piperazin-1-yl]carbonyl}-N-(2-ethoxy-5-fluoropyrimidin-4-yl)-6,6-dimethyl-1,4,5,6-tetrahydropyrrolo[3,4-c]pyrazol-3-amine, 5-{[(2S,5R)-2,5-dimethyl-4-(tetrahydro-2H-pyran-4-yl)piperazin-1-yl]carbonyl}-N-(2-ethoxy-5-fluoropyrimidin-4-yl)-6,6-dimethyl-1,4,5,6-tetrahydropyrrolo[3,4-c]pyrazol-3-amine, 2-((5S)-4-{[3-[(2-ethoxy-5-fluoropyrimidin-4-yl)amino]-6,6-dimethyl-4,6-dihydropyrrolo[3,4-c]pyrazol-5(1H)-yl]carbonyl}-1,5-dimethylpiperazin-2-yl)ethanol, 2-((5S)-4-{[3-[(2-ethoxy-5-fluoropyrimidin-4-yl)amino]-6,6-dimethyl-4,6-dihydropyrrolo[3,4-c]pyrazol-5(1H)-yl]carbonyl}-1,5-dimethylpiperazin-2-yl)ethanol, 5-[(4-fluoro-1-methylpiperidin-4-yl)carbonyl]-N-[5-fluoro-2-(2,2,2-trifluoroethoxy)pyrimidin-4-yl]-6,6-dimethyl-1,4,5,6-tetrahydropyrrolo[3,4-c]pyrazol-3-amine, 5-{[(2S,5R)-2,5-dimethyl-4-(tetrahydro-2H-pyran-4-ylmethyl)piperazin-1-yl]carbonyl}-N-[5-fluoro-2-(methoxymethyl)pyrimidin-4-yl]-6,6-dimethyl-1,4,5,6-tetrahydropyrrolo[3,4-c]pyrazol-3-amine, and 2-((5S)-4-{[3-{[5-fluoro-2-(methoxymethyl)pyrimidin-4-yl]amino}-6,6-dimethyl-4,6-dihydropyrrolo[3,4-c]pyrazol-5(1H)-yl]carbonyl}-1,5-dimethylpiperazin-2-yl)ethanol.

Another embodiment provides the method of treating uveitis, wherein the compound is N$^4$-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-N$^2$-ethyl-5-fluoropyrimidine-2,4-diamine, or a pharmaceutically acceptable salt thereof. Another embodiment provides the method of treating uveitis, wherein the compound is N⁴-(5-{[(2S,5R)-2,5-dimethyl-4-(tetrahydro-2H-pyran-4-yl)piperazin-1-yl]carbonyl)}-6,6-dimethyl-1,4,5,6-tetrahydropyrrolo[3,4-c]pyrazol-3-yl)-N²-ethyl-5-fluoropyrimidine-2,4-diamine, or a pharmaceutically acceptable salt thereof. Another embodiment provides the method of treating uveitis, wherein the compound is 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof. Another embodiment provides the method of treating uveitis, wherein the compound is 5-{[(2S,5R)-2,5-dimethyl-4-(tetrahydro-2H-pyran-4-ylmethyl)piperazin-1-yl]carbonyl}-N-(2-ethyl-5-fluoropyrimidin-4-yl)-6,6-dimethyl-1,4,5,6-tetrahydropyrrolo[3,4-c]pyrazol-3-amine, or a pharmaceutically acceptable salt thereof. Another embodiment provides the method of treating uveitis, wherein the compound is 5-{[(2S,5R)-2,5-dimethyl-4-(tetrahydro-2H-pyran-4-yl)piperazin-1-yl]carbonyl}-N-(4-methoxypyrimidin-2-yl)-6,6-dimethyl-1,4,5,6-tetrahydropyrrolo[3,4-c]pyrazol-3-amine, or a pharmaceutically acceptable salt thereof. Another embodiment provides the method of treating uveitis, wherein the compound is 5-{[(2S,5R)-2,5-dimethyl-4-(tetrahydro-2H-pyran-4-yl)piperazin-1-yl]carbonyl}-6,6-dimethyl-N-[4-(trifluoromethyl)pyrimidin-2-yl]-1,4,5,6-tetrahydropyrrolo[3,4-c]pyrazol-3-amine, or a pharmaceutically acceptable salt thereof. Another embodiment provides the method of treating uveitis, wherein the compound is 5-{[(2S,5R)-2,5-dimethyl-4-(tetrahydro-2H-pyran-4-yl)piperazin-1-yl]carbonyl}-N-(2-ethoxy-5-fluoropyrimidin-4-yl)-6,6-dimethyl-1,4,5,6-tetrahydropyrrolo[3,4-c]pyrazol-3-amine, or a pharmaceutically acceptable salt thereof. Another embodiment provides the method of treating uveitis, wherein the compound is N⁴-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-N2-ethyl-5-fluoropyrimidine-2,4-diamine, or a pharmaceutically acceptable salt thereof. Another embodiment provides the method of treating uveitis, wherein the compound is N⁴-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-N²-ethylpyrimidine-2,4-diamine, or a pharmaceutically acceptable salt thereof. Another embodiment provides the method of treating uveitis, wherein the uveitis is anterior uveitis, intermediate uveitis, posterior uveitis, or panuveitis uveitis.

One embodiment provides a method of treating uveitis in a subject in need thereof comprising administering to the subject a composition comprising a compound having the formula 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof, and a pharmaceutically acceptable excipient.

One embodiment provides a method of treating uveitis in a subject in need thereof comprising administering to the subject a composition comprising a compound, or a pharmaceutically acceptable salt thereof, selected from the group consisting of:

N²-(cyclopropylmethyl)-N⁴-(6,6-dimethyl-5-{[(2 S)-2,4,5,5-tetramethylpiperazin-1-yl]carbonyl})-1,4,5,6-tetrahydropyrrolo[3,4-c]pyrazol-3-yl)-5-fluoropyrimidine-2,4-diamine;

N⁴-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-5-fluoro-N²-isobutylpyrimidine-2,4-diamine;

5-{[(2S,5R)-4-ethyl-2,5-dimethylpiperazin-1-yl]carbonyl)}-N-(5-fluoro-2-methoxypyrimidin-4-yl)-6,6-dimethyl-1,4,5,6-tetrahydropyrrolo[3,4-c]pyrazol-3-amine;

5-{[(2S,5R)-4-ethyl-2,5-dimethylpiperazin-1-yl]carbonyl)}-N-(5-fluoro-2-methylpyrimidin-4-yl)-6,6-dimethyl-1,4,5,6-tetrahydropyrrolo[3,4-c]pyrazol-3-amine;

5-{[(2S,5R)-4-ethyl-2,5-dimethylpiperazin-1-yl]carbonyl)}-N-(5-fluoro-2,6-dimethylpyrimidin-4-yl)-6,6-dimethyl-1,4,5,6-tetrahydropyrrolo[3,4-c]pyrazol-3-amine;

2(S),5(S)-{[dimethyl-4-methylpiperazin-1-yl]carbonyl}-N-(5-fluoro-2-methylpyrimidin-4-yl)-6,6-dimethyl-1,4,5,6-tetrahydropyrrolo[3,4-c]pyrazol-3-amine;

[3-(5-fluoro-2-methyl-pyrimidin-4-ylamino)-6,6-dimethyl-4,6-dihydro-1H-pyrrolo[3,4-c]pyrazol-5-yl]-[4-(3-hydroxy-propyl)-2,5-dimethyl-piperazin-1-yl]-methanone;

N⁴-(6,6-dimethyl-5-{[(3S,8aS)-3-methylhexahydropyrrolo[1,2-a]pyrazin-2(1H)-yl]carbonyl})-1,4,5,6-tetrahydropyrrolo[3,4-c]pyrazol-3-yl)-N²-ethyl-5-fluoropyrimidine-2,4-diamine;

N²-ethyl-5-fluoro-N⁴-(5-{[(2S,5R)-4-(2-methoxyethyl)-2,5-dimethylpiperazin-1-yl]carbonyl}-6,6-dimethyl-1,4,5,6-tetrahydropyrrolo[3,4-c]pyrazol-3-yl)pyrimidine-2,4-diamine;

N4-(5-{[(2S,5R)-2,5-dimethyl-4-(3,3,3-trifluoropropyl)piperazin-1-yl]carbonyl}-6,6-dimethyl-1,4,5,6-tetrahydropyrro[3,4-c]pyrazol-3-yl)-N2-ethyl-5-fluoropyrimidine-2,4-diamine;

N-(5-fluoro-2-morpholin-4-ylpyrimidin-4-yl)-6,6-dimethyl-5-{[(2S,5R)-2,4,5-trimethylpiperazin-1-yl]carbonyl}-1,4,5,6-tetrahydropyrrolo[3,4-c]pyrazol-3-amine;

N²-ethyl-5-fluoro-N⁴-{5-[(4-fluoro-1-methylpiperidin-4-yl)carbonyl]-6,6-dimethyl-1,4,5,6-tetrahydropyrrolo[3,4-c]pyrazol-3-yl}pyrimidine-2,4-diamine;

N-(2-ethyl-5-fluoropyrimidin-4-yl)-6,6-dimethyl-5-{[(2S,5R)-2,4,5-trimethylpiperazin-1-yl]carbonyl}-1,4,5,6-tetrahydropyrrolo[3,4-c]pyrazol-3-amine;

N-(2-ethoxypyrimidin-4-yl)-6,6-dimethyl-5-{[(2S,5R)-2,4,5-trimethylpiperazin-1-yl]carbonyl})-1,4,5,6-tetrahydropyrrolo[3,4-c]pyrazol-3-amine;

5-{[(2S,5R)-2,5-dimethyl-4-(3,3,3-trifluoropropyl)piperazin-1-yl]carbonyl)}-N-(2-ethyl-5-fluoropyrimidin-4-yl)-6,6-dimethyl-1,4,5,6-tetrahydropyrrolo[3,4-c]pyrazol-3-amine;

5-[(4-fluoro-1-methylpiperidin-4-yl)carbonyl]-N-(5-fluoro-2-methylpyrimidin-4-yl)-6,6-dimethyl-1,4,5,6-tetrahydropyrrolo[3,4-c]pyrazol-3-amine;

N-(2-ethyl-5-fluoropyrimidin-4-yl)-5-[(4-fluoro-1-methylpiperidin-4-yl)carbonyl]-6,6-dimethyl-1,4,5,6-tetrahydropyrrolo[3,4-c]pyrazol-3-amine;

N-(5-fluoro-2-methylpyrimidin-4-yl)-6,6-dimethyl-5-{[(3S,8aS)-3-methylhexahydropyrrolo[1,2-a]pyrazin-2(1H)-yl]carbonyl}-1,4,5,6-tetrahydropyrrolo[3,4-c]pyrazol-3-amine;

N-(5-fluoro-2-methylpyrimidin-4-yl)-6,6-dimethyl-5-{[(2S,5R)-2,4,5-trimethylpiperazin-1-yl]carbonyl}-1,4,5,6-tetrahydropyrrolo[3,4-c]pyrazol-3-amine;

5-{[(3S)-3-ethyl-4-methylpiperazin-1-yl]carbonyl}-N-(5-fluoro-2-methylpyrimidin-4-yl)-6,6-dimethyl-1,4,5,6-tetrahydropyrrolo[3,4-c]pyrazol-3-amine;

5-{[(3R)-3-ethyl-4-methylpiperazin-1-yl]carbonyl}-N-(5-fluoro-2-methylpyrimidin-4-yl)-6,6-dimethyl-1,4,5,6-tetrahydropyrrolo[3,4-c]pyrazol-3-amine;

5-{[(2S,5R)-2,5-dimethyl-4-(tetrahydro-2H-pyran-4-yl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine;

4-[((2R,5S)-4-{[3-[(5-fluoro-2-methylpyrimidin-4-yl) amino]-6,6-dimethyl-4,6-dihydropyrrolo[3,4-c]pyrazol-5 (1H)-yl]carbonyl}-2,5-dimethylpiperazin-1-yl)methyl] tetrahydro-2H-pyran-4-ol;

2-((5S)-4-{[3-[(5-fluoro-2-methylpyrimidin-4-yl)amino]-6, 6-dimethyl-4,6-dihydropyrrolo[3,4-c]pyrazol-5(1H)-yl] carbonyl}-1,5-dimethylpiperazin-2-yl)ethanol;

2-((5S)-4-{[3-[(5-fluoro-2-methylpyrimidin-4-yl)amino]-6, 6-dimethyl-4,6-dihydropyrrolo[3,4-c]pyrazol-5(1H)-yl] carbonyl}-1,5-dimethylpiperazin-2-yl)ethanol;

5-{[(2S,5R)-2,5-dimethyl-4-(tetrahydro-2H-pyran-4-ylmethyl)piperazin-1-yl]carbonyl}-N-(4-methoxypyrimidin-2-yl)-6,6-dimethyl-1,4,5,6-tetrahydropyrrolo[3,4-c]pyrazol-3-amine;

N-(4, 6-dimethylpyrimidin-2-yl)-5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c] pyrazol-3-amine;

N-[5-fluoro-2-(3-methoxypropoxy)pyrimidin-4-yl]-6,6-dimethyl-5-{[(2 S)-2,4,5,5-tetramethylpiperazin-1-yl]carbonyl}-1,4,5,6-tetrahydropyrrolo[3,4-c]pyrazol-3-amine;

N-[5-fluoro-2-(3-methoxypropoxy)pyrimidin-4-yl]-6,6-dimethyl-5-{[(2S,5R)-2,4,5-trimethylpiperazin-1-yl]carbonyl}-1,4,5,6-tetrahydropyrrolo[3,4-c]pyrazol-3-amine;

N-[5-fluoro-2-(2-methoxyethoxy)pyrimidin-4-yl]-6,6-dimethyl-5-{[(2S)-2,4,5,5-tetramethylpiperazin-1-yl]carbonyl}-1,4,5,6-tetrahydropyrrolo[3,4-c]pyrazol-3-amine;

N-[5-fluoro-2-(2-methoxyethoxy)pyrimidin-4-yl]-6,6-dimethyl-5-{[(2S,5R)-2,4,5-trimethylpiperazin-1-yl]carbonyl}-1,4,5,6-tetrahydropyrrolo[3,4-c]pyrazol-3-amine;

2(S), 5(S)-{[dimethyl-4-methylpiperazin-1-yl]carbonyl}-N-(5-fluoro-2-ethoxypyrimidin-4-yl)-6,6-dimethyl-1,4,5,6-tetrahydropyrrolo[3,4-c]pyrazol-3-amine;

[3-(2-Ethoxy-5-fluoro-pyrimidin-4yl-amino)-6,6-dimethyl-4,6-dihydro-1H-pyrrolo[3,4-c]pyrazol-5-yl]-(R)-hexahydro-pyrrolo[1,2-a]pyrazin-2-yl-methanone;

5-{[(3S,8aS)-3,8a-dimethylhexahydropyrrolo[1,2-a] pyrazin-2(1H)-yl]carbonyl)}-N-(2-ethoxy-5-fluoropyrimidin-4-yl)-6,6-dimethyl-1,4,5,6-tetrahydropyrrolo[3, 4-c]pyrazol-3-amine;

5-{[(3S)-3,4-dimethylpiperazin-1-yl]carbonyl}-N-(2-ethoxy-5-fluoropyrimidin-4-yl)-6,6-dimethyl-1,4,5,6-tetrahydropyrrolo[3,4-c]pyrazol-3-amine;

5-{[(3R)-3,4-dimethylpiperazin-1-yl]carbonyl}-N-(2-ethoxy-5-fluoropyrimidin-4-yl)-6,6-dimethyl-1,4,5,6-tetrahydropyrrolo[3,4-c]pyrazol-3-amine;

5-{[(2S,5R)-2,5-dimethyl-4-(3,3,3-trifluoropropyl)piperazin-1-yl]carbonyl)}-N-(2-ethoxy-5-fluoropyrimidin-4-yl)-6,6-dimethyl-1,4,5,6-tetrahydropyrrolo[3,4-c]pyrazol-3-amine;

N-(2-ethoxy-5-fluoropyrimidin-4-yl)-5-{[(3S,8aS)-3-isopropylhexahydropyrrolo[1,2-a]pyrazin-2(1H)-yl]carbonyl}-6,6-dimethyl-1,4,5,6-tetrahydropyrrolo[3,4-c]pyrazol-3-amine;

4-[((2R,5S)-4-{[3-[(2-ethoxy-5-fluoropyrimidin-4-yl) amino]-6,6-dimethyl-4,6-dihydropyrrolo[3,4-c]pyrazol-5 (1H)-yl]carbonyl}-2,5-dimethylpiperazin-1-yl)methyl] tetrahydro-2H-pyran-4-ol;

2-((5S)-4-{[3-[(5-fluoro-2-methoxypyrimidin-4-yl)amino]-6,6-dimethyl-4,6-dihydropyrrolo[3,4-c]pyrazol-5(1H)-yl] carbonyl}-1,5-dimethylpiperazin-2-yl)ethanol;

2-((5S)-4-{[3-[(5-fluoro-2-methoxypyrimidin-4-yl)amino]-6,6-dimethyl-4,6-dihydropyrrolo[3,4-c]pyrazol-5(1H)-yl] carbonyl}-1,5-dimethylpiperazin-2-yl)ethanol;

N-(2-ethoxy-5-fluoropyrimidin-4-yl)-5-[(4-fluoro-1-methylpiperidin-4-yl)carbonyl]-6,6-dimethyl-1,4,5,6-tetrahydropyrrolo[3,4-c]pyrazol-3-amine;

N-[5-fluoro-2-(2-methoxyethoxy)pyrimidin-4-yl]-5-[(4-fluoro-1-methylpiperidin-4-yl)carbonyl]-6,6-dimethyl-1, 4,5,6-tetrahydropyrrolo[3,4-c]pyrazol-3-amine;

N-[5-fluoro-2-(3-methoxypropoxy)pyrimidin-4-yl]-5-[(4-fluoro-1-methylpiperidin-4-yl)carbonyl]-6,6-dimethyl-1, 4,5,6-tetrahydropyrrolo[3,4-c]pyrazol-3-amine;

N-(2-ethoxy-5-fluoropyrimidin-4-yl)-6,6-dimethyl-5-{[1-(3,3,3-trifluoropropyl)piperidin-4-yl]carbonyl}-1,4,5,6-tetrahydropyrrolo[3,4-c]pyrazol-3-amine;

N-(2-ethoxy-5-fluoropyrimidin-4-yl)-6,6-dimethyl-5-{[1-(tetrahydro-2H-pyran-4-yl)piperidin-4-yl]carbonyl}-1,4, 5,6-tetrahydropyrrolo[3,4-c]pyrazol-3-amine;

N-(4-ethoxypyrimidin-2-yl)-6,6-dimethyl-5-{[(2S,5R)-2,4, 5-trimethylpiperazin-1-yl]carbonyl})-1,4,5,6-tetrahydropyrrolo[3,4-c]pyrazol-3-amine;

N-(4-ethoxypyrimidin-2-yl)-5-{[(2S,5R)-4-(3-methoxypropyl)-2,5-dimethylpiperazin-1-yl]carbonyl}-6,6-dimethyl-1,4,5,6-tetrahydropyrrolo[3,4-c]pyrazol-3-amine; or 2-((5S)-4-{[3-{[5-fluoro-2-(methoxymethyl)pyrimidin-4-yl]amino}-6,6-dimethyl-4,6-dihydropyrrolo[3,4-c]pyrazol-5(1H)-yl]carbonyl}-1,5-dimethylpiperazin-2-yl)ethanol.

Another embodiment provides the method of treating uveitis, wherein the compound is N-(4-ethoxypyrimidin-2-yl)-6,6-dimethyl-5-{[(2S,5R)-2,4,5-trimethylpiperazin-1-yl]carbonyl)}-1,4,5,6-tetrahydropyrrolo[3,4-c]pyrazol-3-amine, or a pharmaceutically acceptable salt thereof. Another embodiment provides the method of treating uveitis, wherein the compound is 5-{[(3S,8aS)-3,8a-dimethylhexahydropyrrolo[1,2-a]pyrazin-2(1H)-yl]carbonyl}-N-(2-ethoxy-5-fluoropyrimidin-4-yl)-6,6-dimethyl-1,4,5,6-tetrahydropyrrolo[3,4-c]pyrazol-3-amine, or a pharmaceutically acceptable salt thereof. Another embodiment provides the method of treating uveitis, wherein the compound is N-(4,6-dimethylpyrimidin-2-yl)-5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-amine, or a pharmaceutically acceptable salt thereof. Another embodiment provides the method of treating uveitis, wherein the compound is N-[5-fluoro-2-(3-methoxypropoxy)pyrimidin-4-yl]-6,6-dimethyl-5-{[(2 S)-2,4,5,5-tetramethylpiperazin-1-yl]carbonyl}-1,4,5,6-tetrahydropyrrolo[3,4-c]pyrazol-3-amine, or a pharmaceutically acceptable salt thereof. Another embodiment provides the method of treating uveitis, wherein the compound is N-(2-ethoxypyrimidin-4-yl)-6,6-dimethyl-5-{[(2S,5R)-2,4,5-trimethylpiperazin-1-yl]carbonyl)}-1,4,5,6-tetrahydropyrrolo[3,4-c]pyrazol-3-amine, or a pharmaceutically acceptable salt thereof. Another embodiment provides the method of treating uveitis, wherein the compound is N-(2-ethyl-5-fluoropyrimidin-4-yl)-6,6-dimethyl-5-{[(2S,5R)-2, 4,5-trimethylpiperazin-1-yl]carbonyl}-1,4,5,6-tetrahydropyrrolo[3,4-c]pyrazol-3-amine, or a pharmaceutically acceptable salt thereof. Another embodiment provides the method of treating uveitis, wherein the compound is $N^2$-ethyl-5-fluoro-$N^4$-(5-{[(2S,5R)-4-(2-methoxyethyl)-2,5-dimethylpiperazin-1-yl]carbonyl}-6,6-dimethyl-1,4,5,6-tetrahydropyrrolo[3,4-c]pyrazol-3-yl)pyrimidine-2,4-diamine, or a pharmaceutically acceptable salt thereof. Another embodiment provides the method of treating uveitis, wherein the compound is 5-{[(2S,5R)-2,5-dimethyl-4-(tetrahydro-2H-pyran-4-yl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof. Another embodiment provides the method of treating uveitis, wherein the compound is 5-{[(2S,5R)-4-ethyl-2,5-dimethylpiperazin-1- yl]carbonyl}-N-(5-fluoro-2,6-dimethylpyrimidin-4-yl)-6,6-dimethyl-1,4,5,6-tetrahydropyrrolo[3,4-c]pyrazol-3-amine, or a pharmaceutically acceptable salt thereof. Another embodiment provides the method of treating uveitis, wherein the compound is N-(2-ethoxy-5-fluoropyrimidin-4-yl)-5-[(4-fluoro-1-methylpiperidin-4-yl)carbonyl]-6,6-dimethyl-1,4,5,6-tetrahydropyrrolo[3,4-c]pyrazol-3-amine, or a pharmaceutically acceptable salt thereof. Another embodiment provides the method of treating uveitis, wherein the compound is 4-[((2R,5S)-4-{[3-[(2-ethoxy-5-fluoropyrimidin-4-yl)amino]-6,6-dimethyl-4,6-dihydropyrrolo[3,4-c]pyrazol-5(1H)-yl]carbonyl}-2,5-dimethylpiperazin-1-yl)methyl]tetrahydro-2H-pyran-4-ol, or a pharmaceutically acceptable salt thereof. Another embodiment provides the method of treating uveitis, wherein the compound is N-[5-fluoro-2-(2-methoxyethoxy)pyrimidin-4-yl]-6,6-dimethyl-5-{[(2S,5R)-2,4,5-trimethylpiperazin-1-yl]carbonyl}-1,4,5,6-tetrahydropyrrolo[3,4-c]pyrazol-3-amine, or a pharmaceutically acceptable salt thereof. Another embodiment provides the method of treating uveitis, wherein the compound is 5-{[(2S,5R)-2,5-dimethyl-4-(tetrahydro-2H-pyran-4-ylmethyl)piperazin-1-yl]carbonyl}-N-(4-methoxypyrimidin-2-yl)-6,6-dimethyl-1,4,5,6-tetrahydropyrrolo[3,4-c]pyrazol-3-amine, or a pharmaceutically acceptable salt thereof. Another embodiment provides the method of treating uveitis, wherein the compound is N-(5-fluoro-2-methylpyrimidin-4-yl)-6,6-dimethyl-5-{[(2S,5R)-2,4,5-trimethylpiperazin-1-yl]carbonyl}-1,4,5,6-tetrahydropyrrolo[3,4-c]pyrazol-3-amine, or a pharmaceutically acceptable salt thereof. Another embodiment provides the method of treating uveitis, wherein the compound is $N^2$-(cyclopropylmethyl)-$N^4$-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-5-fluoropyrimidine-2,4-diamine, or a pharmaceutically acceptable salt thereof.

One embodiment provides a method of treating uveitis in a subject in need thereof comprising administering to the subject a composition comprising a compound, or a pharmaceutically acceptable salt thereof, selected from the group consisting of:

N-(5-{[(8 S)-6, 8-dimethyl-6,9-diazaspiro[4.5]dec-9-yl]carbonyl}-6,6-dimethyl-1,4,5,6-tetrahydropyrrolo[3,4-c]pyrazol-3-yl)pyridine-2-carboxamide;

N-(5-((3S,8aS)-3-benzyl-octahydropyrrolo[1,2-a]pyrazine-2-carbonyl)-6,6-dimethyl-1,4,5,6-tetrahydropyrrolo[3,4-c]pyrazol-3-yl)benzamide;

N-(5-((3S,8aS)-3-benzyl-octahydropyrrolo[1,2-a]pyrazine-2-carbonyl)-6,6-dimethyl-1,4,5,6-tetrahydropyrrolo[3,4-c]pyrazol-3-yl)-3-methoxybenzamide;

3,4-dichloro-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)benzamide;

N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-4,6-dimethylpicolinamide;

N-(5-((3S,8aS)-3-(cyclohexylmethyl)-octahydropyrrolo[1,2-a]pyrazine-2-carbonyl)-6,6-dimethyl-1,4,5,6-tetrahydropyrrolo[3,4-c]pyrazol-3-yl)picolinamide;

3-cyano-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)benzamide;

N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-2,3-dihydrobenzofuran-5-carboxamide;

4,5-dichloro-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)thiazole-2-carboxamide;

N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)H-pyrrolo[1,2-f]pyrimidine-3-carboxamide;

N-(5-((2R,5S)-2-(2-hydroxyethyl)-5-methyl-1-propylpiperazine-4-carbonyl)-6,6-dimethyl-1,4,5,6-tetrahydropyrrolo[3,4-c]pyrazol-3-yl)picolinamide;

N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-5-nitropicolinamide;

N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)quinoline-2-carboxamide;

N-(5-((+/-)-trans-1-allyl-2,5-dimethylpiperazine-4-carbonyl)-6,6-dimethyl-1,4,5,6-tetrahydropyrrolo[3,4-c]pyrazol-3-yl)picolinamide;

5-bromo-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)picolinamide;

N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-5-fluoropicolinamide;

N-(5-((+/-)-trans-1-ethyl-2,5-dimethylpiperazine-4-carbonyl)-6,6-dimethyl-1,4,5,6-tetrahydropyrrolo[3,4-c]pyrazol-3-yl)picolinamide;

N-(5-((+/-)-trans-1-(cyclopropylmethyl)-2,5-dimethylpiperazine-4-carbonyl)-6,6-dimethyl-1,4,5,6-tetrahydropyrrolo[3,4-c]pyrazol-3-yl)picolinamide;

N-(5-(1-(3-hydroxypropyl)-2,5-dimethylpiperazine-4-carbonyl)-6,6-dimethyl-1,4,5,6-tetrahydropyrrolo[3,4-c]pyrazol-3-yl)picolinamide;

N-(5-((3S,8aS)-3-isopropyl-octahydropyrrolo[1,2-a]pyrazine-2-carbonyl)-6,6-dimethyl-1,4,5,6-tetrahydropyrrolo[3,4-c]pyrazol-3-yl)picolinamide;

2-bromo-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)thiazole-4-carboxamide;

N-(6,6-dimethyl-5-((2R,5S)-1,2,5-trimethylpiperazine-4-carbonyl)-1,4,5,6-tetrahydropyrrolo[3,4-c]pyrazol-3-yl)picolinamide;

N-(5-((2R,5S)-1-ethyl-2,5-dimethylpiperazine-4-carbonyl)-6,6-dimethyl-1,4,5,6-tetrahydropyrrolo[3,4-c]pyrazol-3-yl)picolinamide;

N-(5-((2R,5S)-2,5-dimethyl-1-propylpiperazine-4-carbonyl)-6,6-dimethyl-1,4,5,6-tetrahydropyrrolo[3,4-c]pyrazol-3-yl)picolinamide;

N-(5-((2R,5S)-1-(cyclopropylmethyl)-2,5-dimethylpiperazine-4-carbonyl)-6,6-dimethyl-1,4,5,6-tetrahydropyrrolo[3,4-c]pyrazol-3-yl)picolinamide;

N-(5-((2R,5S)-1-butyl-2,5-dimethylpiperazine-4-carbonyl)-6,6-dimethyl-1,4,5,6-tetrahydropyrrolo[3,4-c]pyrazol-3-yl)picolinamide;

N-(6,6-dimethyl-5-{[(2S)-2,4,5,5-tetramethylpiperazin-1-yl]carbonyl}-1,4,5,6-tetrahydropyrrolo[3,4-c]pyrazol-3-yl)pyridine-2-carboxamide;

N-(5-{[(7S)-5,7-dimethyl-5,8-diazaspiro[3.5]non-8-yl]carbonyl}-6,6-dimethyl-1,4,5,6-tetrahydropyrrolo[3,4-c]pyrazol-3-yl)pyridine-2-carboxamide;

N-(5-{[(2S,5R)-4-(3-methoxypropyl)-2,5-dimethylpiperazin-1-yl]carbonyl}-6,6-dimethyl-1,4,5,6-tetrahydropyrrolo[3,4-c]pyrazol-3-yl)pyridine-2-carboxamide;

N-(5-((2R,5S)-2,5-dimethyl-1-(2(tetrahydro-2H-pyran-4-yl)ethyl)piperazine-4-carbonyl)-6,6-dimethyl-1,4,5,6-tetrahydropyrrolo[3,4-c]pyrazol-3-yl)picolinamide;

N-(5-((2R,5S)-2,5-dimethyl-1-(tetrahydro-2H-pyran-4-yl)piperazine-4-carbonyl)-6,6-dimethyl-1,4,5,6-tetrahydropyrrolo[3,4-c]pyrazol-3-yl)picolinamide;

N-(5-{[(2S,5R)-2,5-dimethyl-4-(tetrahydrofuran-3-ylmethyl)piperazin-1-yl]carbonyl})-6,6-dimethyl-1,4,5,6-tetrahydropyrrolo[3,4-c]pyrazol-3-yl)pyridine-2-carboxamide;

N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)isoquinoline-3-carboxamide;

N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-1,6-naphthyridine-2-carboxamide;

3-cyclopropyl-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-1H-pyrazole-5-carboxamide;

N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)quinoxaline-2-carboxamide;

3-tert-butyl-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-1-methyl-1H-pyrazole-5-carboxamide;

3-cyclopropyl-N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-1H-pyrazole-5-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-5-fluoropyridine-2-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-5-methoxypyridine-2-carboxamide;

5-chloro-N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)pyridine-2-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-6-methylpyridine-2-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-3-ethyl-1-methyl-1H-pyrazole-5-carboxamide;

2-cyclopropyl-N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-1,3-oxazole-4-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-3-methylbenzamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-4-fluorobenzamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-3-fluorobenzamide;

N-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)-5-ethylpyridine-2-carboxamide;

N-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)-5-methylpyridine-2-carboxamide;

N-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)-5-methoxypyridine-2-carboxamide;

5-chloro-N-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)pyridine-2-carboxamide;

2-(3,5-dimethylisoxazol-4-yl)-N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)acetamide;

5-cyano-N-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)pyridine-2-carboxamide;

and 5-cyano-N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)pyridine-2-carboxamide.

One embodiment provides a method of treating uveitis in a subject in need thereof comprising administering to the subject a composition comprising a compound, or a pharmaceutically acceptable salt thereof, having the formula (I):

wherein:
X is C or N;
$R^1$ is selected from an aryl or wherein ring A is a 5 to 6 membered heterocyclyl containing Z, wherein Z is an O, S or N heteroatom which is adjacent to the point of attachment, and wherein $R^1$ is optionally further substituted with 0 to 3 $R^9$ groups and wherein two of the $R^9$ groups may optionally cyclize to form an aryl or a 5-6 membered heterocyclyl ring containing N or S fused to the aryl or heterocyclyl to which it is attached;

$R^2$ is H or $C_1$-$C_6$ alkyl optionally further substituted with 0 to 3 $R^9$ groups;

when X is N, $R^3$ may be attached to any carbon on the ring and is selected from H, $C_1$-$C_6$ alkyl, halide, or perfluoroalkyl;

when X is C, $R^3$ is a fluoro and is attached to X;

$R^4$ and $R^5$ are each independently selected from H, $R^a$—O—$R^b$, $C_1$-$C_8$ alkyl, $C_2$-$C_8$ alkenyl, $C_2$-$C_8$ alkynyl, —$(R^d)_m$—$(C_3$-$C_{12}$ cycloalkyl), —$(R^d)_m$-aryl, —$(R^d)_m$-(3-15 membered heterocyclyl), —$(R^d)_m$—$(C_1$-$C_6$ perfluoroalkyl), —$(R^d)_m$-halide, —$(R^d)_m$—CN, —$(R^d)_m$—C(O)$R^a$, —$(R^d)_m$—C(O)O$R^a$, —$(R^d)_m$—C(O)NR$^a$R$^b$, —$(R^d)_m$—OR$^a$, —$(R^d)_m$—OC(O)R$^a$, —$(R^d)_m$—OC(O)NR$^a$R$^b$, —$(R^d)_m$—O—S(O)R$^a$, —$(R^d)_m$—OS(O)$_2$R$^a$, —$(R^d)_m$—OS(O)$_2$NR$^a$R$^b$, —$(R^d)_m$—OS(O)NR$^a$R$^b$, —$(R^d)_m$—NO$_2$, —$(R^d)_m$—NR$^a$R$^b$, —$(R^d)_m$—N(R$^a$)C(O)R$^b$, —$(R^d)_m$—N(R$^a$)C(O)OR$^b$, —$(R^d)_m$—N(R$^c$)C(O)NR$^a$R$^b$, —$(R^d)_m$—N(R$^a$)S(O)$_2$R$^b$, —$(R^d)_m$—N(R$^a$)S(O)R$^b$, —$(R^d)_m$—SR$^a$, —$(R^d)_m$—S(O)R$^a$, —$(R^d)_m$—S(O)$_2$R$^a$, —$(R^d)_m$—S(O)NR$^a$R$^b$, —$(R^d)_m$—S(O)$_2$NR$^a$R$^b$, —$(R^d)_m$—O—(R$^e$)$_m$—NR$^a$R$^b$ or —$(R^d)_m$—NR$^a$—(R$^e$)—OR$^b$, or $R^4$ and $R^5$ may together cyclize to form a 3- to 5-membered spirocycloalkyl; wherein any of the said $C_3$-$C_{12}$ cycloalkyl, aryl, heterocyclyl, or heteroaryl are independently optionally further substituted by 0 to 3 R$_9$ groups;

$R^6$ is selected from $R^a$—O—$R^b$, $C_1$-$C_8$ alkyl, $C_2$-$C_8$ alkenyl, $C_2$-$C_8$ alkynyl, —$(R^d)_m$—$(C_3$-$C_{12}$ cycloalkyl), —$(R^d)_m$-aryl, —$(R^d)_m$-(3-15 membered heterocyclyl), —$(R^d)_m$—$(C_1$-$C_6$ perfluoroalkyl), —$(R^d)_m$-halide, —$(R^d)_m$—CN, —$(R^d)_m$—C(O)R$^a$, —$(R^d)_m$—C(O)OR, —(R)$_m$—C(O)NR$^a$R$^b$, —$(R^d)_m$—OR$^a$, —$(R^d)_m$—OC(O)R$^a$, —$(R^d)_m$—OC(O)NR$^a$R$^b$, —$(R^d)_m$—O—S(O)R$^a$, —$(R^d)_m$—OS(O)$_2$R$^a$, —$(R^d)_m$—OS(O)$_2$NR$^a$R$^b$, —$(R^d)_m$—OS(O)NR$^a$R$^b$, —(R$_d$)$_m$—NO$_2$, —$(R^d)_m$—NR$^a$R$^b$, (R$^d$)$_m$—N(R$^a$)C(O)R$^b$, —$(R^d)_m$—N(R$^a$)C(O)OR$^b$, —$(R^d)_m$—N(R$^c$)C(O)NR$^a$R$^b$, —$(R^d)_m$—N(R$^a$)S(O)$_2$R$^b$, —$(R^d)_m$—N(R$^a$)S(O)R$^b$, —$(R^d)_m$—SR$^a$, —$(R^d)_m$—S(O)R$^a$, —$(R^d)_m$—S(O)$_2$R$^a$, —$(R^d)_m$—S(O)NR$^a$R$^b$, —$(R^d)_m$—S(O)$_2$NR$^a$R$^b$, —$(R^d)_m$—O—(R$^e$)$_m$—NR$^a$R$^b$ or —$(R^d)_m$—NR$^a$—(R$^e$)—OR$^b$; or $R^6$ may together with $R^4$ cyclize to form a 4- to 7-membered heterocyclyl ring fused to the piperazine or piperadine to which they are attached; and wherein any of the said alkyl, alkenyl, alkynyl, cycloalkyl, aryl, heterocyclyl, and heteroaryl may independently be further substituted with 0 to 3 R$^9$ groups;

each $R^7$ and $R^8$ is independently $C_1$-$C_2$ alkyl, or $R^7$ and $R^8$ together cyclize to form a cyclopropyl or cyclobutyl;

each $R^9$ is independently selected from H, $R^a$—O—$R^b$, $C_1$-$C_8$ alkyl, $C_2$-$C_8$ alkenyl, $C_2$-$C_8$ alkynyl, —$(R^d)_m$—$(C_3$-$C_{12}$ cycloalkyl), —$(R^d)_m$-aryl, —$(R^d)_m$-(3-15 membered heterocyclyl), —$(R^d)_m$—$(C_1$-$C_6$ perfluoroalkyl), —$(R^d)_m$-halide, —$(R^d)_m$—CN, —$(R^d)_m$—C(O)R$^a$, —$(R^d)_m$—C(O)OR$^a$, —$(R^d)_m$—C(O)NR$^a$R$^b$, —$(R^d)_m$—OR$^a$, —$(R^d)_m$—OC(O)R$^a$, —$(R^d)_m$—OC(O)NR$^a$R$^b$, —$(R^d)_m$—O—S(O)R$^a$, —$(R^d)_m$—OS(O)$_2$R$^a$, —$(R^d)_m$—OS(O)$_2$NR$^a$R$^b$, —$(R^d)_m$—OS(O)NR$^a$R$^b$, —$(R^d)_m$—NO$_2$, —$(R^d)_m$—NR$^a$R$^b$, —$(R^d)_m$—N(R$^a$)C(O)R$^b$, —$(R^d)_m$—N(R$^a$)C(O)OR$^b$, —$(R^d)_m$—N(R$^c$)C(O)NR$^a$R$^b$, —$(R^d)_m$—N(R$^a$)S(O)$_2$R$^b$, —$(R^d)_m$—N(R$^a$)S(O)R$^b$, —$(R^d)_m$—SR$^a$, —$(R^d)_m$—S(O)R$^a$, —$(R^d)_m$—S(O)$_2$R$^a$, —$(R^d)_m$—S(O)NR$^a$R$^b$, —$(R^d)_m$—S(O)$_2$NR$^a$R$^b$, —$(R^d)_m$—O—(R$^e$)$_m$—NR$^a$R$^b$ or —$(R^d)_m$—NR$^a$—(R$^e$)—OR$^b$; and wherein any of the said alkyl, alkenyl, alkynyl, $R^d$, $R^e$, $C_3$-$C_{12}$ cycloalkyl, aryl or 3-15 membered heterocyclyl are independently optionally further substituted by 1-3 groups selected from -halide, $C_1$-$C_6$ alkyl, $C_1$-$C_6$ perfluoroalkyl, $C_1$-$C_6$alkoxyl, $C_1$-$C_6$alkylamino, CN or oxo;

each $R^a$, $R^b$ and $R^c$ is independently selected from H, $C_1$-$C_6$perfluoroalkyl, $C_1$-$C_8$ alkyl, $C_2$-$C_8$ alkenyl, —$(C_1$-$C_3$ alkylene)$_m$-$(C_3$-$C_8$ cycloalkyl), —$(C_1$-$C_3$ alkylene)$_m$-$(C_3$-$C_8$ cycloalkenyl), $C_2$-$C_8$ alkynyl, —$(C_1$-$C_3$ alkylene)$_m$-aryl, or —$(C_1$-$C_3$ alkylene)$_m$-(3-8 member heterocyclyl), and each $R^a$, $R^b$ and $R^c$ is independently optionally further substituted by 0 to 3 groups selected from halide, hydroxyl, —CN, $C_1$-$C_6$ alkyl, $C_1$-$C_6$ perfluoroalkyl, $C_1$-$C_6$ alkoxyl and $C_1$-$C_6$ alkylamino; or, when connected to the same nitrogen, $R^a$ and $R^b$ may optionally form a -(3-8 membered heterocyclyl), and said 3-8 membered heterocyclyl is optionally further substituted by 0 to 3 groups selected from halide, hydroxyl, —CN, $C_1$-$C_6$ alkyl, $C_1$-$C_6$ perfluoroalkyl, $C_1$-$C_6$ alkoxyl or $C_1$-$C_6$ alkylamino;

each $R^d$ and $R^e$ is independently —$(C_1$-$C_3$ alkylene)-, —$(C_2$-$C_5$ alkenylene)-, or —$(C_2$-$C_5$ alkynylene)-;

each m is independently 0 or 1; and with the proviso that if X=N, then $R^2$, $R^3$, $R^4$ and $R^5$ are not all H.

Another embodiment provides the method of treating uveitis, wherein $R^7$ and $R^8$ are both methyl. Another embodiment provides the method of treating uveitis, wherein X is N. Another embodiment provides the method of treating uveitis, wherein $R^1$ is a pyridine or a piperazine. Another embodiment provides the method of treating uveitis, wherein $R^1$ is a 5-membered heterocyclyl. Another embodiment provides the method of treating uveitis, wherein $R^1$ is selected from the group consisting of oxazole, isoxazole, thiazole or imidazole. Another embodiment provides the method of treating uveitis, wherein $R^2$ or $R^4$ is methyl. Another embodiment provides the method of treating uveitis, wherein $R^6$ is —$(R^d)_m$-(3-15 membered heterocyclyl). Another embodiment provides the method of treating uveitis, wherein $R^6$ is —$(R^d)_m$tetrahydropyran. Another embodiment provides the method of treating uveitis, wherein $R^6$ is tetrahydro-2H-pyran-4-ylmethyl. Another embodiment provides the method of treating uveitis, wherein $R^2$ is —CH$_3$ in (S) configuration. Another embodiment provides the method of treating uveitis, wherein $R^6$ is —$(R^d)_m$—OR$^a$.

One embodiment provides a method of treating uveitis in a subject in need thereof comprising administering to the subject a composition comprising a compound, or a pharmaceutically acceptable salt thereof, selected from the group consisting of:

N-(5-((2R,5S)-2,5-dimethyl-1-((tetrahydro-2H-pyran-4-yl)methyl)piperazine-4-carbonyl)-6,6-dimethyl-1,4,5,6-tetrahydropyrrolo[3,4-c]pyrazol-3-yl)picolinamide;

N-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)-5-fluoropyridine-2-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-5-ethylisoxazole-3-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-2,4-dimethyl-1,3-oxazole-5-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-2-methyl-1,3-thiazole-4-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-2-ethyl-4-methyl-1,3-oxazole-5-carboxamide;

1-cyclobutyl-N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-1H-imidazole-4-carboxamide N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-1-isopropyl-1H-imidazole-4-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-2-ethyl-1,3-oxazole-4-carboxamide;

N-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)-5-morpholin-4-ylpyridine-2-carboxamide; and N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-5-(trifluoromethyl)pyridine-2-carboxamide.

One embodiment provides a method of treating uveitis in a subject in need thereof comprising administering to the subject a composition comprising a compound, or a pharmaceutically acceptable salt thereof, having formula (A):

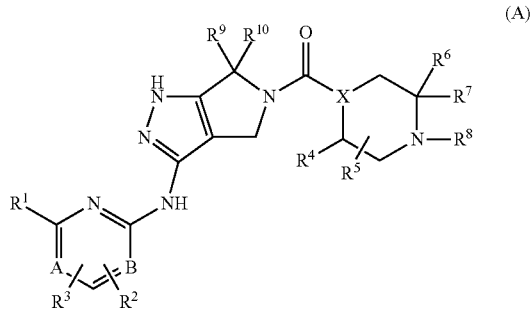

(A)

wherein

X is $C-R^{11}$ or N, wherein $R^{11}$ is H, halo, OH, $C_1$-$C_3$alkyl, $CF_3$, or CN;

A and B are independently C or N;

$R^1$, $R^2$ and $R^3$ are each independently selected from H, $R^a$—O—$R^b$, $C_1$-$C_8$ alkyl, $C_2$-$C_8$ alkenyl, $C_2$-$C_8$ alkynyl, —$(R^d)_m$—$(C_3$-$C_{12}$ cycloalkyl), —$(R^d)_m$-phenyl, —$(R^d)_m$-(3-15 membered heterocyclyl), —$(R^d)_m$—$(C_1$-$C_6$ perfluoroalkyl), —$(R^d)_m$-halide, —$(R^d)_m$—CN, —$(R^d)_m$—C(O)$R^a$, —$(R^d)_m$—C(O)O$R^a$, —$(R^d)_m$—C(O)N$R^aR^b$, —$(R^d)_m$—O$R^a$, —$(R^d)_m$—OC(O)$R^a$, —$(R^d)_m$—OC(O)N$R^aR^b$, —$(R^d)_m$—O—S(O)$R^a$, —$(R^d)_m$—OS(O)$_2R^a$, —$(R^d)_m$—OS(O)$_2$N$R^aR^b$, —$(R^d)_m$—OS(O)N$R^aR^b$, —$(R^d)_m$—NO$_2$, —$(R^d)_m$—N$R^aR^b$, —$(R^d)_m$—N($R^a$)C(O)$R^b$, —$(R^d)_m$—N($R^a$)C(O)O$R^b$, —$(R^d)_m$—N($R^c$)C(O)N$R^aR^b$, —$(R^d)_m$—N($R^a$)S(O)$_2R^b$, —$(R^d)_m$—N($R^a$)S(O)$R^b$, —$(R^d)_m$—S$R^a$, —$(R^d)_m$—S(O)$R^a$, —$(R^d)_m$—S(O)$_2R^a$, —$(R^d)_m$—S(O)N$R^aR^b$, —$(R^d)_m$—S(O)$_2$N$R^aR^b$, —$(R^d)_m$—O—$(R^e)_m$—N$R^aR^b$ or —$(R^d)_m$—N$R^a$—$(R^e)$—O$R^b$;

wherein $R^2$ and $R^3$ may together optionally cyclize to form a saturated or unsaturated 3-7 membered heterocyclyl fused to the 6-membered N-containing heteroaryl to which they are attached; and wherein any of the said alkyl, alkenyl, alkynyl, $R^a$, $R^b$, $R^c$, $R^d$, $R^e$, $C_3$-$C_{12}$ cycloalkyl, phenyl or 3-15 membered heterocyclyl, may independently be further optionally substituted by 0-3 $R^{12}$ groups;

$R^4$ and $R^5$ are each independently selected from H, $R^a$—O—$R^b$, $C_1$-$C_8$ alkyl, $C_2$-$C_8$ alkenyl, $C_2$-$C_8$ alkynyl, —$(R^d)_m$—$(C_3$-$C_{12}$ cycloalkyl), —$(R^d)_m$-phenyl, —$(R^d)_m$-(3-15 membered heterocyclyl), —$(R^d)_m$—$(C_1$-$C_6$ perfluoroalkyl), —$(R^d)_m$-halide, —$(R^d)_m$—CN, —$(R^d)_m$—C(O)$R^a$, —$(R^d)_m$—C(O)O$R^a$, —$(R^d)_m$—C(O)N$R^aR^b$, —$(R^d)_m$—O$R^a$, —$(R^d)_m$—OC(O)$R^a$, —$(R^d)_m$—OC(O)N$R^aR^b$, —$(R^d)_m$—O—S(O)$R^a$, —$(R^d)_m$—OS(O)$_2R^a$, —$(R^d)_m$—OS(O)$_2$N$R^aR^b$, —$(R^d)_m$—OS(O)N$R^aR^b$, —$(R^d)_m$—NO$_2$, —$(R^d)_m$—N$R^aR^b$, —$(R^d)_m$—N($R^a$)C(O)$R^b$, —$(R^d)_m$—N($R^a$)C(O)O$R^b$, —$(R^d)_m$—N($R^c$)C(O)N$R^aR^b$, —$(R^d)_m$—N($R^a$)S(O)$_2R^b$, —$(R^d)_m$—N($R^a$)S(O)$R^b$, —$(R^d)_m$—S$R^a$, —$(R^d)_m$—S(O)$R^a$, —$(R^d)_m$—S(O)$_2R^a$, —$(R^d)_m$—S(O)N$R^aR^b$, —$(R^d)_m$—S(O)$_2$N$R^aR^b$, —$(R^d)_m$—O—$(R^e)_m$—N$R^aR^b$ or —$(R^d)_m$—N$R^a$—$(R^e)$—O$R^b$;

wherein any of the said alkyl, alkenyl, alkynyl, $R^a$, $R^b$, $R^c$, $R^d$, $R^e$, $C_3$-$C_{12}$ cycloalkyl, aryl or 3-15 membered heterocyclyl are independently optionally further substituted by 0-3 $R^{12}$ groups, $R^6$ and $R^7$ are each independently H, $R^a$—O—$R^b$, $C_1$-$C_8$ alkyl, $C_2$-$C_8$ alkenyl, $C_2$-$C_8$ alkynyl, —$(R^d)_m$—$(C_3$-$C_{12}$ cycloalkyl), —$(R^d)_m$-phenyl, —$(R^d)_m$-(3-15 membered heterocyclyl), —$(R^d)_m$—$(C_1$-$C_6$ perfluoroalkyl), —$(R^d)_m$-halide, —$(R^d)_m$—CN, —$(R^d)_m$—C(O)$R^a$, —$(R^d)_m$—C(O)O$R^a$, —$(R^d)_m$—C(O)N$R^aR^b$, —$(R^d)_m$—O$R^a$, —$(R^d)_m$—OC(O)$R^a$, —$(R^d)_m$—OC(O)N$R^aR^b$, —$(R^d)_m$—O—S(O)$R^a$, —$(R^d)_m$—OS(O)$_2R^a$, —$(R^d)_m$—OS(O)$_2$N$R^aR^b$, —$(R^d)_m$—OS(O)N$R^aR^b$, —$(R^d)_m$—NO$_2$, —$(R^d)_m$—N$R^aR^b$, —$(R^d)_m$—N($R^a$)C(O)$R^b$, —$(R^d)_m$—N($R^a$)C(O)O$R^b$, —$(R^d)_m$—N($R^c$)C(O)N$R^aR^b$, —$(R^d)_m$—N($R^a$)S(O)$_2R^b$, —$(R^d)_m$—N($R^a$)S(O)$R^b$, —$(R^d)_m$—S$R^a$, —$(R^d)_m$—S(O)$R^a$, —$(R^d)_m$—S(O)$_2R^a$, —$(R^d)_m$—S(O)N$R^aR^b$, —$(R^d)_m$—S(O)$_2$N$R^aR^b$, —$(R^d)_m$—O—$(R^e)_m$—N$R^aR^b$ or —$(R^d)_m$—N$R^a$—$(R^e)$—O$R^b$; wherein $R^6$ and $R^7$ may together optionally cyclize to form a $C_3$-$C_7$ cycloalkyl and wherein any of the said alkyl, alkenyl, alkynyl, $R^a$, $R^b$, $R^c$, $R^d$, $R^e$, $C_3$-$C_{12}$ cycloalkyl, aryl or 3-15 membered heterocyclyl are independently optionally further substituted by 0-3 $R^{12}$ groups;

$R^8$ is H, $R^a$—O—$R^b$, $C_1$-$C_8$ alkyl, $C_2$-$C_8$ alkenyl, $C_2$-$C_8$ alkynyl, —$(R^d)_m$—$(C_3$-$C_{12}$ cycloalkyl), —$(R^d)_m$-phenyl, —$(R^d)_m$-(3-15 membered heterocyclyl), —$(R^d)_m$—$(C_1$-$C_6$ perfluoroalkyl), —$(R^d)_m$-halide, —$(R^d)_m$—CN, —$(R^d)_m$—C(O)$R^a$, —$(R^d)_m$—C(O)O$R^a$, —$(R^d)_m$—C(O)N$R^aR^b$, —$(R^d)_m$—O$R^a$, —$(R^d)_m$—OC(O)$R^a$, —$(R^d)_m$—OC(O)N$R^aR^b$, —$(R^d)_m$—O—S(O)$R^a$, —$(R^d)_m$—OS(O)$_2R^a$, —$(R^d)_m$—OS(O)$_2$N$R^aR^b$, —$(R^d)_m$—OS(O)N$R^aR^b$, —$(R^d)_m$—NO$_2$, —$(R^d)_m$—N$R^aR^b$, —$(R^d)_m$—N($R^a$)C(O)$R^b$, —$(R^d)_m$—N($R^a$)C(O)O$R^b$, —$(R^d)_m$—N($R^c$)C(O)N$R^aR^b$, —$(R^d)_m$—N($R^a$)S(O)$_2R^b$, —($(R^d)_m$—N($R^a$)S(O)$R^b$, —$(R^d)_m$—S$R^a$, —$(R^d)_m$—S(O)$R^a$, —$(R^d)_m$—S(O)$_2R^a$, —$(R^d)_m$—S(O)N$R^aR^b$, —$(R^d)_m$—S(O)$_2$N$R^aR^b$, —$(R^d)_m$—O—$(R^e)_m$—N$R^aR^b$ or —$(R^d)_m$—N$R^a$—$(R^e)$—O$R^b$; and wherein any of the said alkyl, alkenyl, alkynyl, $R^a$, $R^b$, $R^c$, $R^d$, $R^e$, $C_3$-$C_{12}$ cycloalkyl, phenyl, or 3-15 membered heterocyclyl are independently optionally further substituted by 1-3 groups selected from —F, $C_1$-$C_3$ alkyl, $C_1$-$C_3$ perfluoroalkyl, hydroxyl, $C_1$-$C_6$alkoxyl, or oxo;

$R^9$ and $R^{10}$ are each independently $C_1$-$C_2$ alkyl or can together cyclize to form a cyclopropyl or cyclobutyl;

each $R^{12}$ is independently H, $R^a$—O—$R^b$, $C_1$-$C_8$ alkyl, $C_2$-$C_8$ alkenyl, $C_2$-$C_8$ alkynyl, —$(R^d)_m$—$(C_3$-$C_{12}$ cycloalkyl), —$(R^d)_m$-phenyl, —$(R^d)_m$-(3-15 membered heterocyclyl), —(R$^d$)$_m$—(C$_1$-C$_6$ perfluoroalkyl), —(R$^d$)$_m$-halide, —(R$^d$)$_m$—CN, —(R$^d$)$_m$—C(O)R$^a$, —(R$^d$)$_m$—C(O)OR$^a$, —(R$^d$)$_m$—C(O)NR$^a$R$^b$, —(R$^d$)$_m$—OR$^a$, —(R$^d$)$_m$—OC(O)R$^a$, —(R$^d$)$_m$—OC(O)NR$^a$R$^b$, —(R$^d$)$_m$—O—S(O)R$^a$, —(R$^d$)$_m$—OS(O)$_2$R$^a$, —(R$^d$)$_m$—OS(O)$_2$NR$^a$R$^b$, —(R$^d$)$_m$—OS(O)NR$^a$R$^b$, —(R$^d$)$_m$—NO$_2$, —(R$^d$)$_m$—N$^a$R$^b$, —(R$^d$)$_m$—N(R$^a$)C(O)R$^b$, —(R$^d$)$_m$—N(R$^a$)C(O)OR$^b$, —(R$^d$)$_m$—N(R$^c$)C(O)NR$^a$R$^b$, —(R$^d$)$_m$—N(R$^a$)S(O)$_2$R$^b$, —(R$^d$)$_m$—N(R$^a$)S(O)R$^b$, —(R$^d$)$_m$—SR$^a$, —(R$^d$)$_m$—S(O)R$^a$, —(R$^d$)$_m$—S(O)$_2$R$^a$, —(R$^d$)$_m$—S(O)NR$^a$R$^b$, —(R$^d$)$_m$—S(O)$_2$NR$^a$R$^b$, —(R$^d$)$_m$—O—(R$^e$)$_m$—NR$^a$R$^b$ or —(R$^d$)$_m$—NR$^a$—(R$^e$)—OR$^b$; and wherein any of the said alkyl, alkenyl, alkynyl, R$^a$, R$^b$, R$^c$, R$^d$, R$^e$, C$_3$-C$_{12}$ cycloalkyl, phenyl, or 3-15 membered heterocyclyl, are independently optionally further substituted by 1-3 groups selected from —F, C$_1$-C$_3$ alkyl, C$_1$-C$_3$ perfluoroalkyl, hydroxyl, C$_1$-C$_6$alkoxyl or oxo;

each R$^a$, R$^b$ and R$^c$ is independently selected from H, C$_1$-C$_8$ alkyl, C$_2$-C$_8$ alkenyl, —(R$^d$)$_m$—(C$_3$-C$_8$ cycloalkyl), —(R$^d$)$_m$—(C$_3$-C$_8$ cycloalkenyl), C$_2$-C$_8$ alkynyl, —(R$^d$)$_m$-phenyl, or —(R$^d$)$_m$-(3-7 membered heterocyclyl), and each R$^a$, R$^b$ and R$^c$ is independently optionally further substituted by 1-3 groups selected from halide, hydroxyl, —CN, C$_1$-C$_6$ alkyl, C$_1$-C$_6$ perfluoroalkyl, C$_1$-C$_6$ alkoxyl and C$_1$-C$_6$ alkylamino; or, when connected to the same nitrogen, R$^a$ and R$^b$ may together optionally form a 3-7 membered heterocyclyl, which may optionally be further substituted by 0-3 groups selected from halide, hydroxyl, —CN, C$_1$-C$_6$ alkyl, C$_1$-C$_6$ perfluoroalkyl, C$_1$-C$_6$ alkoxyl or C$_1$-C$_6$ alkylamino;

each R$^d$ and R$^e$ is independently-(C$_1$-C$_3$ alkylene)-, —(C$_2$-C$_5$ alkenylene)-, or —(C$_2$-C$_5$ alkynylene)-;

and each m is independently 0 or 1;

with the proviso that when X is N, R$^6$ and R$^7$ are not both H, and that when X is C—R$^{11}$, R$^6$ and R$^7$ are both H;

or a pharmaceutically acceptable salt thereof.

Another embodiment provides a method of treating uveitis, wherein for the compound of Formula (A), R$^9$ and R$^{10}$ are both methyl. Another embodiment provides a method of treating uveitis, wherein for the compound of Formula (A), X is N and R$^6$ and R$^7$ are each independently H or C$_1$-C$_6$alkyl but are not both H. Another embodiment provides a method of treating uveitis, wherein for the compound of Formula (A), A is N and B is C. Another embodiment provides a method of treating uveitis, wherein for the compound of Formula (A), A is C and B is N. Another embodiment provides a method of treating uveitis, wherein for the compound of Formula (A), R$^6$ and R$^7$ are both methyl. Another embodiment provides a method of treating uveitis, wherein for the compound of Formula (A), R$^6$ is H and R$^7$ is methyl. Another embodiment provides a method of treating uveitis, wherein for the compound of Formula (A), R$^4$ is R$^a$—O—R$^b$, C$_1$-C$_8$ alkyl, C$_2$-C$_8$ alkenyl, C$_2$-C$_8$ alkynyl, —(R$^d$)$_m$—(C$_3$-C$_{12}$cycloalkyl), —(R$^d$)$_m$-phenyl, —(R$^d$)$_m$-(3-15 membered heterocyclyl), —(R$^d$)$_m$—(C$_1$-C$_6$perfluoroalkyl), —(R$^d$)$_m$-halide, —(R$^d$)$_m$—CN, —(R$^d$)$_m$—C(O)R$^a$, —(R$^d$)$_m$—C(O)OR$^a$, —(R$^d$)$_m$—C(O)NR$^a$R$^b$, —(R$^d$)$_m$—OR$^a$, —(R$^d$)$_m$—OC(O)R$^a$, —(R$^d$)$_m$—OC(O)NR$^a$R$^b$, —(R$^d$)$_m$—O—S(O)R$^a$, —(R$^d$)$_m$—OS(O)$_2$R$^a$, —(R$^d$)$_m$—OS(O)$_2$NR$^a$R$^b$, —(R$^d$)$_m$—OS(O)NR$^a$R$^b$, —(R$^d$)$_m$—NO$_2$, —(R$^d$)$_m$NR$^a$R$^b$, —(R$^d$)$_m$—N(R$^a$)C(O)R$^b$, —(R$^d$)$_m$—N(R$^a$)C(O)OR$^b$, —(R$^d$)$_m$—N(R$^c$)C(O)NR$^a$R$^b$, —(R$^d$)$_m$—N(R$^a$)S(O)$_2$R$^b$, —(R$^d$)$_m$—N(R$^a$)S(O)R$^b$, —(R$^d$)$_m$—SR$^a$, —(R$^d$)$_m$—S(O)R$^a$, —(R$^d$)$_m$—S(O)$_2$R$^a$, —(R$^d$)$_m$—S(O)NR$^a$R$^b$, —(R$^d$)$_m$—S(O)$_2$NR$^a$R$^b$, —(R$^d$)$_m$—O—(R$^e$)$_m$—NR$^a$R$^b$ or —(R$^d$)$_m$—NR$^a$—(R$^e$)—OR$^b$; wherein the said R$^a$, R$^b$, R$^c$, R$^d$, R$^e$, C$_3$-C$_{12}$ cycloalkyl, aryl, 3-15 membered heterocyclyl, are independently optionally further substituted by 0-3 R$^{12}$ groups. Another embodiment provides a method of treating uveitis, wherein for the compound of Formula (A), R$^4$ is methyl. Another embodiment provides a method of treating uveitis, wherein for the compound of Formula (A), R$^1$ is R$^a$—O—R$^b$, C$_1$-C$_8$ alkyl, C$_2$-C$_8$ alkenyl, C$_2$-C$_8$ alkynyl, —(R$^d$)$_m$—(C$_3$-C$_{12}$ cycloalkyl), —(R$^d$)$_m$-phenyl, —(R$^d$)$_m$-(3-15 membered heterocyclyl), —(R$^d$)$_m$—(C$_1$-C$_6$ perfluoroalkyl), —(R$^d$)$_m$-halide, —(R$^d$)$_m$—CN, —(R$^d$)$_m$—C(O)R$^a$, —(R$^d$)$_m$—C(O)OR$^a$, —(R$^d$)$_m$—C(O)NR$^a$R$^b$, —(R$^d$)$_m$—OR$^a$, —(R$^d$)$_m$—OC(O)R$^a$, —(R$^d$)$_m$—OC(O)NR$^a$R$^b$, —(R$^d$)$_m$—O—S(O)R$^a$, —(R$^d$)$_m$—OS(O)$_2$R$^a$, —(R$^d$)$_m$—OS(O)$_2$NR$^a$R$^b$, —(R$^d$)$_m$—OS(O)NR$^a$R$^b$, —(R$^d$)$_m$—NO$_2$, —(R$^d$)$_m$—NR$^a$R$^b$, —(R$^d$)$_m$—N(R$^a$)C(O)R$^b$, —(R$^d$)$_m$—N(R$^a$)C(O)OR$^b$, —(R$^d$)$_m$—N(R$^c$)C(O)NR$^a$R$^b$, —(R$^d$)$_m$—N(R$^a$)S(O)$_2$R$^b$, —(R$^d$)$_m$—N(R$^a$)S(O)R$^b$, —(R$^d$)$_m$—SR$^a$, —(R$^d$)$_m$—S(O)R$^a$, —(R$^d$)$_m$—S(O)$_2$R$^a$, —(R$^d$)$_m$—S(O)NR$^a$R$^b$, —(R$^d$)$_m$—S(O)$_2$NR$^a$R$^b$, —(R$^d$)$_m$—O—(R$^e$)$_m$—NR$^a$R$^b$ or —(R$^d$)$_m$—NR$^a$—(R$^e$)—OR$^b$; wherein the said —R$^a$, R$^b$, R$^c$, R$^d$, R$^e$, C$_3$-C$_{12}$ cycloalkyl, aryl, the said 3-15 membered heterocyclyl, are independently optionally further substituted by 0-3 R$^{12}$ groups. Another embodiment provides a method of treating uveitis, wherein for the compound of Formula (A), R$^1$ is —(R$^d$)$_m$—OR$^a$, C$_1$-C$_8$ alkyl, or —(R$^d$)$_m$—NR$^a$R$^b$. Another embodiment provides a method of treating uveitis, wherein for the compound of Formula (A), R$^8$ is R$^a$—O—R$^b$, C$_1$-C$_8$ alkyl, C$_2$-C$_8$ alkenyl, C$_2$-C$_8$ alkynyl, —(R$^d$)$_m$—(C$_3$-C$_{12}$ cycloalkyl), —(R$^d$)$_m$-phenyl, —(R$^d$)$_m$-(3-15 membered heterocyclyl), —(R$^d$)$_m$—(C$_1$-C$_6$ perfluoroalkyl), —(R$^d$)$_m$-halide, —(R$^d$)$_m$—CN, —(R$^d$)$_m$—OR$^a$, or —(R$^d$)$_m$—NR$^a$R$^b$. Another embodiment provides a method of treating uveitis, wherein for the compound of Formula (A), each R$^d$ and R$^e$ is independently an —(C$_1$-C$_3$ alkylene).

One embodiment provides a method of treating uveitis in a subject in need thereof comprising administering to the subject a composition comprising a compound, or a pharmaceutically acceptable salt thereof, having formula (B):

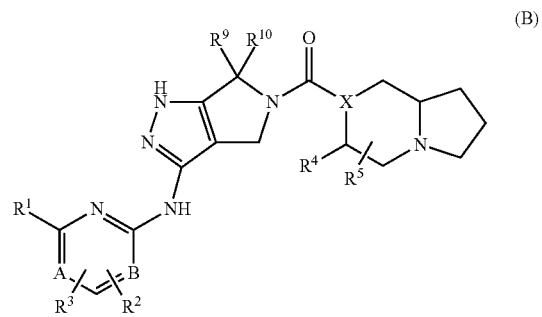

(B)

wherein
X is C—R$^{11}$ or N, wherein R$^{11}$ is H, halo, OH, C$_1$-C$_3$alkyl, CF$_3$, or CN;
A and B are independently C or N;
R$^1$ is R$^a$—O—R$^b$, C$_1$-C$_8$ alkyl, C$_2$-C$_8$ alkenyl, C$_2$-C$_8$ alkynyl, —(R$^d$)$_m$—(C$_3$-C$_{12}$ cycloalkyl), —(R$^d$)$_m$-phenyl, —(R$^d$)$_m$-(3-15 membered heterocyclyl), —(R$^d$)$_m$—(C$_1$-C$_6$ perfluoroalkyl), —(R$^d$)$_m$-halide, —(R$^d$)$_m$—CN, —(R$^d$)$_m$—C(O)R$^a$, —(R$^d$)$_m$—C(O)OR$^a$, —(R$^d$)$_m$—C(O)NR$^a$R$^b$, —(R$^d$)$_m$—OR$^a$, —(R$^d$)$_m$—OC(O)R$^a$, —(R$^d$)$_m$—OC(O)NR$^a$R$^b$, —(R$^d$)$_m$—O—S(O)R$^a$, —(R$^d$)$_m$—OS(O)$_2$R$^a$, —(R$^d$)$_m$—OS(O)$_2$NR$^a$R$^b$, —(R$^d$)$_m$—OS(O)NR$^a$R$^b$, —(R$^d$)$_m$—NO$_2$, —(R$^d$)$_m$—NR$^a$R$^b$, —(R$^d$)$_m$—N(R$^a$)C(O)R$^b$, —(R$^d$)$_m$—N(R$^a$)C(O)OR$^b$, —(R$^d$)$_m$—N(R$^c$)C(O)NR$^a$R$^b$, —(R$^d$)$_m$—N(R$^a$)S(O)$_2$R$^b$, —(R$^d$)$_m$—N(R$^a$)S(O)R$^b$, —(R$^d$)$_m$—SR$^a$, —(R$^d$)$_m$—S(O)R$^a$, —(R$^d$)$_m$—S(O)$_2$R$^a$, —(R$^d$)$_m$—S(O)NR$^a$R$^b$, —(R$^d$)$_m$—S(O)$_2$NR$^a$R$^b$, —(R$^d$)$_m$—O—(R$^e$)$_m$—NR$^a$R$^b$ or —(R$^d$)$_m$—NR$^a$—(R$^e$)—OR$^b$; and wherein any of the said alkyl, alkenyl, alkynyl, R$^a$, R$^b$, R$^c$, R$^d$, R$^e$, C$_3$-C$_{12}$ cycloalkyl, phenyl or 3-15 membered heterocyclyl, may independently be further optionally substituted by 0-3 R$^{12}$ groups;

R$^2$ and R$^3$ are each independently selected from H, R$^a$—O—R$^b$, C$_1$-C$_8$ alkyl, C$_2$-C$_8$ alkenyl, C$_2$-C$_8$ alkynyl, —(R$^d$)$_m$—(C$_3$-C$_{12}$ cycloalkyl), —(R$^d$)$_m$-phenyl, —(R$^d$)$_m$-(3-15 membered heterocyclyl), —(R$^d$)$_m$—(C$_1$-C$_6$ perfluoroalkyl), —(R$^d$)$_m$-halide, —(R$^d$)$_m$—CN, —(R$^d$)$_m$—C(O)R$^a$, —(R$^d$)$_m$—C(O)OR$^a$, —(R$^d$)$_m$—C(O)NR$^a$R$^b$, —(R$^d$)$_m$—OR$^a$, —(R$^d$)$_m$—OC(O)R$^a$, —(R$^d$)$_m$—OC(O)NR$^a$R$^b$, —(R$^d$)$_m$—O—S(O)R$^a$, —(R$^d$)$_m$—OS(O)$_2$R$^a$, —(R$^d$)$_m$—OS(O)$_2$NR$^a$R$^b$, —(R$^d$)$_m$—OS(O)NR$^a$R$^b$, —(R$^d$)$_m$—NO$_2$, —(R$^d$)$_m$—NR$^a$R$^b$, —(R$^d$)$_m$—N(R$^a$)C(O)R$^b$, —(R$^d$)$_m$—N(R$^a$)C(O)OR$^b$, —(R$^d$)$_m$—N(R$^c$)C(O)NR$^a$R$^b$, —(R$^d$)$_m$—N(R$^a$)S(O)$_2$R$^b$, —(R$^d$)$_m$—N(R$^a$)S(O)R$^b$, —(R$^d$)$_m$—SR$^a$, —(R$^d$)$_m$—S(O)R$^a$, —(R$^d$)$_m$—S(O)$_2$R$^a$, —(R$^d$)$_m$—S(O)NR$^a$R$^b$, —(R$^d$)$_m$—S(O)$_2$NR$^a$R$^b$, —(R$^d$)$_m$—O—(R$^e$)$_m$—NR$^a$R$^b$ or —(R$^d$)$_m$—NR$^a$—(R$^e$)—OR$^b$; wherein R$^2$ and R$^3$ may together optionally cyclize to form a saturated or unsaturated 3-7 membered heterocyclyl fused to the 6-membered N-containing heteroaryl to which they are attached; and wherein any of the said alkyl, alkenyl, alkynyl, R$^a$, R$^b$, R$^c$, R$^d$, R$^e$, C$_3$-C$_{12}$ cycloalkyl, phenyl or 3-15 membered heterocyclyl, may independently be further optionally substituted by 0-3 R$^{12}$ groups;

R$^4$ and R$^5$ are each independently selected from H, R$^a$—O—R$^b$, C$_1$-C$_8$ alkyl, C$_2$-C$_8$ alkenyl, C$_2$-C$_8$ alkynyl, —(R$^d$)$_m$—(C$_3$-C$_{12}$ cycloalkyl), —(R$^d$)$_m$-phenyl, —(R$^d$)$_m$-(3-15 membered heterocyclyl), —(R$^d$)$_m$—(C$_1$-C$_6$ perfluoroalkyl), —(R$^d$)$_m$-halide, —(R$^d$)$_m$—CN, —(R$^d$)$_m$—C(O)R$^a$, —(R$^d$)$_m$—C(O)OR$^a$, —(R$^d$)$_m$—C(O)NR$^a$R$^b$, —(R$^d$)$_m$—OR$^a$, —(R$^d$)$_m$—OC(O)R$^a$, —(R$^d$)$_m$—OC(O)NR$^a$R$^b$, —(R$^d$)$_m$—O—S(O)R$^a$, —(R$^d$)$_m$—OS(O)$_2$R$^a$, —(R$^d$)$_m$—OS(O)$_2$NR$^a$R$^b$, —(R$^d$)$_m$—OS(O)NR$^a$R$^b$, —(R$^d$)$_m$—NO$_2$, —(R$^d$)$_m$—NR$^a$R$^b$, —(R$^d$)$_m$—N(R$^a$)C(O)R$^b$, (R$_d$)$_m$—N(R$^a$)C(O)OR$^b$, —(R$^d$)$_m$—N(R$^c$)C(O)NR$^a$R$^b$, —(R$^d$)$_m$—N(R$^a$)S(O)$_2$R$^b$, —(R$^d$)$_m$—N(R$^a$)S(O)R$^b$, —(R$^d$)$_m$—SR$^a$, —(R$^d$)$_m$—S(O)R$^a$, —(R$^d$)$_m$—S(O)$_2$R$^a$, —(R$^d$)$_m$—S(O)NR$^a$R$^b$, —(R$^d$)$_m$—S(O)$_2$NR$^a$R$^b$, —(R$^d$)$_m$—O—(R$^e$)$_m$—NR$^a$R$^b$ or —(R$^d$)$_m$—NR$^a$—(R$^e$)—OR$^b$; wherein any of the said alkyl, alkenyl, alkynyl, R$^a$, R$^b$, R$^c$, R$_d$, R$^e$, C$_3$-C$_{12}$ cycloalkyl, aryl or 3-15 membered heterocyclyl are independently optionally further substituted by 0-3 R$^{12}$ groups, R$^8$ is H, R$^a$—O—R$^b$, C$_1$-C$_8$ alkyl, C$_2$-C$_8$ alkynyl, —(R$^d$)$_m$—(C$_3$-C$_{12}$ cycloalkyl), —(R$^d$)$_m$-phenyl, —(R$^d$)$_m$-(3-15 membered heterocyclyl), —(R$^d$)$_m$—(C$_1$-C$_6$ perfluoroalkyl), —(R$^d$)$_m$-halide, —(R$^d$)$_m$—CN, —(R$^d$)$_m$—C(O)R$^a$, —(R$^d$)$_m$—C(O)OR$^a$, —(R$^d$)$_m$—C(O)NR$^a$R$^b$, —(R$^d$)$_m$—OR$^a$, —(R$^d$)$_m$—OC(O)R$^a$, —(R$^d$)$_m$—OC(O)NR$^a$R$^b$, —(R$^d$)$_m$—O—S(O)R$^a$, —(R$^d$)$_m$—OS(O)$_2$R$^a$, —(R$^d$)$_m$—OS(O)$_2$NR$^a$R$^b$, —(R$^d$)$_m$—OS(O)NR$^a$R$^b$, —(R$^d$)$_m$—NO$_2$, —(R$^d$)$_m$—NR$^a$R$^b$, —(R$^d$)$_m$—N(R$^a$)C(O)R$^b$, —(R$^d$)$_m$—N(R$^a$)C(O)OR$^b$, —(R$^d$)$_m$—N(R$^c$)C(O)NR$^a$R$^b$, —(R$^d$)$_m$—N(R$^a$)S(O)$_2$R$^b$, —((R$^d$)$_m$—N(R$^a$)S(O)R$^b$, —(R$^d$)$_m$—SR$^a$, —(R$^d$)$_m$—S(O)R$^a$, —(R$^d$)$_m$—S(O)$_2$R$^a$, —(R$^d$)$_m$—S(O)NR$^a$R$^b$, —(R$^d$)$_m$—S(O)$_2$NR$^a$R$^b$, —(R$^d$)$_m$—O—(R$^e$)$_m$—NR$^a$R$^b$ or —(R$^d$)$_m$—NR$^a$—(R$^e$)—OR$^b$; and wherein any of the said alkyl, alkenyl, alkynyl, R$^a$, R$^b$, R$^c$, R$^d$, R$^e$, C$_3$-C$_{12}$ cycloalkyl, phenyl, or 3-15 membered heterocyclyl are independently optionally further substituted by 1-3 groups selected from —F, C$_1$-C$_3$ alkyl, C$_1$-C$_3$ perfluoroalkyl, hydroxyl, C$_1$-C$_6$alkoxyl, or oxo;

R$^9$ and R$^{10}$ are each independently C$_1$-C$_2$ alkyl or can together cyclize to form a cyclopropyl or cyclobutyl;

each R$^{12}$ is independently H, R$^a$—O—R$^b$, C$_1$-C$_8$ alkyl, C$_2$-C$_8$ alkenyl, C$_2$-C$_8$ alkynyl, —(R$^d$)$_m$—(C$_3$-C$_{12}$ cycloalkyl), —(R$^d$)$_m$-phenyl, —(R$^d$)$_m$-(3-15 membered heterocyclyl), —(R$^d$)$_m$—(C$_1$-C$_6$ perfluoroalkyl), —(R$^d$)$_m$-halide, —(R$^d$)$_m$—CN, —(R$^d$)$_m$—C(O)R$^a$, —(R$^d$)$_m$—C(O)OR$^a$, —(R$^d$)$_m$—C(O)NR$^a$R$^b$, —(R$^d$)$_m$—OR$^a$, —(R$^d$)$_m$—OC(O)R$^a$, —(R$^d$)$_m$—OC(O)NR$^a$R$^b$, —(R$^d$)$_m$—O—S(O)R$^a$, —(R$^d$)$_m$—OS(O)$_2$R$^a$, —(R$^d$)$_m$—OS(O)$_2$NR$^a$R$^b$, —(R$^d$)$_m$—OS(O)NR$^a$R$^b$, —(R$^d$)$_m$—NO$_2$, —(R$^d$)$_m$—NR$^a$R$^b$, —(R$^d$)$_m$—N(R$^a$)C(O)R$^b$, —(R$^d$)$_m$—N(R$^a$)C(O)OR$^b$, —(R$^d$)$_m$—N(R$^c$)C(O)NR$^a$R$^b$, —(R$^d$)$_m$—N(R$^a$)S(O)$_2$R$^b$, —(R$^d$)$_m$—N(R$^a$)S(O)R$^b$, —(R$^d$)$_m$—SR$^a$, —(R$^d$)$_m$—S(O)R$^a$, —(R$^d$)$_m$—S(O)$_2$R$^a$, —(R$^d$)$_m$—S(O)NR$^a$R$^b$, —(R$^d$)$_m$—S(O)$_2$NR$^a$R$^b$, —(R$^d$)$_m$—O—(R$^e$)$_m$—NR$^a$R$^b$ or —(R$^d$)$_m$—NR$^a$—(R$^e$)—OR$^b$; and wherein any of the said alkyl, alkenyl, alkynyl, R$^a$, R$^b$, R$^c$, R$^d$, R$^e$, C$_3$-C$_{12}$ cycloalkyl, phenyl, or 3-15 membered heterocyclyl, are independently optionally further substituted by 1-3 groups selected from —F, C$_1$-C$_3$ alkyl, C$_1$-C$_3$ perfluoroalkyl, hydroxyl, C$_1$-C$_6$alkoxyl or oxo;

each R$^a$, R$^b$ and R$^c$ is independently selected from H, C$_1$-C$_8$ alkyl, C$_2$-C$_8$ alkenyl, —(R$^d$)$_m$—(C$_3$-C$_8$ cycloalkyl), —(R$^d$)$_m$—(C$_3$-C$_8$ cycloalkenyl), C$_2$-C$_8$ alkynyl, —(R$^d$)$_m$-phenyl, or —(R$^d$)$_m$-(3-7 membered heterocyclyl), and each R$^a$, R$^b$ and R$^c$ is independently optionally further substituted by 1-3 groups selected from halide, hydroxyl, —CN, C$_1$-C$_6$ alkyl, C$_1$-C$_6$ perfluoroalkyl, C$_1$-C$_6$ alkoxyl and C$_1$-C$_6$ alkylamino; or, when connected to the same nitrogen, R$^a$ and R$^b$ may together optionally form a 3-7 membered heterocyclyl, which may optionally be further substituted by 0-3 groups selected from halide, hydroxyl, —CN, C$_1$-C$_6$ alkyl, C$_1$-C$_6$ perfluoroalkyl, C$_1$-C$_6$ alkoxyl or C$_1$-C$_6$ alkylamino;

each R$^d$ and R$^e$ is independently -(C$_1$-C$_3$ alkylene)-, —(C$_2$-C$_5$ alkenylene)-, or —(C$_2$-C$_5$ alkynylene)-;

and each m is independently 0 or 1, or a pharmaceutically acceptable salt thereof.

Another embodiment provides a method of treating uveitis, wherein for the compound of Formula (B), A is N and B is C. Another embodiment provides a method of treating uveitis, wherein for the compound of Formula (B), R$^9$ and R$^{10}$ are both methyl. Another embodiment provides a method of treating uveitis, wherein for the compound of Formula (B), R$^4$ is —(R$^d$)$_m$—OR$^a$, C$_1$-C$_8$ alkyl, C$_2$-C$_8$ alkenyl or C$_2$-C$_8$ alkynyl. Another embodiment provides a method of treating uveitis, wherein for the compound of Formula (B), R$^4$ is methyl. Another embodiment provides a method of treating uveitis, wherein for the compound of Formula (B), R$^1$ is —(R$^d$)$_m$—OR$^a$, C$_1$—C alkyl, or —(R$^d$)m NR$^a$R$^b$. Another embodiment provides a method of treating uveitis, wherein for the compound of Formula (B), each R$^d$ and R$^e$ is independently an —(C$_1$-C$_3$ alkylene)-.

Encephalitis

One embodiment provides a method of treating encephalitis in a subject in need thereof comprising administering to the subject a composition comprising a compound, or a pharmaceutically acceptable salt thereof, selected from the group consisting of:

$N^4$-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-N2-ethyl-5-fluoropyrimidine-2,4-diamine, $N^4$-(6,6-dimethyl-5-{[(2 S)-2,4,5,5-tetramethylpiperazin-1-yl]carbonyl}-1,4,5,6-tetrahydropyrrolo[3,4-c]pyrazol-3-yl)-5-fluoro-$N^2,N^2$-dimethylpyrimidine-2,4-diamine, $N^2$-cyclopropyl-N4-(6,6-dimethyl-5-{[(2 S)-2,4,5,5-tetramethylpiperazin-1-yl]carbonyl}-1,4,5,6-tetrahydropyrrolo[3,4-c]pyrazol-3-yl)-5-fluoropyrimidine-2,4-diamine, $N^4$-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-5-fluoro-$N^2$-methylpyrimidine-2,4-diamine, $N^4$-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-5-fluoro-$N^2$-isopropylpyrimidine-2,4-diamine, $N^4$-(6,6-dimethyl-5-{[(2 S)-2,4,5,5-tetramethylpiperazin-1-yl]carbonyl}-1,4,5,6-tetrahydropyrrolo[3,4-c]pyrazol-3-yl)-$N^2$-ethylpyrimidine-2,4-diamine, $N^4$-(6,6-dimethyl-5-{[(2 S)-2,4,5,5-tetramethylpiperazin-1-yl]carbonyl}-1,4,5,6-tetrahydropyrrolo[3,4-c]pyrazol-3-yl)-$N^2,N^2$-dimethylpyrimidine-2,4-diamine, 5-{[(8S)-6, 8-dimethyl-6,9-diazaspiro[4.5]dec-9-yl]carbonyl}-N-(5-fluoro-2-methylpyrimidin-4-yl)-6,6-dimethyl-1,4,5,6-tetrahydropyrrolo[3,4-c]pyrazol-3-amine, $N^4$-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-$N^2$-ethyl-5-fluoropyrimidine-2,4-diamine, $N^4$-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)-$N^2$-ethyl-5-fluoropyrimidine-2,4-diamine, $N^2$-ethyl-5-fluoro-$N^4$-(5-{[(2S,5R)-4-(3-methoxypropyl)-2,5-dimethylpiperazin-1-yl]carbonyl})-6,6-dimethyl-1,4,5,6-tetrahydropyrrolo[3,4-c]pyrazol-3-yl)pyrimidine-2,4-diamine, $N^4$-(6,6-dimethyl-5-{[(2S,5R)-2,4,5-trimethylpiperazin-1-yl]carbonyl}-1,4,5,6-tetrahydropyrrolo[3,4-c]pyrazol-3-yl)-$N^2$-ethyl-5-fluoropyrimidine-2,4-diamine, 4-[(6,6-dimethyl-5-{[(2S,5R)-2,4,5-trimethylpiperazin-1-yl]carbonyl}-1,4,5,6-tetrahydropyrrolo[3,4-c]pyrazol-3-yl)amino]pyrimidine-2-carbonitrile, N-(2-ethyl-5-fluoropyrimidin-4-yl)-6,6-dimethyl-5-{[(2S)-2,4,5,5-tetramethylpiperazin-1-yl]carbonyl})-1,4,5,6-tetrahydropyrrolo[3,4-c]pyrazol-3-amine, N-(2-ethyl-5-fluoropyrimidin-4-yl)-5-{[(2S,5R)-4-(3-methoxypropyl)-2,5-dimethylpiperazin-1-yl]carbonyl}-6,6-dimethyl-1,4,5,6-tetrahydropyrrolo[3,4-c]pyrazol-3-amine, 2-((5S)-4-{[3-[(2-ethyl-5-fluoropyrimidin-4-yl)amino]-6,6-dimethyl-4,6-dihydropyrrolo[3,4-c]pyrazol-5(1H)-yl]carbonyl}-1,5-dimethylpiperazin-2-yl)ethanol, 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, N-(5-fluoro-2-methylpyrimidin-4-yl)-6,6-dimethyl-5-{[(2S)-2,4,5,5-tetramethylpiperazin-1-yl]carbonyl})-1,4,5,6-tetrahydropyrrolo[3,4-c]pyrazol-3-amine, N-(5-fluoro-2-propylpyrimidin-4-yl)-6,6-dimethyl-5-{[(2 S)-2,4,5,5-tetramethylpiperazin-1-yl]carbonyl})-1,4,5,6-tetrahydropyrrolo[3,4-c]pyrazol-3-amine, N-(5-fluoro-2-isopropylpyrimidin-4-yl)-6,6-dimethyl-5-{[(2S)-2,4,5,5-tetramethylpiperazin-1-yl]carbonyl})-1,4,5,6-tetrahydropyrrolo[3,4-c]pyrazol-3-amine, N-[5-fluoro-2-(methoxymethyl)pyrimidin-4-yl]-6,6-dimethyl-5-{[(2S)-2,4,5,5-tetramethylpiperazin-1-yl]carbonyl})-1,4,5,6-tetrahydropyrrolo[3,4-c]pyrazol-3-amine, 5-{[(2S,5R)-2,5-dimethyl-4-(tetrahydro-2H-pyran-4-ylmethyl)piperazin-1-yl]carbonyl}-N-(2-ethyl-5-fluoropyrimidin-4-yl)-6,6-dimethyl-1,4,5,6-tetrahydropyrrolo[3,4-c]pyrazol-3-amine, 5-{[(2S,5R)-2,5-dimethyl-4-(tetrahydro-2H-pyran-4-yl)piperazin-1-yl]carbonyl)}-N-(4-methoxypyrimidin-2-yl)-6,6-dimethyl-1,4,5,6-tetrahydropyrrolo[3,4-c]pyrazol-3-amine, 5-{[(2S,5R)-2,5-dimethyl-4-(tetrahydro-2H-pyran-4-yl)piperazin-1-yl]carbonyl}-6,6-dimethyl-N-(4-methylpyrimidin-2-yl)-1,4,5,6-tetrahydropyrrolo[3,4-c]pyrazol-3-amine, 5-{[(2S,5R)-2,5-dimethyl-4-(tetrahydro-2H-pyran-4-yl)piperazin-1-yl]carbonyl}-6,6-dimethyl-N-[4-(trifluoromethyl)pyrimidin-2-yl]-1,4,5,6-tetrahydropyrrolo[3,4-c]pyrazol-3-amine, 5-{[(2S,5R)-2,5-dimethyl-4-(tetrahydro-2H-pyran-4-ylmethyl)piperazin-1-yl]carbonyl}-6,6-dimethyl-N-(4-methylpyrimidin-2-yl)-1,4,5,6-tetrahydropyrrolo[3,4-c]pyrazol-3-amine, N-(2-ethoxy-5-fluoropyrimidin-4-yl)-6,6-dimethyl-5-{[(2S,5R)-2,4,5-trimethylpiperazin-1-yl]carbonyl})-1,4,5,6-tetrahydropyrrolo[3,4-c]pyrazol-3-amine, N-(2-ethoxy-5-fluoropyrimidin-4-yl)-6,6-dimethyl-5-{[4-ethyl(2S,5R)-2,5-dimethylpiperazin-1-yl]carbonyl})-1,4,5,6-tetrahydropyrrolo[3,4-c]pyrazol-3-amine, N-(2-ethoxy-5-fluoropyrimidin-4-yl)-6,6-dimethyl-5-{[(2S)-2,4,5,5-tetramethylpiperazin-1-yl]carbonyl})-1,4,5,6-tetrahydropyrrolo[3,4-c]pyrazol-3-amine, N-(2-ethoxy-5-fluoropyrimidin-4-yl)-5-{[(2S,5R)-4-(2-methoxyethyl)-2,5-dimethylpiperazin-1-yl]carbonyl}-6,6-dimethyl-1,4,5,6-tetrahydropyrrolo[3,4-c]pyrazol-3-amine, N-(2-ethoxy-5-fluoropyrimidin-4-yl)-5-{[(2S,5R)-4-(3-methoxypropyl)-2,5-dimethylpiperazin-1-yl]carbonyl}-6,6-dimethyl-1,4,5,6-tetrahydropyrrolo[3,4-c]pyrazol-3-amine, N-[5-fluoro-2-(2,2,2-trifluoroethoxy)pyrimidin-4-yl]-5-{[(2S,5R)-4-(3-methoxypropyl)-2,5-dimethylpiperazin-1-yl]carbonyl}-6,6-dimethyl-1,4,5,6-tetrahydropyrrolo[3,4-c]pyrazol-3-amine, N-[5-fluoro-2-(2,2,2-trifluoroethoxy)pyrimidin-4-yl]-6,6-dimethyl-5-{[(2S,5R)-2,4,5-trimethylpiperazin-1-yl]carbonyl}-1,4,5,6-tetrahydropyrrolo[3,4-c]pyrazol-3-amine, N-[5-fluoro-2-(2,2,2-trifluoroethoxy)pyrimidin-4-yl]-6,6-dimethyl-5-{[(2S)-2,4,5,5-tetramethylpiperazin-1-yl]carbonyl})-1,4,5,6-tetrahydropyrrolo[3,4-c]pyrazol-3-amine, 5-{[(2S,5R)-2,5-dimethyl-4-(tetrahydro-2H-pyran-4-ylmethyl)piperazin-1-yl]carbonyl}-N-(2-ethoxy-5-fluoropyrimidin-4-yl)-6,6-dimethyl-1,4,5,6-tetrahydropyrrolo[3,4-c]pyrazol-3-amine, 5-{[(2S,5R)-2,5-dimethyl-4-(tetrahydro-2H-pyran-4-yl)piperazin-1-yl]carbonyl}-N-(2-ethoxy-5-fluoropyrimidin-4-yl)-6,6-dimethyl-1,4,5,6-tetrahydropyrrolo[3,4-c]pyrazol-3-amine, 2-((5S)-4-{[3-[(2-ethoxy-5-fluoropyrimidin-4-yl)amino]-6,6-dimethyl-4,6-dihydropyrrolo[3,4-c]pyrazol-5(1H)-yl]carbonyl}-1,5-dimethylpiperazin-2-yl)ethanol, 2-((5S)-4-{[3-[(2-ethoxy-5-fluoropyrimidin-4-yl)amino]-6,6-dimethyl-4,6-dihydropyrrolo[3,4-c]pyrazol-5(1H)-yl]carbonyl}-1,5-dimethylpiperazin-2-yl)ethanol, 5-[(4-fluoro-1-methylpiperidin-4-yl)carbonyl]-N-[5-fluoro-2-(2,2,2-trifluoroethoxy)pyrimidin-4-yl]-6,6-dimethyl-1,4,5,6-tetrahydropyrrolo[3,4-c]pyrazol-3-amine, 5-{[(2S,5R)-2,5-dimethyl-4-(tetrahydro-2H-pyran-4-ylmethyl)piperazin-1-yl]carbonyl}-N-[5-fluoro-2-(methoxymethyl)pyrimidin-4-yl]-6,6-dimethyl-1,4,5,6-tetrahydropyrrolo[3,4-c]pyrazol-3-amine, and 2-((5S)-4-{[3-{[5-fluoro-2-(methoxymethyl)pyrimidin-4-yl]amino}-6,6-dimethyl-4,6-dihydropyrrolo[3,4-c]pyrazol-5(1H)-yl]carbonyl}-1,5-dimethylpiperazin-2-yl)ethanol.

Another embodiment provides the method of treating encephalitis, wherein the compound is $N^4$-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-$N^2$-ethyl-5-fluoropyrimidine-2,4-diamine, or a pharmaceutically acceptable salt thereof. Another embodiment provides the method of treating encephalitis, wherein the compound is $N^4$-(5-{[(2S,5R)-2,5-dimethyl-4-(tetrahydro-2H-pyran-4-yl)piperazin-1-yl]carbonyl)}-6,6-dimethyl-1,4,5,6-tetrahydropyrrolo[3,4-c]pyrazol-3-yl)-$N^2$-ethyl-5-fluoropyrimidine-2,4-diamine, or a pharmaceutically acceptable salt thereof. Another embodiment provides the method of treating encephalitis, wherein the compound is 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof. Another embodiment provides the method of treating encephalitis, wherein the compound is 5-{[(2S,5R)-2,5-dimethyl-4-(tetrahydro-2H-pyran-4-ylmethyl)piperazin-1-yl]carbonyl}-N-(2-ethyl-5-fluoropyrimidin-4-yl)-6,6-dimethyl-1,4,5,6-tetrahydropyrrolo[3,4-c]pyrazol-3-amine, or a pharmaceutically acceptable salt thereof. Another embodiment provides the method of treating encephalitis, wherein the compound is 5-{[(2S,5R)-2,5-dimethyl-4-(tetrahydro-2H-pyran-4-yl)piperazin-1-yl]carbonyl}-N-(4-methoxypyrimidin-2-yl)-6,6-dimethyl-1,4,5,6-tetrahydropyrrolo[3,4-c]pyrazol-3-amine, or a pharmaceutically acceptable salt thereof. Another embodiment provides the method of treating encephalitis, wherein the compound is 5-{[(2S,5R)-2,5-dimethyl-4-(tetrahydro-2H-pyran-4-yl)piperazin-1-yl]carbonyl}-6,6-dimethyl-N-[4-(trifluoromethyl)pyrimidin-2-yl]-1,4,5,6-tetrahydropyrrolo[3,4-c]pyrazol-3-amine, or a pharmaceutically acceptable salt thereof. Another embodiment provides the method of treating encephalitis, wherein the compound is 5-{[(2S,5R)-2,5-dimethyl-4-(tetrahydro-2H-pyran-4-yl)piperazin-1-yl]carbonyl}-N-(2-ethoxy-5-fluoropyrimidin-4-yl)-6,6-dimethyl-1,4,5,6-tetrahydropyrrolo[3,4-c]pyrazol-3-amine, or a pharmaceutically acceptable salt thereof. Another embodiment provides the method of treating encephalitis, wherein the compound is $N^4$-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-N2-ethyl-5-fluoropyrimidine-2,4-diamine, or a pharmaceutically acceptable salt thereof. Another embodiment provides the method of treating encephalitis, wherein the compound is $N^4$-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-$N^2$-ethylpyrimidine-2,4-diamine, or a pharmaceutically acceptable salt thereof.

Another embodiment provides the method of treating encephalitis, wherein the encephalitis is autoimmune encephalitis, acute disseminated encephalitis, acute demyelinating encephalitis, NMDA receptor associated encephalitis, voltage-gated potassium channel-complex antibody derived encephalitis, hashimoto's encephalitis, or Rasmussen encephalitis.

One embodiment provides a method of treating encephalitis in a subject in need thereof comprising administering to the subject a composition comprising a compound having the formula 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof, and a pharmaceutically acceptable excipient.

One embodiment provides a method of treating encephalitis in a subject in need thereof comprising administering to the subject a composition comprising a compound, or a pharmaceutically acceptable salt thereof, selected from the group consisting of:

$N^2$-(cyclopropylmethyl)-$N^4$-(6,6-dimethyl-5-{[(2 S)-2,4,5,5-tetramethylpiperazin-1-yl]carbonyl})-1,4,5,6-tetrahydropyrrolo[3,4-c]pyrazol-3-yl)-5-fluoropyrimidine-2,4-diamine;

$N^4$-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-5-fluoro-$N^2$-isobutylpyrimidine-2,4-diamine;

5-{[(2S,5R)-4-ethyl-2,5-dimethylpiperazin-1-yl]carbonyl)}- N-(5-fluoro-2-methoxypyrimidin-4-yl)-6,6-dimethyl-1,4,5,6-tetrahydropyrrolo[3,4-c]pyrazol-3-amine;

5-{[(2S,5R)-4-ethyl-2,5-dimethylpiperazin-1-yl]carbonyl)}-N-(5-fluoro-2-methylpyrimidin-4-yl)-6,6-dimethyl-1,4,5,6-tetrahydropyrrolo[3,4-c]pyrazol-3-amine;

5-{[(2S,5R)-4-ethyl-2,5-dimethylpiperazin-1-yl]carbonyl)}-N-(5-fluoro-2,6-dimethylpyrimidin-4-yl)-6,6-dimethyl-1,4,5,6-tetrahydropyrrolo[3,4-c]pyrazol-3-amine;

2(S),5(S)-{[dimethyl-4-methylpiperazin-1-yl]carbonyl}-N-(5-fluoro-2-methylpyrimidin-4-yl)-6,6-dimethyl-1,4,5,6-tetrahydropyrrolo[3,4-c]pyrazol-3-amine;

[3-(5-fluoro-2-methyl-pyrimidin-4-ylamino)-6,6-dimethyl-4,6-dihydro-1H-pyrrolo[3,4-c]pyrazol-5-yl]-[4-(3-hydroxy-propyl)-2,5-dimethyl-piperazin-1-yl]-methanone;

$N^4$-(6,6-dimethyl-5-{[(3S,8aS)-3-methylhexahydropyrrolo[1,2-a]pyrazin-2(1H)-yl]carbonyl})-1,4,5,6-tetrahydropyrrolo[3,4-c]pyrazol-3-yl)-$N^2$-ethyl-5-fluoropyrimidine-2,4-diamine;

$N^2$-ethyl-5-fluoro-$N^4$-(5-{[(2S,5R)-4-(2-methoxyethyl)-2,5-dimethylpiperazin-1-yl]carbonyl}-6,6-dimethyl-1,4,5,6-tetrahydropyrrolo[3,4-c]pyrazol-3-yl)pyrimidine-2,4-diamine;

N4-(5-{[(2S,5R)-2,5-dimethyl-4-(3,3,3-trifluoropropyl)piperazin-1-yl]carbonyl}-6,6-dimethyl-1,4,5,6-tetrahydropyrro[3,4-c]pyrazol-3-yl)-N2-ethyl-5-fluoropyrimidine-2,4-diamine;

N-(5-fluoro-2-morpholin-4-ylpyrimidin-4-yl)-6,6-dimethyl-5-{[(2S,5R)-2,4,5-trimethylpiperazin-1-yl]carbonyl}-1,4,5,6-tetrahydropyrrolo[3,4-c]pyrazol-3-amine;

$N^2$-ethyl-5-fluoro-$N^4$-{5-[(4-fluoro-1-methylpiperidin-4-yl)carbonyl]-6,6-dimethyl-1,4,5,6-tetrahydropyrrolo[3,4-c]pyrazol-3-yl}pyrimidine-2,4-diamine;

N-(2-ethyl-5-fluoropyrimidin-4-yl)-6,6-dimethyl-5-{[(2S,5R)-2,4,5-trimethylpiperazin-1-yl]carbonyl}-1,4,5,6-tetrahydropyrrolo[3,4-c]pyrazol-3-amine;

N-(2-ethoxypyrimidin-4-yl)-6,6-dimethyl-5-{[(2S,5R)-2,4,5-trimethylpiperazin-1-yl]carbonyl})-1,4,5,6-tetrahydropyrrolo[3,4-c]pyrazol-3-amine;

5-{[(2S,5R)-2,5-dimethyl-4-(3,3,3-trifluoropropyl)piperazin-1-yl]carbonyl)}-N-(2-ethyl-5-fluoropyrimidin-4-yl)-6,6-dimethyl-1,4,5,6-tetrahydropyrrolo[3,4-c]pyrazol-3-amine;

5-[(4-fluoro-1-methylpiperidin-4-yl)carbonyl]-N-(5-fluoro-2-methylpyrimidin-4-yl)-6,6-dimethyl-1,4,5,6-tetrahydropyrrolo[3,4-c]pyrazol-3-amine;

N-(2-ethyl-5-fluoropyrimidin-4-yl)-5-[(4-fluoro-1-methylpiperidin-4-yl)carbonyl]-6,6-dimethyl-1,4,5,6-tetrahydropyrrolo[3,4-c]pyrazol-3-amine;

N-(5-fluoro-2-methylpyrimidin-4-yl)-6,6-dimethyl-5-{[(3S,8aS)-3-methylhexahydropyrrolo[1,2-a]pyrazin-2(1H)-yl]carbonyl}-1,4,5,6-tetrahydropyrrolo[3,4-c]pyrazol-3-amine;

N-(5-fluoro-2-methylpyrimidin-4-yl)-6,6-dimethyl-5-{[(2S,5R)-2,4,5-trimethylpiperazin-1-yl]carbonyl}-1,4,5,6-tetrahydropyrrolo[3,4-c]pyrazol-3-amine;

5-{[(3S)-3-ethyl-4-methylpiperazin-1-yl]carbonyl}-N-(5-fluoro-2-methylpyrimidin-4-yl)-6,6-dimethyl-1,4,5,6-tetrahydropyrrolo[3,4-c]pyrazol-3-amine;

5-{[(3R)-3-ethyl-4-methylpiperazin-1-yl]carbonyl}-N-(5-fluoro-2-methylpyrimidin-4-yl)-6,6-dimethyl-1,4,5,6-tetrahydropyrrolo[3,4-c]pyrazol-3-amine;

5-{[(2S,5R)-2,5-dimethyl-4-(tetrahydro-2H-pyran-4-yl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine;

4-[((2R,5S)-4-{[3-[(5-fluoro-2-methylpyrimidin-4-yl)amino]-6,6-dimethyl-4,6-dihydropyrrolo[3,4-c]pyrazol-5(1H)-yl]carbonyl}-2,5-dimethylpiperazin-1-yl)methyl]tetrahydro-2H-pyran-4-ol;

2-((5S)-4-{[3-[(5-fluoro-2-methylpyrimidin-4-yl)amino]-6,6-dimethyl-4,6-dihydropyrrolo[3,4-c]pyrazol-5(1H)-yl]carbonyl}-1,5-dimethylpiperazin-2-yl)ethanol;

2-((5S)-4-{[3-[(5-fluoro-2-methylpyrimidin-4-yl)amino]-6,6-dimethyl-4,6-dihydropyrrolo[3,4-c]pyrazol-5(1H)-yl]carbonyl}-1,5-dimethylpiperazin-2-yl)ethanol;

5-{[(2S,5R)-2,5-dimethyl-4-(tetrahydro-2H-pyran-4-ylmethyl)piperazin-1-yl]carbonyl}-N-(4-methoxypyrimidin-2-yl)-6,6-dimethyl-1,4,5,6-tetrahydropyrrolo[3,4-c]pyrazol-3-amine;

N-(4,6-dimethylpyrimidin-2-yl)-5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-amine;

N-[5-fluoro-2-(3-methoxypropoxy)pyrimidin-4-yl]-6,6-dimethyl-5-{[(2 S)-2,4,5,5-tetramethylpiperazin-1-yl]carbonyl}-1,4,5,6-tetrahydropyrrolo[3,4-c]pyrazol-3-amine;

N-[5-fluoro-2-(3-methoxypropoxy)pyrimidin-4-yl]-6,6-dimethyl-5-{[(2S,5R)-2,4,5-trimethylpiperazin-1-yl]carbonyl}-1,4,5,6-tetrahydropyrrolo[3,4-c]pyrazol-3-amine;

N-[5-fluoro-2-(2-methoxyethoxy)pyrimidin-4-yl]-6,6-dimethyl-5-{[(2S)-2,4,5,5-tetramethylpiperazin-1-yl]carbonyl}-1,4,5,6-tetrahydropyrrolo[3,4-c]pyrazol-3-amine;

N-[5-fluoro-2-(2-methoxyethoxy)pyrimidin-4-yl]-6,6-dimethyl-5-{[(2S,5R)-2,4,5-trimethylpiperazin-1-yl]carbonyl}-1,4,5,6-tetrahydropyrrolo[3,4-c]pyrazol-3-amine;

2(S), 5(S)-{[dimethyl-4-methylpiperazin-1-yl]carbonyl}-N-(5-fluoro-2-ethoxypyrimidin-4-yl)-6,6-dimethyl-1,4,5,6-tetrahydropyrrolo[3,4-c]pyrazol-3-amine;

[3-(2-Ethoxy-5-fluoro-pyrimidin-4yl-amino)-6,6-dimethyl-4,6-dihydro-1H-pyrrolo[3,4-c]pyrazol-5-yl]-(R)-hexahydro-pyrrolo[1,2-a]pyrazin-2-yl-methanone;

5-{[(3S,8aS)-3,8a-dimethylhexahydropyrrolo[1,2-a]pyrazin-2(1H)-yl]carbonyl)}-N-(2-ethoxy-5-fluoropyrimidin-4-yl)-6,6-dimethyl-1,4,5,6-tetrahydropyrrolo[3,4-c]pyrazol-3-amine;

5-{[(3S)-3,4-dimethylpiperazin-1-yl]carbonyl}-N-(2-ethoxy-5-fluoropyrimidin-4-yl)-6,6-dimethyl-1,4,5,6-tetrahydropyrrolo[3,4-c]pyrazol-3-amine;

5-{[(3R)-3,4-dimethylpiperazin-1-yl]carbonyl}-N-(2-ethoxy-5-fluoropyrimidin-4-yl)-6,6-dimethyl-1,4,5,6-tetrahydropyrrolo[3,4-c]pyrazol-3-amine;

5-{[(2S,5R)-2,5-dimethyl-4-(3,3,3-trifluoropropyl)piperazin-1-yl]carbonyl)}-N-(2-ethoxy-5-fluoropyrimidin-4-yl)-6,6-dimethyl-1,4,5,6-tetrahydropyrrolo[3,4-c]pyrazol-3-amine;

N-(2-ethoxy-5-fluoropyrimidin-4-yl)-5-{[(3S,8aS)-3-isopropylhexahydropyrrolo[1,2-a]pyrazin-2(1H)-yl]carbonyl}-6,6-dimethyl-1,4,5,6-tetrahydropyrrolo[3,4-c]pyrazol-3-amine;

4-[((2R,5S)-4-{[3-[(2-ethoxy-5-fluoropyrimidin-4-yl)amino]-6,6-dimethyl-4,6-dihydropyrrolo[3,4-c]pyrazol-5(1H)-yl]carbonyl}-2,5-dimethylpiperazin-1-yl)methyl]tetrahydro-2H-pyran-4-ol;

2-((5S)-4-{[3-[(5-fluoro-2-methoxypyrimidin-4-yl)amino]-6,6-dimethyl-4,6-dihydropyrrolo[3,4-c]pyrazol-5(1H)-yl]carbonyl}-1,5-dimethylpiperazin-2-yl)ethanol;

2-((5S)-4-{[3-[(5-fluoro-2-methoxypyrimidin-4-yl)amino]-6,6-dimethyl-4,6-dihydropyrrolo[3,4-c]pyrazol-5(1H)-yl]carbonyl}-1,5-dimethylpiperazin-2-yl)ethanol;

N-(2-ethoxy-5-fluoropyrimidin-4-yl)-5-[(4-fluoro-1-methylpiperidin-4-yl)carbonyl]-6,6-dimethyl-1,4,5,6-tetrahydropyrrolo[3,4-c]pyrazol-3-amine;

N-[5-fluoro-2-(2-methoxyethoxy)pyrimidin-4-yl]-5-[(4-fluoro-1-methylpiperidin-4-yl)carbonyl]-6,6-dimethyl-1,4,5,6-tetrahydropyrrolo[3,4-c]pyrazol-3-amine;

N-[5-fluoro-2-(3-methoxypropoxy)pyrimidin-4-yl]-5-[(4-fluoro-1-methylpiperidin-4-yl)carbonyl]-6,6-dimethyl-1,4,5,6-tetrahydropyrrolo[3,4-c]pyrazol-3-amine;

N-(2-ethoxy-5-fluoropyrimidin-4-yl)-6,6-dimethyl-5-{[1-(3,3,3-trifluoropropyl)piperidin-4-yl]carbonyl}-1,4,5,6-tetrahydropyrrolo[3,4-c]pyrazol-3-amine;

N-(2-ethoxy-5-fluoropyrimidin-4-yl)-6,6-dimethyl-5-{[1-(tetrahydro-2H-pyran-4-yl)piperidin-4-yl]carbonyl}-1,4,5,6-tetrahydropyrrolo[3,4-c]pyrazol-3-amine;

N-(4-ethoxypyrimidin-2-yl)-6,6-dimethyl-5-{[(2S,5R)-2,4,5-trimethylpiperazin-1-yl]carbonyl})-1,4,5,6-tetrahydropyrrolo[3,4-c]pyrazol-3-amine;

N-(4-ethoxypyrimidin-2-yl)-5-{[(2S,5R)-4-(3-methoxypropyl)-2,5-dimethylpiperazin-1-yl]carbonyl}-6,6-dimethyl-1,4,5,6-tetrahydropyrrolo[3,4-c]pyrazol-3-amine; or 2-((5S)-4-{[3-{[5-fluoro-2-(methoxymethyl)pyrimidin-4-yl]amino}-6,6-dimethyl-4,6-dihydropyrrolo[3,4-c]pyrazol-5(1H)-yl]carbonyl}-1,5-dimethylpiperazin-2-yl)ethanol.

Another embodiment provides the method of treating encephalitis, wherein the compound is N-(4-ethoxypyrimidin-2-yl)-6,6-dimethyl-5-{[(2S,5R)-2,4,5-trimethylpiperazin-1-yl]carbonyl)}-1,4,5,6-tetrahydropyrrolo[3,4-c]pyrazol-3-amine, or a pharmaceutically acceptable salt thereof. Another embodiment provides the method of treating encephalitis, wherein the compound is 5-{[(3S,8aS)-3,8a-dimethylhexahydropyrrolo[1,2-a]pyrazin-2(1H)-yl]carbonyl}-N-(2-ethoxy-5-fluoropyrimidin-4-yl)-6,6-dimethyl-1,4,5,6-tetrahydropyrrolo[3,4-c]pyrazol-3-amine, or a pharmaceutically acceptable salt thereof. Another embodiment provides the method of treating encephalitis, wherein the compound is N-(4,6-dimethylpyrimidin-2-yl)-5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-amine, or a pharmaceutically acceptable salt thereof. Another embodiment provides the method of treating encephalitis, wherein the compound is N-[5-fluoro-2-(3-methoxypropoxy)pyrimidin-4-yl]-6,6-dimethyl-5-{[(2S)-2,4,5,5-tetramethylpiperazin-1-yl]carbonyl}-1,4,5,6-tetrahydropyrrolo[3,4-c]pyrazol-3-amine, or a pharmaceutically acceptable salt thereof. Another embodiment provides the method of treating encephalitis, wherein the compound is N-(2-ethoxypyrimidin-4-yl)-6,6-dimethyl-5-{[(2S,5R)-2,4,5-trimethylpiperazin-1-yl]carbonyl}-1,4,5,6-tetrahydropyrrolo[3,4-c]pyrazol-3-amine, or a pharmaceutically acceptable salt thereof. Another embodiment provides the method of treating encephalitis, wherein the compound is N-(2-ethyl-5-fluoropyrimidin-4-yl)-6,6-dimethyl-5-{[(2S,5R)-2,4,5-trimethylpiperazin-1-yl]carbonyl})-1,4,5,6-tetrahydropyrrolo[3,4-c]pyrazol-3-amine, or a pharmaceutically acceptable salt thereof. Another embodiment provides the method of treating encephalitis, wherein the compound is $N^2$-ethyl-5-fluoro-$N^4$-(5-{[(2S,5R)-4-(2-methoxyethyl)-2,5-dimethylpiperazin-1-yl]carbonyl}-6,6-dimethyl-1,4,5,6-tetrahydropyrrolo[3,4-c]pyrazol-3-yl)pyrimidine-2,4-diamine, or a pharmaceutically acceptable salt thereof. Another embodiment provides the method of treating encephalitis, wherein the compound is 5-{[(2S,5R)-2,5-dimethyl-4-(tetrahydro-2H-pyran-4-yl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof. Another embodiment provides the method of treating encephalitis, wherein the compound is 5-{[(2S,5R)-4-ethyl-2,5-dimethylpiperazin-1-yl]carbonyl}-N-(5-fluoro-2,6-dimethylpyrimidin-4-yl)-6,6-dimethyl-1,4,5,6-tetrahydropyrrolo[3,4-c]pyrazol-3-amine, or a pharmaceutically acceptable salt thereof. Another embodiment provides the method of treating encephalitis, wherein the compound is N-(2-ethoxy-5-fluoropyrimidin-4-yl)-5-[(4-fluoro-1-methylpiperidin-4-yl)carbonyl]-6,6-dimethyl-1,4,5,6-tetrahydropyrrolo[3,4-c]pyrazol-3-amine, or a pharmaceutically acceptable salt thereof. Another embodiment provides the method of treating encephalitis, wherein the compound is 4-[((2R,5S)-4-{[3-[(2-ethoxy-5-fluoropyrimidin-4-yl)amino]-6,6-dimethyl-4,6-dihydropyrrolo[3,4-c]pyrazol-5(1H)-yl]carbonyl}-2,5-dimethylpiperazin-1-yl)methyl]tetrahydro-2H-pyran-4-ol, or a pharmaceutically acceptable salt thereof. Another embodiment provides the method of treating encephalitis, wherein the compound is N-[5-fluoro-2-(2-methoxyethoxy)pyrimidin-4-yl]-6,6-dimethyl-5-{[(2S,5R)-2,4,5-trimethylpiperazin-1-yl]carbonyl)}-1,4,5,6-tetrahydropyrrolo[3,4-c]pyrazol-3-amine, or a pharmaceutically acceptable salt thereof. Another embodiment provides the method of treating encephalitis, wherein the compound is 5-{[(2S,5R)-2,5-dimethyl-4-(tetrahydro-2H-pyran-4-ylmethyl)piperazin-1-yl]carbonyl}-N-(4-methoxypyrimidin-2-yl)-6,6-dimethyl-1,4,5,6-tetrahydropyrrolo[3,4-c]pyrazol-3-amine, or a pharmaceutically acceptable salt thereof. Another embodiment provides the method of treating encephalitis, wherein the compound is N-(5-fluoro-2-methylpyrimidin-4-yl)-6,6-dimethyl-5-{[(2S,5R)-2,4,5-trimethylpiperazin-1-yl]carbonyl)}-1,4,5,6-tetrahydropyrrolo[3,4-c]pyrazol-3-amine, or a pharmaceutically acceptable salt thereof. Another embodiment provides the method of treating encephalitis, wherein the compound is $N^2$-(cyclopropylmethyl)-$N^4$-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-5-fluoropyrimidine-2,4-diamine, or a pharmaceutically acceptable salt thereof.

One embodiment provides a method of treating encephalitis in a subject in need thereof comprising administering to the subject a composition comprising a compound, or a pharmaceutically acceptable salt thereof, selected from the group consisting of:

N-(5-{[(8 S)-6, 8-dimethyl-6,9-diazaspiro[4.5]dec-9-yl]carbonyl}-6,6-dimethyl-1,4,5,6-tetrahydropyrrolo[3,4-c]pyrazol-3-yl)pyridine-2-carboxamide;

N-(5-((3S,8aS)-3-benzyl-octahydropyrrolo[1,2-a]pyrazine-2-carbonyl)-6,6-dimethyl-1,4,5,6-tetrahydropyrrolo[3,4-c]pyrazol-3-yl)benzamide;

N-(5-((3S,8aS)-3-benzyl-octahydropyrrolo[1,2-a]pyrazine-2-carbonyl)-6,6-dimethyl-1,4,5,6-tetrahydropyrrolo[3,4-c]pyrazol-3-yl)-3-methoxybenzamide;

3,4-dichloro-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)benzamide;

N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-4,6-dimethylpicolinamide;

N-(5-((3S,8aS)-3-(cyclohexylmethyl)-octahydropyrrolo[1,2-a]pyrazine-2-carbonyl)-6,6-dimethyl-1,4,5,6-tetrahydropyrrolo[3,4-c]pyrazol-3-yl)picolinamide;

3-cyano-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)benzamide;

N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-2,3-dihydrobenzofuran-5-carboxamide;

4,5-dichloro-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)thiazole-2-carboxamide;

N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)H-pyrrolo[1,2-f]pyrimidine-3-carboxamide;

N-(5-((2R,5S)-2-(2-hydroxyethyl)-5-methyl-1-propylpiperazine-4-carbonyl)-6,6-dimethyl-1,4,5,6-tetrahydropyrrolo[3,4-c]pyrazol-3-yl)picolinamide;

N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-5-nitropicolinamide;

N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)quinoline-2-carboxamide;

N-(5-((+/-)-trans-1-allyl-2,5-dimethylpiperazine-4-carbonyl)-6,6-dimethyl-1,4,5,6-tetrahydropyrrolo[3,4-c]pyrazol-3-yl)picolinamide;

5-bromo-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)picolinamide;

N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-5-fluoropicolinamide;

N-(5-((+/-)-trans-1-ethyl-2,5-dimethylpiperazine-4-carbonyl)-6,6-dimethyl-1,4,5,6-tetrahydropyrrolo[3,4-c]pyrazol-3-yl)picolinamide;

N-(5-((+/-)-trans-1-(cyclopropylmethyl)-2,5-dimethylpiperazine-4-carbonyl)-6,6-dimethyl-1,4,5,6-tetrahydropyrrolo[3,4-c]pyrazol-3-yl)picolinamide;

N-(5-(1-(3-hydroxypropyl)-2,5-dimethylpiperazine-4-carbonyl)-6,6-dimethyl-1,4,5,6-tetrahydropyrrolo[3,4-c]pyrazol-3-yl)picolinamide;

N-(5-((3S,8aS)-3-isopropyl-octahydropyrrolo[1,2-a]pyrazine-2-carbonyl)-6,6-dimethyl-1,4,5,6-tetrahydropyrrolo[3,4-c]pyrazol-3-yl)picolinamide;

2-bromo-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)thiazole-4-carboxamide;

N-(6,6-dimethyl-5-((2R,5S)-1,2,5-trimethylpiperazine-4-carbonyl)-1,4,5,6-tetrahydropyrrolo[3,4-c]pyrazol-3-yl)picolinamide;

N-(5-((2R,5S)-1-ethyl-2,5-dimethylpiperazine-4-carbonyl)-6,6-dimethyl-1,4,5,6-tetrahydropyrrolo[3,4-c]pyrazol-3-yl)picolinamide;

N-(5-((2R,5S)-2,5-dimethyl-1-propylpiperazine-4-carbonyl)-6,6-dimethyl-1,4,5,6-tetrahydropyrrolo[3,4-c]pyrazol-3-yl)picolinamide;

N-(5-((2R,5S)-1-(cyclopropylmethyl)-2,5-dimethylpiperazine-4-carbonyl)-6,6-dimethyl-1,4,5,6-tetrahydropyrrolo[3,4-c]pyrazol-3-yl)picolinamide;

N-(5-((2R,5S)-1-butyl-2,5-dimethylpiperazine-4-carbonyl)-6,6-dimethyl-1,4,5,6-tetrahydropyrrolo[3,4-c]pyrazol-3-yl)picolinamide;

N-(6,6-dimethyl-5-{[(2S)-2,4,5,5-tetramethylpiperazin-1-yl]carbonyl}-1,4,5,6-tetrahydropyrrolo[3,4-c]pyrazol-3-yl)pyridine-2-carboxamide;

N-(5-{[(7S)-5,7-dimethyl-5,8-diazaspiro[3.5]non-8-yl]carbonyl}-6,6-dimethyl-1,4,5,6-tetrahydropyrrolo[3,4-c]pyrazol-3-yl)pyridine-2-carboxamide;

N-(5-{[(2S,5R)-4-(3-methoxypropyl)-2,5-dimethylpiperazin-1-yl]carbonyl}-6,6-dimethyl-1,4,5,6-tetrahydropyrrolo[3,4-c]pyrazol-3-yl)pyridine-2-carboxamide;

N-(5-((2R,5S)-2,5-dimethyl-1-(2(tetradhydro-2H-pyran-4-yl)ethyl)piperazine-4-carbonyl)-6,6-dimethyl-1,4,5,6-tetrahydropyrrolo[3,4-c]pyrazol-3-yl)picolinamide;

N-(5-((2R,5S)-2,5-dimethyl-1-(tetrahydro-2H-pyran-4-yl)piperazine-4-carbonyl)-6,6-dimethyl-1,4,5,6-tetrahydropyrrolo[3,4-c]pyrazol-3-yl)picolinamide;

N-(5-{[(2S,5R)-2,5-dimethyl-4-(tetrahydrofuran-3-ylmethyl)piperazin-1-yl]carbonyl})-6,6-dimethyl-1,4,5,6-tetrahydropyrrolo[3,4-c]pyrazol-3-yl)pyridine-2-carboxamide;

N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)isoquinoline-3-carboxamide;

N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-1,6-naphthyridine-2-carboxamide;

3-cyclopropyl-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-1H-pyrazole-5-carboxamide;

N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)quinoxaline-2-carboxamide;

3-tert-butyl-N-(6,6-dimethyl-5-((3S,8aS)-3-methyl-octahydropyrrolo[1,2-a]pyrazine-2-carbonyl)-1,4,5,6-tetrahydropyrrolo[3,4-c]pyrazol-3-yl)-1-methyl-1H-pyrazole-5-carboxamide;

3-cyclopropyl-N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-1H-pyrazole-5-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-5-fluoropyridine-2-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-5-methoxypyridine-2-carboxamide;

5-chloro-N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)pyridine-2-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-6-methylpyridine-2-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-3-ethyl-1-methyl-1H-pyrazole-5-carboxamide;

2-cyclopropyl-N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-1,3-oxazole-4-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-3-methylbenzamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-4-fluorobenzamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-3-fluorobenzamide;

N-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)-5-ethylpyridine-2-carboxamide;

N-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)-5-methylpyridine-2-carboxamide;

N-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)-5-methoxypyridine-2-carboxamide;

5-chloro-N-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)pyridine-2-carboxamide;

2-(3,5-dimethylisoxazol-4-yl)-N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)acetamide;

5-cyano-N-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)pyridine-2-carboxamide;

and 5-cyano-N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)pyridine-2-carboxamide.

One embodiment provides a method of treating encephalitis in a subject in need thereof comprising administering to the subject a composition comprising a compound, or a pharmaceutically acceptable salt thereof, having the formula (I):

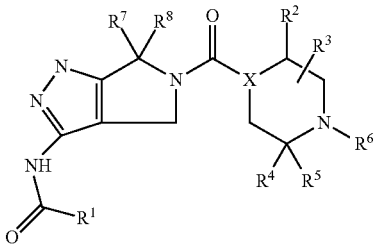

(I)

wherein:

X is C or N;

R¹ is selected from an aryl or

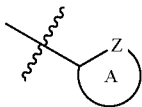

wherein ring A is a 5 to 6 membered heterocyclyl containing Z, wherein Z is an O, S or N heteroatom which is adjacent to the point of attachment, and wherein R¹ is optionally further substituted with 0 to 3 R⁹ groups and wherein two of the R⁹ groups may optionally cyclize to form an aryl or a 5-6 membered heterocyclyl ring containing N or S fused to the aryl or heterocyclyl to which it is attached;

R² is H or $C_1$-$C_6$ alkyl optionally further substituted with 0 to 3 R⁹ groups;

when X is N, R³ may be attached to any carbon on the ring and is selected from H, $C_1$-$C_6$ alkyl, halide, or perfluoroalkyl;

when X is C, R³ is a fluoro and is attached to X;

R⁴ and R⁵ are each independently selected from H, $R^a$—O—$R^b$, $C_1$-$C_8$ alkyl, $C_2$-$C_8$ alkenyl, $C_2$-$C_8$ alkynyl, —$(R^d)_m$—($C_3$-$C_{12}$ cycloalkyl), —$(R^d)_m$-aryl, —$(R^d)_m$-(3-15 membered heterocyclyl), —$(R^d)$m—($C_1$-$C_6$ perfluoroalkyl), —$(R^d)_m$-halide, —$(R^d)_m$—CN, —$(R^d)_m$—C(O)$R^a$, —$(R^d)_m$—C(O)O$R^a$, —$(R^d)_m$—C(O)N$R^aR^b$, —$(R^d)_m$—O$R^a$, —$(R^d)_m$—OC(O)$R^a$, —$(R^d)_m$—OC(O)N$R^aR^b$, —$(R^d)_m$—O—S(O)$R^a$, —$(R^d)_m$—OS(O)$_2R^a$, —$(R^d)_m$—OS(O)$_2$N$R^aR^b$, —$(R^d)_m$—OS(O)N$R^aR^b$, —$(R^d)_m$—NO$_2$, —$(R^d)_m$—N$R^aR^b$, —$(R^d)_m$—N($R^a$)C(O)$R^b$, —$(R^d)_m$—N($R^a$)C(O)O$R^b$, —$(R^d)_m$—N($R^c$)C(O)N$R^aR^b$, —$(R^d)_m$—N($R^a$)S(O)$_2$$R^b$, —$(R^d)_m$—N($R^a$)S(O)$R^b$, —$(R^d)_m$—S$R^a$, —$(R^d)_m$—S(O)$R^a$, —$(R^d)_m$—S(O)$_2R^a$, —$(R^d)_m$—S(O)N$R^aR^b$, —$(R^d)_m$—S(O)$_2$N$R^aR^b$, —$(R^d)_m$—O—$(R^e)_m$—N$R^aR^b$ or —$(R^d)_m$—N$R^a$—$(R^e)$—O$R^b$, or R⁴ and R⁵ may together cyclize to form a 3- to- 5-membered spiro-cycloalkyl; wherein any of the said $C_3$-$C_{12}$ cycloalkyl, aryl, heterocyclyl, or heteroaryl are independently optionally further substituted by 0 to 3 R₉ groups;

R⁶ is selected from $R^a$—O—$R^b$, $C_1$-$C_8$ alkyl, $C_2$-$C_8$ alkenyl, $C_2$-$C_8$ alkynyl, —$(R^d)_m$—($C_3$-$C_{12}$ cycloalkyl), —$(R^d)_m$-aryl, —$(R^d)_m$-(3-15 membered heterocyclyl), —$(R^d)_m$—($C_1$-$C_6$ perfluoroalkyl), —$(R^d)_m$-halide, —$(R^d)_m$—CN, —$(R^d)_m$—C(O)$R^a$, —$(R^d)_m$—C(O)O$R^a$, —$(R^d)_m$—C(O)N$R^aR^b$, —$(R^d)_m$—O$R^a$, —$(R^d)_m$—OC(O)$R^a$, —$(R^d)_m$—OC(O)N$R^aR^b$, —$(R^d)_m$—O—S(O)$R^a$, —$(R^d)_m$—OS(O)$_2R^a$, —$(R^d)_m$—OS(O)N$R^aR^b$, —$(R^d)_m$—OS(O)$_2$N$R^aR^b$, —$(R^d)_m$—NO($R^a$)—N$R^aR^b$, $(R^d)_m$—N($R^a$)C(O)$R^b$, —$(R^d)_m$—N($R^a$)C(O)O$R^b$, —$(R^d)_m$—N($R^c$)C(O)N$R^aR^b$, —$(R^d)_m$—N($R^a$)S(O)$_2R^b$, —$(R^d)_m$—N($R^a$)S(O)$R^b$, —$(R^d)_m$—S$R^a$, —$(R^d)_m$—S(O)$R^a$, —$(R^d)_m$—S(O)$_2R^a$, —$(R^d)_m$—S(O)N$R^aR^b$, —$(R^d)_m$—S(O)$_2$N$R^aR^b$, —$(R^d)_m$—O—$(R^e)_m$—N$R^aR^b$ or —$(R^d)_m$—N$R^a$—$(R^e)$—O$R^b$; or R⁶ may together with R⁴ cyclize to form a 4- to 7-membered heterocyclyl ring fused to the piperazine or piperadine to which they are attached; and wherein any of the said alkyl, alkenyl, alkynyl, cycloalkyl, aryl, heterocyclyl, and heteroaryl may independently be further substituted with 0 to 3 R⁹ groups;

each R⁷ and R⁸ is independently $C_1$-$C_2$ alkyl, or R⁷ and R⁸ together cyclize to form a cyclopropyl or cyclobutyl;

each R⁹ is independently selected from H, $R^a$—O—$R^b$, $C_1$-$C_8$ alkyl, $C_2$-$C_8$ alkenyl, $C_2$-$C_8$ alkynyl, —$(R^d)_m$—($C_3$-$C_{12}$ cycloalkyl), —$(R^d)_m$-aryl, —$(R^d)_m$-(3-15 membered heterocyclyl), —$(R^d)_m$—($C_1$-$C_6$ perfluoroalkyl), —$(R^d)_m$-halide, —$(R^d)_m$—CN, —$(R^d)_m$—C(O)$R^a$, —$(R^d)_m$—C(O)O$R^a$, —$(R^d)_m$—C(O)N$R^aR^b$, —$(R^d)_m$—O$R^a$, —$(R^d)_m$—OC(O)$R^a$, —$(R^d)_m$—OC(O)N$R^aR^b$, —$(R^d)_m$—O—S(O)$R^a$, —$(R^d)_m$—OS(O)$_2R^a$, —$(R^d)_m$—OS(O)$_2$N$R^aR^b$, —$(R^d)_m$—OS(O)N$R^aR^b$, —$(R^d)_m$—NO$_2$, —$(R^d)_m$—N$R^aR^b$, —$(R^d)_m$—N($R^a$)C(O)$R^b$, —$(R^d)_m$—N($R^a$)C(O)O$R^b$, —$(R^d)_m$—N($R^c$)C(O)N$R^aR^b$, —$(R^d)_m$—N($R^a$)S(O)$_2R^b$, —$(R^d)_m$—N($R^a$)S(O)$R^b$, —$(R^d)_m$—S$R^a$, —$(R^d)_m$—S(O)$R^a$, —$(R^d)_m$—S(O)$_2R^a$, —$(R^d)_m$—S(O)N$R^aR^b$, —$(R^d)_m$—S(O)$_2$N$R^aR^b$, —$(R^d)_m$—O—$(R^e)_m$—N$R^aR^b$ or —$(R^d)_m$—N$R^a$—$(R^e)$—O$R^b$; and wherein any of the said alkyl, alkenyl, alkynyl, $R^d$, $R^e$, $C_3$-$C_{12}$ cycloalkyl, aryl or 3-15 membered heterocyclyl are independently optionally further substituted by 1-3 groups selected from -halide, $C_1$-$C_6$ alkyl, $C_1$-$C_6$ perfluoroalkyl, $C_1$-$C_6$alkoxyl, $C_1$-$C_6$alkylamino, CN or oxo;

each $R^a$, $R^b$ and $R^c$ is independently selected from H, $C_1$-$C_6$perfluoroalkyl, $C_1$-$C_8$ alkyl, $C_2$-$C_8$ alkenyl, —($C_1$-$C_3$ alkylene)$_m$-($C_3$-$C_8$ cycloalkyl), —($C_1$-$C_3$ alkylene)$_m$-($C_3$-$C_8$ cycloalkenyl), $C_2$-$C_8$ alkynyl, —($C_1$-$C_3$ alkylene)$_m$-aryl, or —($C_1$-$C_3$ alkylene)$_m$-(3-8 member heterocyclyl), and each $R^a$, $R^b$ and $R^c$ is independently optionally further substituted by 0 to 3 groups selected from halide, hydroxyl, —CN, $C_1$-$C_6$ alkyl, $C_1$-$C_6$ perfluoroalkyl, $C_1$-$C_6$ alkoxyl and $C_1$-$C_6$ alkylamino; or, when connected to the same nitrogen, $R^a$ and $R^b$ may optionally form a -(3-8 membered heterocyclyl), and said 3-8 membered heterocyclyl is optionally further substituted by 0 to 3 groups selected from halide, hydroxyl, —CN, $C_1$-$C_6$ alkyl, $C_1$-$C_6$ perfluoroalkyl, $C_1$-$C_6$ alkoxyl or $C_1$-$C_6$ alkylamino;

each $R^d$ and $R^e$ is independently —($C_1$-$C_3$ alkylene)-, —($C_2$-$C_5$ alkenylene)-, or —($C_2$-$C_5$ alkynylene)-;

each m is independently 0 or 1; and with the proviso that if X=N, then R², R³, R⁴ and R⁵ are not all H.

Another embodiment provides the method of treating encephalitis, wherein R⁷ and R⁸ are both methyl. Another embodiment provides the method of treating encephalitis, wherein X is N. Another embodiment provides the method of treating encephalitis, wherein R¹ is a pyridine or a piperazine. Another embodiment provides the method of treating encephalitis, wherein R¹ is a 5-membered heterocyclyl. Another embodiment provides the method of treating encephalitis, wherein R¹ is selected from the group consisting of oxazole, isoxazole, thiazole or imidazole. Another embodiment provides the method of treating encephalitis, wherein R² or R⁴ is methyl. Another embodiment provides the method of treating encephalitis, wherein R⁶ is —$(R^d)_m$-(3-15 membered heterocyclyl). Another embodiment provides the method of treating encephalitis, wherein R⁶ is —(R^d)_m tetrahydropyran. Another embodiment provides the method of treating encephalitis, wherein R⁶ is tetrahydro-2H-pyran-4-ylmethyl. Another embodiment provides the method of treating encephalitis, wherein R² is —CH₃ in (S) configuration. Another embodiment provides the method of treating encephalitis, wherein R⁶ is —(R^d)_m—OR^a.

One embodiment provides a method of treating encephalitis in a subject in need thereof comprising administering to the subject a composition comprising a compound, or a pharmaceutically acceptable salt thereof, selected from the group consisting of:

N-(5-((2R,5S)-2,5-dimethyl-1-((tetrahydro-2H-pyran-4-yl)methyl)piperazine-4-carbonyl)-6,6-dimethyl-1,4,5,6-tetrahydropyrrolo[3,4-c]pyrazol-3-yl)picolinamide;

N-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)-5-fluoropyridine-2-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-5-ethylisoxazole-3-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-2,4-dimethyl-1,3-oxazole-5-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-2-methyl-1,3-thiazole-4-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-2-ethyl-4-methyl-1,3-oxazole-5-carboxamide;

1-cyclobutyl-N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-1H-imidazole-4-carboxamide N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-1-isopropyl-1H-imidazole-4-carboxamide;

N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-2-ethyl-1,3-oxazole-4-carboxamide;

N-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)-5-morpholin-4-ylpyridine-2-carboxamide; and N-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-5-(trifluoromethyl)pyridine-2-carboxamide.

One embodiment provides a method of treating encephalitis in a subject in need thereof comprising administering to the subject a composition comprising a compound, or a pharmaceutically acceptable salt thereof, having formula (A):

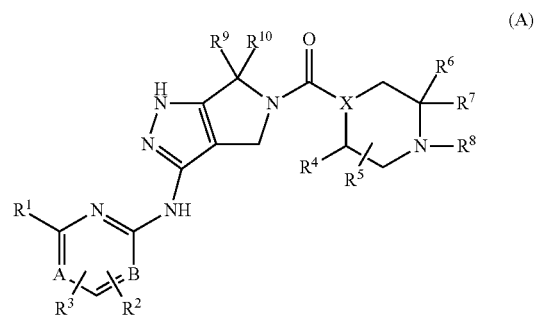

(A)

wherein
X is C—R¹¹ or N, wherein R¹¹ is H, halo, OH, $C_1$-$C_3$alkyl, $CF_3$, or CN;
A and B are independently C or N;
R¹, R² and R³ are each independently selected from H, R^a—O—R^b, $C_1$-$C_8$ alkyl, $C_2$-$C_8$ alkenyl, $C_2$-$C_8$ alkynyl, —(R^d)_m—($C_3$-$C_{12}$ cycloalkyl), —(R^d)_m-phenyl, —(R^d)_m-(3-15 membered heterocyclyl), —(R^d)_m—($C_1$-$C_6$ perfluoroalkyl), —(R^d)_m-halide, —(R^d)_m—CN, —(R^d)_m—C(O)R^a, —(R^d)_m—C(O)OR^a, —(R^d)_m—C(O)NR^aR^b, —(R^d)_m—OR^a, —(R^d)_m—OC(O)R^a, —(R^d)_m—OC(O)NR^aR^b, —(R^d)_m—O—S(O)R^a, —(R^d)_m—OS(O)_2R^a, —(R^d)_m—OS(O)_2NR^aR^b, —(R^d)_m—OS(O)NR^aR^b, —(R^d)_m—NO_2, —(R^d)_m—NR^aR^b, —(R^d)_m—N(R^a)C(O)R^b, —(R^d)_m—N(R^a)C(O)OR^b, —(R^d)_m—N(R^c)C(O)NR^aR^b, —(R^d)_m—N(R^a)S(O)_2R^b, —(R^d)_m—N(R^a)S(O)R^b, —(R^d)_m—SR^a, —(R^d)_m—S(O)R^a, —(R^d)_m—S(O)_2R^a, —(R^d)_m—S(O)NR^aR^b, —(R^d)_m—S(O)_2NR^aR^b, —(R^d)_m—O—(R^e)_m—NR^aR^b or —(R^d)_m—NR^a—(R^e)—OR^b;
wherein R² and R³ may together optionally cyclize to form a saturated or unsaturated 3-7 membered heterocyclyl fused to the 6-membered N-containing heteroaryl to which they are attached; and wherein any of the said alkyl, alkenyl, alkynyl, R^a, R^b, R^c, R^d, R^e, $C_3$-$C_{12}$ cycloalkyl, phenyl or 3-15 membered heterocyclyl, may independently be further optionally substituted by 0-3 R¹² groups;
R⁴ and R⁵ are each independently selected from H, R^a—O—R^b, $C_1$-$C_8$ alkyl, $C_2$-$C_8$ alkenyl, $C_2$-$C_8$ alkynyl, —(R^d)_m—($C_3$-$C_{12}$ cycloalkyl), —(R^d)_m-phenyl, —(R^d)_m-(3-15 membered heterocyclyl), —(R^d)_m—($C_1$-$C_6$ perfluoroalkyl), —(R^d)_m-halide, —(R^d)_m—CN, —(R^d)_m—C(O)R^a, —(R^d)_m—C(O)OR^a, —(R^d)_m—C(O)NR^aR^b, —(R^d)_m—OR^a, —(R^d)_m—OC(O)R^a, —(R^d)_m—OC(O)NR^aR^b, —(R^d)_m—O—S(O)R^a, —(R^d)_m—OS(O)_2R^a, —(R^d)_m—OS(O)_2NR^aR^b, —(R^d)_m—OS(O)NR^aR^b, —(R^d)_m—NO_2, —(R^d)_m—NR^aR^b, —(R^d)_m—N(R^a)C(O)R^b, —(R^d)_m—N(R^a)C(O)OR^b, —(R^d)_m—N(R^c)C(O)NR^aR^b, —(R^d)_m—N(R^a)S(O)_2R^b, —(R^d)_m—N(R^a)S(O)R^b, —(R^d)_m—SR^a, —(R^d)_m—S(O)R^a, —(R^d)_m—S(O)_2R^a, —(R^d)_m—S(O)NR^aR^b, —(R^d)_m—S(O)_2NR^aR^b, —(R^d)_m—O—(R^e)_m—NR^aR^b or —(R^d)_m—NR^a—(R^e)—OR^b;
wherein any of the said alkyl, alkenyl, alkynyl, R^a, R^b, R^c, R^d, R^e, $C_3$-$C_{12}$ cycloalkyl, aryl or 3-15 membered heterocyclyl are independently optionally further substituted by 0-3 R¹² groups,
R⁶ and R⁷ are each independently H, R^a—O—R^b, $C_1$-$C_8$ alkyl, $C_2$-$C_8$ alkenyl, $C_2$-$C_8$ alkynyl, —(R^d)_m—($C_3$-$C_{12}$ cycloalkyl), —(R^d)_m-phenyl, —(R^d)_m-(3-15 membered heterocyclyl), —(R^d)_m—($C_1$-$C_6$ perfluoroalkyl), —$(R^d)$m halide, —$(R^d)_m$—CN, —$(R^d)_m$—C(O)$R^a$, —$(R^d)_m$—C(O)O$R^a$, —$(R^d)_m$—C(O)N$R^aR^b$, —$(R^d)_m$—O$R^a$, —$(R^d)_m$—OC(O)$R^a$, —$(R^d)_m$—OC(O)N$R^aR^b$, —$(R^d)_m$—O—S(O)$R^a$, —$(R^d)_m$—OS(O)$_2R^a$, —$(R^d)_m$—OS(O)$_2$N$R^aR^b$, —$(R^d)_m$—OS(O)N$R^aR^b$, —$(R^d)_m$—NO$_2$, —$(R^d)_m$—N$^aR^b$, —$(R^d)_m$—N($R^a$)C(O)$R^b$, —$(R^d)_m$—N($R^a$)C(O)O$R^b$, —$(R^d)_m$—N($R^c$)C(O)N$R^aR^b$, —$(R^d)_m$—N($R^a$)S(O)$_2R^b$, —$(R^d)_m$—N($R^a$)S(O)$R^b$, —$(R^d)_m$—S$R^a$, —$(R^d)_m$—S(O)$R^a$, —$(R^d)_m$—S(O)$_2R^a$, —$(R^d)_m$—S(O)N$R^aR^b$, —$(R^d)_m$—S(O)$_2$N$R^aR^b$, —$(R^d)_m$—O—$(R^e)_m$—N$R^aR^b$ or —$(R^d)_m$—N$R^a$—$(R^e)$—O$R^b$; wherein $R^6$ and $R^7$ may together optionally cyclize to form a $C_3$-$C_7$ cycloalkyl and wherein any of the said alkyl, alkenyl, alkynyl, $R^a$, $R^b$, $R^c$, $R^d$, $R^e$, $C_3$-$C_{12}$ cycloalkyl, aryl or 3-15 membered heterocyclyl are independently optionally further substituted by 0-3 $R^{12}$ groups;

$R^8$ is H, $R^a$—O—$R^b$, $C_1$-$C_8$ alkyl, $C_2$-$C_8$ alkenyl, $C_2$-$C_8$ alkynyl, —$(R^d)_m$—($C_3$-$C_{12}$ cycloalkyl), —$(R^d)_m$-phenyl, —$(R^d)_m$-(3-15 membered heterocyclyl), —$(R^d)_m$—($C_1$-$C_6$ perfluoroalkyl), —$(R^d)_m$-halide, —$(R^d)_m$—CN, —$(R^d)_m$—C(O)$R^a$, —$(R^d)_m$—C(O)O$R^a$, —$(R^d)_m$—C(O)N$R^aR^b$, —$(R^d)_m$—O$R^a$, —$(R^d)_m$—OC(O)$R^a$, —$(R^d)_m$—OC(O)N$R^aR^b$, —$(R^d)_m$—O—S(O)$R^a$, —$(R^d)_m$—OS(O)$_2R^a$, —$(R^d)_m$—OS(O)$_2$N$R^aR^b$, —$(R^d)_m$—OS(O)N$R^aR^b$, —$(R^d)_m$—NO$_2$, —$(R^d)_m$—N$^aR^b$, —$(R^d)_m$—N($R^a$)C(O)$R^b$, —$(R^d)_m$—N($R^a$)C(O)O$R^b$, —$(R^d)_m$—N($R^c$)C(O)N$R^aR^b$, —$(R^d)_m$—N($R^a$)S(O)$_2R^b$, —$((R^d)_m$—N($R^a$)S(O)$R^b$, —$(R^d)_m$—S$R^a$, —$(R^d)_m$—S(O)$R^a$, —$(R^d)_m$—S(O)$_2R^a$, —$(R^d)_m$—S(O)N$R^aR^b$, —$(R^d)_m$—S(O)$_2$N$R^aR^b$, —$(R^d)_m$—O—$(R^e)_m$—N$R^aR^b$ or —$(R^d)_m$—N$R^a$—$(R^e)$—O$R^b$; and wherein any of the said alkyl, alkenyl, alkynyl, $R^a$, $R^b$, $R^c$, $R^d$, $R^e$, $C_3$-$C_{12}$ cycloalkyl, phenyl, or 3-15 membered heterocyclyl are independently optionally further substituted by 1-3 groups selected from —F, $C_1$-$C_3$ alkyl, $C_1$-$C_3$ perfluoroalkyl, hydroxyl, $C_1$-$C_6$alkoxyl, or oxo;

$R^9$ and $R^{10}$ are each independently $C_1$-$C_2$ alkyl or can together cyclize to form a cyclopropyl or cyclobutyl;

each $R^{12}$ is independently H, $R^a$—O—$R^b$, $C_1$-$C_8$ alkyl, $C_2$-$C_8$ alkenyl, $C_2$-$C_8$ alkynyl, —$(R^d)_m$—($C_3$-$C_{12}$ cycloalkyl), —$(R^d)_m$-phenyl, —$(R^d)_m$-(3-15 membered heterocyclyl), —$(R^d)_m$—($C_1$-$C_6$ perfluoroalkyl), —$(R^d)_m$-halide, —$(R^d)_m$—CN, —$(R^d)_m$—C(O)$R^a$, —$(R^d)_m$—C(O)O$R^a$, —$(R^d)_m$—C(O)N$R^aR^b$, —$(R^d)_m$—O$R^a$, —$(R^d)_m$—OC(O)$R^a$, —$(R^d)_m$—OC(O)N$R^aR^b$, —$(R^d)_m$—O—S(O)$R^a$, —$(R^d)_m$—OS(O)$_2R^a$, —$(R^d)_m$—OS(O)$_2$N$R^aR^b$, —$(R^d)_m$—OS(O)N$R^aR^b$, —$(R^d)_m$—NO$_2$, —$(R^d)_m$—N$^aR^b$, —$(R^d)_m$—N($R^a$)C(O)$R^b$, —$(R^d)_m$—N($R^a$)C(O)O$R^b$, —$(R^d)_m$—N($R^c$)C(O)N$R^aR^b$, —$(R^d)_m$—N($R^a$)S(O)$_2R^b$, —$(R^d)_m$—N($R^a$)S(O)$R^b$, —$(R^d)_m$—S$R^a$, —$(R^d)_m$—S(O)$R^a$, —$(R^d)_m$—S(O)$_2R^a$, —$(R^d)_m$—S(O)N$R^aR^b$, —$(R^d)_m$—S(O)$_2$N$R^aR^b$, —$(R^d)_m$—O—$(R^e)_m$—N$R^aR^b$ or —$(R^d)_m$—N$R^a$—$(R^e)$—O$R^b$; and wherein any of the said alkyl, alkenyl, alkynyl, $R^a$, $R^b$, $R^c$, $R^d$, $R^e$, $C_3$-$C_{12}$ cycloalkyl, phenyl, or 3-15 membered heterocyclyl, are independently optionally further substituted by 1-3 groups selected from —F, $C_1$-$C_3$ alkyl, $C_1$-$C_3$ perfluoroalkyl, hydroxyl, $C_1$-$C_6$alkoxyl or oxo;

each $R^a$, $R^b$ and $R^c$ is independently selected from H, $C_1$-$C_8$ alkyl, $C_2$-$C_8$ alkenyl, —$(R^d)_m$—($C_3$-$C_8$ cycloalkyl), —$(R^d)_m$—($C_3$-$C_8$ cycloalkenyl), $C_2$-$C_8$ alkynyl, —$(R^d)_m$-phenyl, or —$(R^d)_m$-(3-7 membered heterocyclyl), and each $R^a$, $R^b$ and $R^c$ is independently optionally further substituted by 1-3 groups selected from halide, hydroxyl, —CN, $C_1$-$C_6$ alkyl, $C_1$-$C_6$ perfluoroalkyl, $C_1$-$C_6$ alkoxyl and $C_1$-$C_6$ alkylamino; or, when connected to the same nitrogen, $R^a$ and $R^b$ may together optionally form a 3-7 membered heterocyclyl, which may optionally be further substituted by 0-3 groups selected from halide, hydroxyl, —CN, $C_1$-$C_6$ alkyl, $C_1$-$C_6$ perfluoroalkyl, $C_1$-$C_6$ alkoxyl or $C_1$-$C_6$ alkylamino;

each $R^d$ and $R^e$ is independently-($C_1$-$C_3$ alkylene)-, —($C_2$-$C_5$ alkenylene)-, or —($C_2$-$C_5$ alkynylene)-;

and each m is independently 0 or 1;

with the proviso that when X is N, $R^6$ and $R^7$ are not both H, and that when X is C—$R^{11}$, $R^6$ and $R^7$ are both H;

or a pharmaceutically acceptable salt thereof.

Another embodiment provides a method of treating encephalitis, wherein for the compound of Formula (A), $R^9$ and $R^{10}$ are both methyl. Another embodiment provides a method of treating encephalitis, wherein for the compound of Formula (A), X is N and $R^6$ and $R^7$ are each independently H or $C_1$-$C_6$alkyl but are not both H. Another embodiment provides a method of treating encephalitis, wherein for the compound of Formula (A), A is N and B is C. Another embodiment provides a method of treating encephalitis, wherein for the compound of Formula (A), A is C and B is N. Another embodiment provides a method of treating encephalitis, wherein for the compound of Formula (A), $R^6$ and $R^7$ are both methyl. Another embodiment provides a method of treating encephalitis, wherein for the compound of Formula (A), $R^6$ is H and $R^7$ is methyl. Another embodiment provides a method of treating encephalitis, wherein for the compound of Formula (A), $R^4$ is $R^a$—O—$R^b$, $C_1$-$C_8$ alkyl, $C_2$-$C_8$ alkenyl, $C_2$-$C_8$ alkynyl, —$(R^d)_m$—($C_3$-$C_{12}$cycloalkyl), —$(R^d)_m$-phenyl, —$(R^d)_m$-(3-15 membered heterocyclyl), —$(R^d)_m$—($C_1$-$C_6$perfluoroalkyl), —$(R^d)_m$-halide, —$(R^d)_m$—CN, —$(R^d)_m$—C(O)$R^a$, —$(R^d)_m$—C(O)O$R^a$, —$(R^d)_m$—C(O)N$R^aR^b$, —$(R^d)_m$—O$R^a$, —$(R^d)_m$—OC(O)$R^a$, —$(R^d)_m$—OC(O)N$R^aR^b$, —$(R^d)_m$—O—S(O)$R^a$, —$(R^d)_m$—OS(O)$_2R^a$, —$(R^d)_m$—O S(O)$_2$N$R^aR^b$, —$(R^d)_m$—OS(O)N$R^aR^b$, —$(R^d)_m$—NO$_2$, —$(R^d)$m N$R^aR^b$, —$(R^d)_m$—N($R^a$)C(O)$R^b$, —$(R^d)_m$—N($R^a$)C(O)O$R^b$, —$(R^d)_m$—N($R^c$)C(O)N$R^aR^b$, —$(R^d)_m$—N($R^a$)S(O)$_2R^b$, —$(R^d)_m$—N($R^a$)S(O)$R^b$, —$(R^d)_m$—S$R^a$, —$(R^d)_m$—S(O)$R^a$, —$(R^d)_m$—S(O)$_2R^a$, —$(R^d)_m$—S(O)N$R^aR^b$, —$(R^d)_m$—S(O)$_2$N$R^aR^b$, —$(R^d)_m$—O—$(R^e)_m$—N$R^aR^b$ or —$(R^d)_m$—N$R^a$—$(R^e)$—O$R^b$; wherein the said $R^a$, $R^b$, $R^c$, $R^d$, $R^e$, $C_3$-$C_{12}$ cycloalkyl, aryl, 3-15 membered heterocyclyl, are independently optionally further substituted by 0-3 $R^{12}$ groups. Another embodiment provides a method of treating encephalitis, wherein for the compound of Formula (A), $R^4$ is methyl. Another embodiment provides a method of treating encephalitis, wherein for the compound of Formula (A), $R^1$ is $R^a$—O—$R^b$, $C_1$-$C_8$ alkyl, $C_2$-$C_8$ alkenyl, $C_2$-$C_8$ alkynyl, —$(R^d)_m$—($C_3$-$C_{12}$ cycloalkyl), —$(R^d)_m$-phenyl, —$(R^d)_m$-(3-15 membered heterocyclyl), —$(R^d)_m$—($C_1$-$C_6$ perfluoroalkyl), —$(R^d)_m$-halide, —$(R^d)_m$—CN, —$(R^d)_m$—C(O)$R^a$, —$(R^d)_m$—C(O)O$R^a$, —$(R^d)_m$—C(O)N$R^aR^b$, —$(R^d)_m$—O$R^a$, —$(R^d)_m$—OC(O)$R^a$, —$(R^d)_m$—OC(O)N$R^aR^b$, —$(R^d)_m$—O—S(O)$R^a$, —$(R^d)_m$—OS(O)$_2R^a$, —$(R^d)_m$—OS(O)$_2$N$R^aR^b$, —$(R^d)_m$—OS(O)N$R^aR^b$, —$(R^d)_m$—NO$_2$, —$(R^d)_m$—N$R^aR^b$, —$(R^d)_m$—N($R^a$)C(O)$R^b$, —$(R^d)_m$—N($R^a$)C(O)O$R^b$, —$(R^d)_m$—N($R^c$)C(O)N$R^aR^b$, —$(R^d)_m$—N($R^a$)S(O)$_2R^b$, —$(R^d)_m$—N($R^a$)S(O)$R^b$, —$(R^d)_m$—S$R^a$, —$(R^d)_m$—S(O)$R^a$, —$(R^d)_m$—S(O)$_2R^a$, —$(R^d)_m$—S(O)N$R^aR^b$, —$(R^d)_m$—S(O)$_2$N$R^aR^b$, —$(R^d)_m$—O—$(R^e)_m$—N$R^aR^b$ or —$(R^d)_m$—N$R^a$—$(R^e)$—O$R^b$; wherein the said —$R^a$, $R^b$, $R^c$, $R^d$, $R^e$, $C_3$-$C_{12}$ cycloalkyl, aryl, the said 3-15 membered heterocyclyl, are independently optionally further substituted by 0-3 $R^{12}$ groups. Another embodiment provides a method of treating encephalitis, wherein for the compound of Formula (A), $R^1$ is $-(R^d)_m-OR^a$, $C_1$-$C_8$ alkyl, or $-(R^d)_m-NR^aR^b$. Another embodiment provides a method of treating encephalitis, wherein for the compound of Formula (A), $R^8$ is $R^a-O-R^b$, $C_1$-$C_8$ alkyl, $C_2$-$C_8$ alkenyl, $C_2$-$C_8$ alkynyl, $-(R^d)_m-(C_3$-$C_{12}$ cycloalkyl), $-(R^d)_m$-phenyl, $-(R^d)_m$-(3-15 membered heterocyclyl), $-(R^d)_m-(C_1$-$C_6$ perfluoroalkyl), $-(R^d)_m$-halide, $-(R^d)_m-CN$, $-(R^d)_m-OR^a$, or $-(R^d)_m-NR^aR^b$. Another embodiment provides a method of treating encephalitis, wherein for the compound of Formula (A), each $R^d$ and $R^e$ is independently an $-(C_1$-$C_3$ alkylene).

One embodiment provides a method of treating encephalitis in a subject in need thereof comprising administering to the subject a composition comprising a compound, or a pharmaceutically acceptable salt thereof, having formula (B):

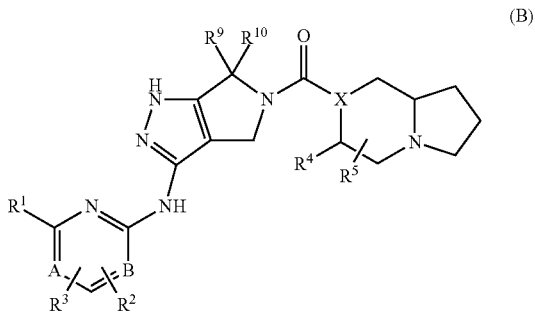

(B)

wherein
X is $C-R^{11}$ or N, wherein $R^{11}$ is H, halo, OH, $C_1$-$C_3$alkyl, $CF_3$, or CN;
A and B are independently C or N;
$R^1$ is $R^a-O-R^b$, $C_1$-$C_8$ alkyl, $C_2$-$C_8$ alkenyl, $C_2$-$C_8$ alkynyl, $-(R^d)_m-(C_3$-$C_{12}$ cycloalkyl), $-(R^d)_m$-phenyl, $-(R^d)_m$-(3-15 membered heterocyclyl), $-(R^d)_m-(C_1$-$C_6$ perfluoroalkyl), $-(R^d)_m$-halide, $-(R^d)_m-CN$, $-(R^d)_m-C(O)R^a$, $-(R^d)_m-C(O)OR^a$, $-(R^d)_m-C(O)NR^aR^b$, $-(R^d)_m-OR^a$, $-(R^d)_m-OC(O)R^a$, $-(R^d)_m-OC(O)NR^aR^b$, $-(R^d)_m-O-S(O)R^a$, $-(R^d)_m-OS(O)_2R^a$, $-(R^d)_m-OS(O)_2NR^aR^b$, $-(R^d)_m-OS(O)NR^aR^b$, $-(R^d)_m-NO_2$, $-(R^d)_m-N^aR^b$, $-(R^d)_m-N(R^a)C(O)R^b$, $-(R^d)_m-N(R^a)C(O)OR^b$, $-(R^d)_m-N(R^c)C(O)NR^aR^b$, $-(R^d)_m-N(R^a)S(O)_2R^b$, $-(R^d)_m-N(R^a)S(O)R^b$, $-(R^d)_m-SR^a$, $-(R^d)_m-S(O)R^a$, $-(R^d)_m-S(O)_2R^a$, $-(R^d)_m-S(O)NR^aR^b$, $-(R^d)_m-S(O)_2NR^aR^b$, $-(R^d)_m-O-(R^e)_m-NR^aR^b$ or $-(R^d)_m-NR^a-(R^e)-OR^b$; and wherein any of the said alkyl, alkenyl, alkynyl, $R^a$, $R^b$, $R^c$, $R^d$, $R^e$, $C_3$-$C_{12}$ cycloalkyl, phenyl or 3-15 membered heterocyclyl, may independently be further optionally substituted by 0-3 $R^{12}$ groups;
$R^2$ and $R^3$ are each independently selected from H, $R^a-O-R^b$, $C_1$-$C_8$ alkyl, $C_2$-$C_8$ alkenyl, $C_2$-$C_8$ alkynyl, $-(R^d)_m-(C_3$-$C_{12}$ cycloalkyl), $-(R^d)_m$-phenyl, $-(R^d)_m$-(3-15 membered heterocyclyl), $-(R^d)_m-(C_1$-$C_6$ perfluoroalkyl), $-(R^d)_m$-halide, $-(R^d)_m-CN$, $-(R^d)_m-C(O)R^a$, $-(R^d)_m-C(O)OR^a$, $-(R^d)_m-C(O)NR^aR^b$, $-(R^d)_m-OR^a$, $-(R^d)_m-OC(O)R^a$, $-(R^d)_m-OC(O)NR^aR^b$, $-(R^d)_m-O-S(O)R^a$, $-(R^d)_m-OS(O)_2R^a$, $-(R^d)_m-OS(O)_2NR^aR^b$, $-(R^d)_m-OS(O)NR^aR^b$, $-(R^d)_m-NO_2$, $-(R^d)_m-NR^aR^b$, $-(R^d)_m-N(R^a)C(O)R^b$, $-(R^d)_m-N(R^a)C(O)OR^b$, $-(R^d)_m-N(R^c)C(O)NR^aR^b$, $-(R^d)_m-N(R^a)S(O)_2R^b$, $-(R^d)_m-N(R^a)S(O)R^b$, $-(R^d)_m-SR^a$, $-(R^d)_m-S(O)R^a$, $-(R^d)_m-S(O)_2R^a$, $-(R^d)_m-S(O)NR^aR^b$, $-(R^d)_m-S(O)_2NR^aR^b$, $-(R^d)_m-O-(R^e)_m-NR^aR^b$ or $-(R^d)_m-NR^a-(R^e)-OR^b$; wherein $R^2$ and $R^3$ may together optionally cyclize to form a saturated or unsaturated 3-7 membered heterocyclyl fused to the 6-membered N-containing heteroaryl to which they are attached; and wherein any of the said alkyl, alkenyl, alkynyl, $R^a$, $R^b$, $R^c$, $R^d$, $R^e$, $C_3$-$C_{12}$ cycloalkyl, phenyl or 3-15 membered heterocyclyl, may independently be further optionally substituted by 0-3 $R^{12}$ groups;
$R^4$ and $R^5$ are each independently selected from H, $R^a-O-R^b$, $C_1$-$C_8$ alkyl, $C_2$-$C_8$ alkenyl, $C_2$-$C_8$ alkynyl, $-(R^d)_m-(C_3$-$C_{12}$ cycloalkyl), $-(R^d)_m$-phenyl, $-(R^d)_m$-(3-15 membered heterocyclyl), $-(R^d)_m-(C_1$-$C_6$ perfluoroalkyl), $-(R^d)_m$-halide, $-(R^d)_m-CN$, $-(R^d)_m-C(O)R^a$, $-(R^d)_m-C(O)OR^a$, $-(R^d)_m-C(O)NR^aR^b$, $-(R^d)_m-OR^a$, $-(R^d)_m-OC(O)R^a$, $-(R^d)_m-OC(O)NR^aR^b$, $-(R^d)_m-O-S(O)R^a$, $-(R^d)_m-OS(O)_2R^a$, $-(R^d)_m-OS(O)_2NR^aR^b$, $-(R^d)_m-OS(O)NR^aR^b$, $-(R^d)_m-NO_2$, $-(R^d)_m-NR^aR^b$, $-(R^d)_m-N(R^a)C(O)R^b$, $-(R^d)_m-N(R^a)C(O)OR^b$, $-(R^d)_m-N(R^c)C(O)NR^aR^b$, $-(R^d)_m-N(R^a)S(O)_2R^b$, $-(R^d)_m-N(R^a)S(O)R^b$, $-(R^d)_m-SR^a$, $-(R^d)_m-S(O)R^a$, $-(R^d)_m-S(O)_2R^a$, $-(R^d)_m-S(O)NR^aR^b$, $-(R^d)_m-S(O)_2NR^aR^b$, $-(R^d)_m-O-(R^e)_m-NR^aR^b$ or $-(R^d)_m-NR^a-(R^e)-OR^b$; wherein any of the said alkyl, alkenyl, alkynyl, $R^a$, $R^b$, $R^c$, $R^d$, $R^e$, $C_3$-$C_{12}$ cycloalkyl, aryl or 3-15 membered heterocyclyl are independently optionally further substituted by 0-3 $R^{12}$ groups,
$R^8$ is H, $R^a-O-R^b$, $C_1$-$C_8$ alkyl, $C_2$-$C_8$ alkenyl, $C_2$-$C_8$ alkynyl, $-(R^d)_m-(C_3$-$C_{12}$ cycloalkyl), $-(R^d)_m$-phenyl, $-(R^d)_m$-(3-15 membered heterocyclyl), $-(R^d)_m-(C_1$-$C_6$ perfluoroalkyl), $-(R^d)_m$-halide, $-(R^d)_m-CN$, $-(R^d)_m-C(O)R^a$, $-(R^d)_m-C(O)OR^a$, $-(R^d)_m-C(O)NR^aR^b$, $-(R^d)_m-OR^a$, $-(R^d)_m-OC(O)R^a$, $-(R^d)_m-OC(O)NR^aR^b$, $-(R^d)_m-O-S(O)R^a$, $-(R^d)_m-OS(O)_2R^a$, $-(R^d)_m-OS(O)_2NR^aR^b$, $-(R^d)_m-OS(O)NR^aR^b$, $-(R^d)_m-NO_2$, $-(R^d)_m-N^aR^b$, $-(R^d)_m-N(R^a)C(O)R^b$, $-(R^d)_m-N(R^a)C(O)OR^b$, $-(R^d)_m-N(R^c)C(O)NR^aR^b$, $-(R^d)_m-N(R^a)S(O)_2R^b$, $-((R^d)_m-N(R^a)S(O)R^b$, $-(R^d)_m-SR^a$, $-(R^d)_m-S(O)R^a$, $-(R^d)_m-S(O)_2R^a$, $-(R^d)_m-S(O)NR^aR^b$, $-(R^d)_m-S(O)_2NR^aR^b$, $-(R^d)_m-O-(R^e)_m-NR^aR^b$ or $-(R^d)_m-NR^a-(R^e)-OR^b$; and wherein any of the said alkyl, alkenyl, alkynyl, $R^a$, $R^b$, $R^c$, $R^d$, $R^e$, $C_3$-$C_{12}$ cycloalkyl, phenyl, or 3-15 membered heterocyclyl are independently optionally further substituted by 1-3 groups selected from $-F$, $C_1$-$C_3$ alkyl, $C_1$-$C_3$ perfluoroalkyl, hydroxyl, $C_1$-$C_6$alkoxyl, or oxo;
$R^9$ and $R^{10}$ are each independently $C_1$-$C_2$ alkyl or can together cyclize to form a cyclopropyl or cyclobutyl;
each $R^{12}$ is independently H, $R^a-O-R^b$, $C_1$-$C_8$ alkyl, $C_2$-$C_8$ alkenyl, $C_2$-$C_8$ alkynyl, $-(R^d)_m-(C_3$-$C_{12}$ cycloalkyl), $-(R^d)_m$-phenyl, $-(R^d)_m$-(3-15 membered heterocyclyl), $-(R^d)_m-(C_1$-$C_6$ perfluoroalkyl), $-(R^d)_m$-halide, $-(R^d)_m-CN$, $-(R^d)_m-C(O)R^a$, $-(R^d)_m-C(O)OR^a$, $-(R^d)_m-C(O)NR^aR^b$, $-(R^d)_m-OR^a$, $-(R^d)_m-OC(O)R^a$, $-(R^d)_m-OC(O)NR^aR^b$, $-(R^d)_m-O-S(O)R^a$, $-(R^d)_m-OS(O)_2R^a$, $-(R^d)_m-OS(O)_2NR^aR^b$, $-(R^d)_m-OS(O)NR^aR^b$, $-(R^d)_m-NO_2$, $-(R^d)_m-N^aR^b$, $-(R^d)_m-N(R^a)C(O)R^b$, —(R$^d$)$_m$—N(R$^a$)C(O)OR$^b$, —(R$^d$)$_m$—N(R$^c$)C(O)NR$^a$R$^b$, —(R$^d$)$_m$—N(R$^a$)S(O)$_2$R$^b$, —(R$^d$)$_m$—N(R$^a$)S(O)R$^b$, —(R$^d$)$_m$—SR$^a$, —(R$^d$)$_m$— S(O)R$^a$, —(R$^d$)$_m$—S(O)$_2$R$^a$, —(R$^d$)$_m$—S(O)NR$^a$R$^b$, —(R$^d$)$_m$—S(O)$_2$NR$^a$R$^b$, —(R$^d$)$_m$—O—(R$^e$)$_m$—NR$^a$R$^b$ or —(R$^d$)$_m$—NR$^a$—(R$^e$)—OR$^b$; and wherein any of the said alkyl, alkenyl, alkynyl, R$^a$, R$^b$, R$^c$, R$^d$, R$^e$, C$_3$-C$_{12}$ cycloalkyl, phenyl, or 3-15 membered heterocyclyl, are independently optionally further substituted by 1-3 groups selected from —F, C$_1$-C$_3$ alkyl, C$_1$-C$_3$ perfluoroalkyl, hydroxyl, C$_1$-C$_6$alkoxyl or oxo;

each R$^a$, R$^b$ and R$^c$ is independently selected from H, C$_1$-C$_8$ alkyl, C$_2$-C$_8$ alkenyl, —(R$^d$)$_m$—(C$_3$-C$_8$ cycloalkyl), —(R$^d$)$_m$—(C$_3$-C$_8$ cycloalkenyl), C$_2$-C$_8$ alkynyl, —(R$^d$)$_m$-phenyl, or —(R$^d$)$_m$-(3-7 membered heterocyclyl), and each R$^a$, R$^b$ and R$^c$ is independently optionally further substituted by 1-3 groups selected from halide, hydroxyl, —CN, C$_1$-C$_6$ alkyl, C$_1$-C$_6$ perfluoroalkyl, C$_1$-C$_6$ alkoxyl and C$_1$-C$_6$ alkylamino; or, when connected to the same nitrogen, R$^a$ and R$^b$ may together optionally form a 3-7 membered heterocyclyl, which may optionally be further substituted by 0-3 groups selected from halide, hydroxyl, —CN, C$_1$-C$_6$ alkyl, C$_1$-C$_6$ perfluoroalkyl, C$_1$-C$_6$ alkoxyl or C$_1$-C$_6$ alkylamino;

each R$^d$ and R$^e$ is independently-(C$_1$-C$_3$ alkylene)-, —(C$_2$-C$_5$ alkenylene)-, or —(C$_2$-C$_5$ alkynylene)-; and each m is independently 0 or 1, or a pharmaceutically acceptable salt thereof.

Another embodiment provides a method of treating encephalitis, wherein for the compound of Formula (B), A is N and B is C. Another embodiment provides a method of treating encephalitis, wherein for the compound of Formula (B), R$^9$ and R$^{10}$ are both methyl. Another embodiment provides a method of treating encephalitis, wherein for the compound of Formula (B), R$^4$ is —(R$^d$)$_m$—OR$^a$, C$_1$-C$_8$ alkyl, C$_2$-C$_8$ alkenyl or C$_2$-C$_8$ alkynyl. Another embodiment provides a method of treating encephalitis, wherein for the compound of Formula (B), R$^4$ is methyl. Another embodiment provides a method of treating encephalitis, wherein for the compound of Formula (B), R$^1$ is —(R$^d$)$_m$—OR$^a$, C$_1$-C$_8$ alkyl, or —(R$^d$)$_m$—NR$^a$R$^b$. Another embodiment provides a method of treating encephalitis, wherein for the compound of Formula (B), each R$^d$ and R$^e$ is independently an —(C$_1$-C$_3$ alkylene)-.

The pyrrolo-pyrazole compounds used in the methods described herein are, in some instances, administered orally as tablets or capsules, as oily or aqueous suspensions, lozenges, troches, powders, granules, emulsions, syrups or elixirs. The compositions for oral use may include one or more agents for flavoring, sweetening, coloring and preserving in order to produce pharmaceutically elegant and palatable preparations. Tablets may contain pharmaceutically acceptable excipients as an aid in the manufacture of such tablets. As is conventional in the art these tablets may be coated with a pharmaceutically acceptable enteric coating, such as glyceryl monostearate or glyceryl distearate, to delay disintegration and absorption in the gastrointestinal tract to provide a sustained action over a longer period.

Formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, such as peanut oil, liquid paraffin or olive oil.

Aqueous suspensions normally contain active ingredients in admixture with excipients suitable for the manufacture of an aqueous suspension. Such excipients may be a suspending agent, such as sodium carboxymethyl cellulose, methyl cellulose, hydroxypropylmethyl cellulose, sodium alginate, polyvinylpyrrolidone, gum tragacanth and gum acacia; a dispersing or wetting agent that may be a naturally occurring phosphatide such as lecithin, a condensation product of ethylene oxide and a long chain fatty acid, for example polyoxyethylene stearate, a condensation product of ethylene oxide and a long chain aliphatic alcohol such as heptadecaethylenoxycetanol, a condensation product of ethylene oxide and a partial ester derived from a fatty acid and hexitol such as polyoxyethylene sorbitol monooleate or a fatty acid hexitol anhydrides such as polyoxyethylene sorbitan monooleate.

The pyrrolo-pyrazole compounds used in the methods described herein are, in some instances, in the form of a sterile injectable aqueous or oleagenous suspension. This suspension may be formulated according to know methods using those suitable dispersing or wetting agents and suspending agents that have been mentioned above. The sterile injectable preparation may also be formulated as a suspension in a non toxic perenterally-acceptable diluent or solvent, for example as a solution in 1,3-butanediol. Among the acceptable vehicles and solvents that may be employed are water, Ringers solution and isotonic sodium chloride solution. For this purpose any bland fixed oil may be employed including synthetic mono- or diglycerides. In addition fatty acids such as oleic acid find use in the preparation of injectables.

Dosage levels of the pyrrolo-pyrazole compounds to be used for the methods of treatment disclosed herein range from about 0.5 mg/kg body weight to about 100 mg/kg body weight. A preferred dosage range is between about 30 mg/kg body weight to about 100 mg/kg body weight.

EXAMPLES

These examples are provided for illustrative purposes only and not to limit the scope of the claims provided herein.

Compound A refers to 5-{[(2S,5R)-2,5-Dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, which was disclosed in WO 2008/096260 and having the chemical structure:

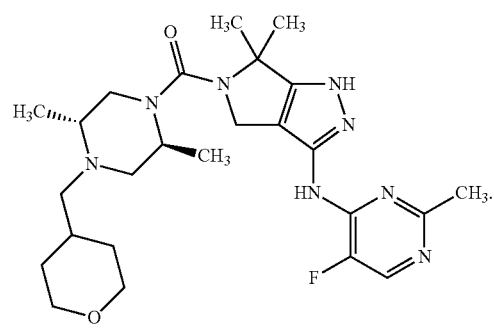 [SMILES: Cc1ncc(F)c(Nc2n[nH]c3c2CN(C(=O)N2C[C@@H](C)N(CC4CCOCC4)C[C@@H]2C)C3(C)C)n1]

A summary of PKC inhibition by compound A is provided in Table 1. The methods for these determinations have been described (Grant, et al. 2010, Eur J Pharmacol. 627:16-25). Compound A is a potent, ATP-competitive and reversible inhibitor of conventional PKC enzymes with a Ki=5.3 nM for recombinant PKC beta and a Ki=10.4 nM for recombinant PKC alpha. It also is a potent inhibitor of the novel isoform PKC theta with an $IC_{50}$=25.6 nM. Furthermore, it demonstrated some potency for conventional isoform PKC gamma with an $IC_{50}$=57.5 nM. Otherwise, it demonstrated a high degree of selectivity for the other members of the conventional, novel and atypical isoforms of PKC as shown by lower potency against these isoforms (Table 1). Compound A does not significantly inhibit PKC delta.

TABLE 1

| In Vitro Assays | $IC_{50}$ (nM) | Ki (nM) |
|---|---|---|
| Human PKC alpha | | 10.4 |
| Human PKC betaII | | 5.3 |
| Human PKC alpha | 2.3 | |
| Human PKC betaI | 8.1 | |
| Human PKC betaII | 7.6 | |
| Human PKC theta | 25.6 | |
| Human PKC gamma | 57.5 | |
| Human PKC mu | 314 | |
| Human PKC epsilon | 808 | |
| Human PKC delta | >1000 | |
| Human PKC eta | >1000 | |
| Human PKC iota | >1000 | |
| Human PKC zeta | >1000 | |
| Human PRKCN (PKD3) | 131 | |
| pSHP2 (PKCβ cell assay) | 9.8 | |
| Interleukin-8 release | 39 | |

Example 1: Testing in MRL/Lpr Mouse Model of Lupus

Compound A was tested for efficacy in the MRL/lpr mouse model of lupus (Shlomchik M J, et al, 1994, J Exp Med 180:1295-1306; Cohen P L and Eisenberg R. A. 1991, Annu Rev Immunol, 9:243-69; Honigberg, L. A., et al., 2010, Proc Natl Acad Sci USA. 107:13075-80). Female MRL/MpJ-Tnfrsf6llpr/J mice of 8-9 weeks of age were used in the study. When the mice reached 12 weeks of age, they were randomized by animal body weight into one of the treatment groups or an untreated control group. Treatments was initiated after randomization and continued for 12 weeks. Starting on study week 1, and then every week thereafter, urine from each animal was tested for proteinuria using the Clinitech Multistick test strip (Bayer). The animals were observed daily for significant clinical signs, moribundity and mortality. Scoring of lymphadenopathy (cervical, brachial, and inguinal) for all animals was recorded every week once lesions become apparent in 50% of the animals in vehicle-treated group.

Compound A was prepared as an oral suspension. Initial dosing was completed at two dose levels, 60 and 90 mg/kg, BID for a total dose of 120 and 180 mg/kg/day. Separate, independent pharmacokinetics experiments were done and showed an unexpectedly low and insufficient exposure of compound A in mice at the 60 mg/kg dose. Therefore the lower dose was doubled after the initial 4 weeks of dosing. Dosing for the final 8 weeks was at 180 and 240 mg/kg/day.

Figure 2:
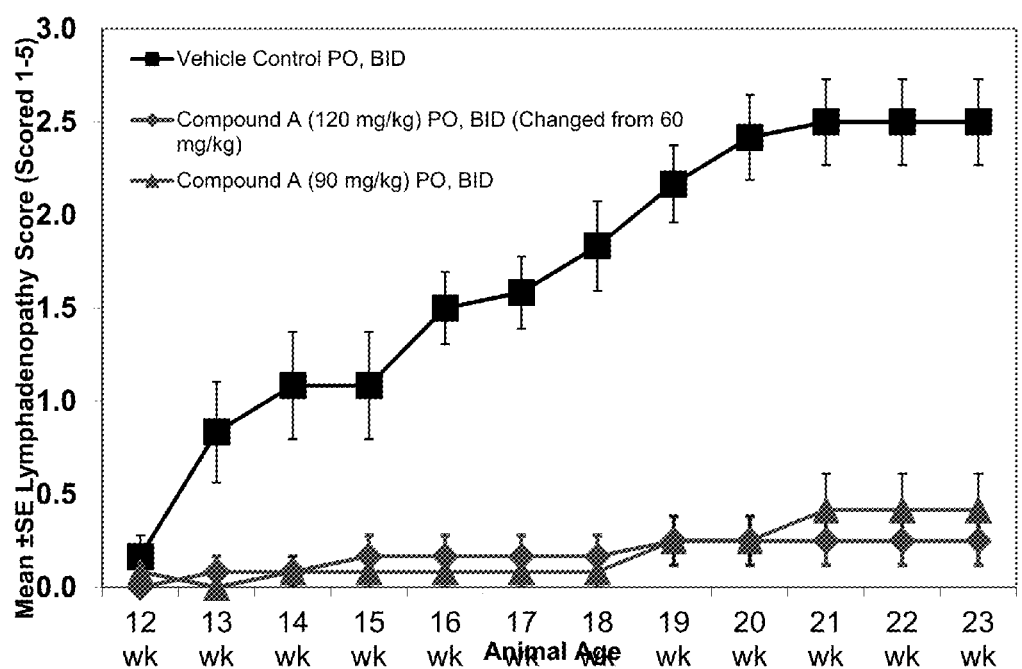
FIG. 2 illustrates efficacy of compound A in reducing lymphadenopathy in a MRL/lpr lupus model.
Figure 3:
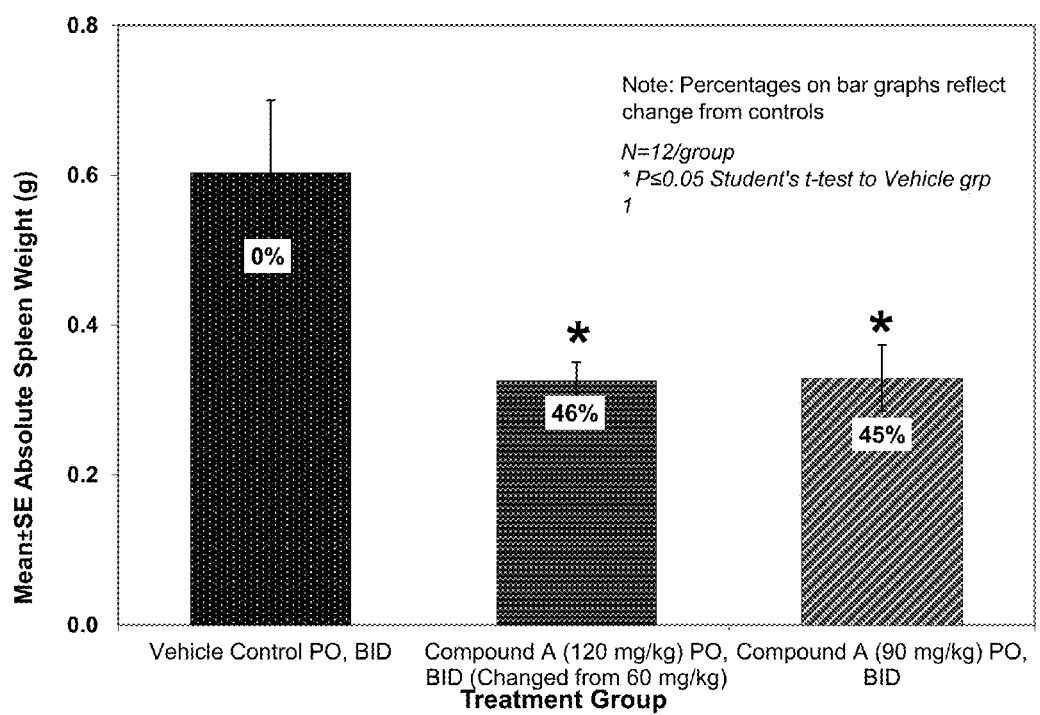
FIG. 3 illustrates efficacy of compound A in reducing splenomegaly in a MRL/lpr lupus model.
Figure 4:
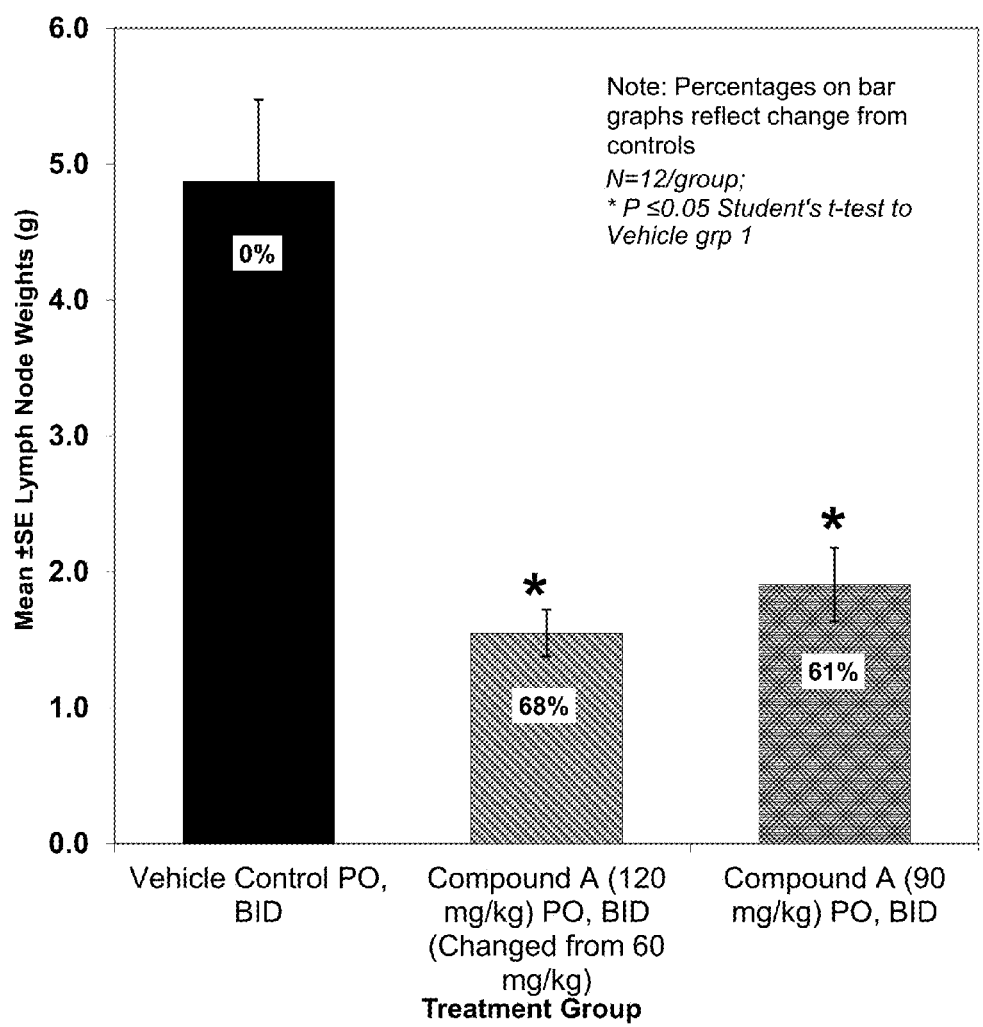
FIG. 4 illustrates efficacy of compound A in treatment of increased spleen weight.

Compound A demonstrated good efficacy in the model in multiple rounds of efficacy measurements. Both doses demonstrating a significant reduction in protein in the urine (FIG. 1), a reduction in lymphadenopathy score (FIG. 2), in mean absolute spleen weight (FIG. 3) and in mean lymph node weight (FIG. 4).

Clinical chemistry values from the animals showed a dose-dependent reduction in blood urea nitrogen (BUN) values, suggesting that kidney damage was lessened by treatment. The data in Table 2 illustrates that the reduction in BUN is statistically significant at the higher dose. In the two treatments groups, 21/23 (91%) of the animals were found to have a BUN≤33 mg/dL (in the normal range of BUN values for the mouse) versus only 2/11 (18%) in the control, untreated group.

TABLE 2

Key Clinical Chemistry Values

| Treatment (p.o. BID) | BUN (mg/dL) | BUN p value | Creatinine | BUN/ Creatinine | BUN/ Creatinine p value |
|---|---|---|---|---|---|
| Vehicle | 71.7 | — | 0.24 | 270.9 | — |
| Compound A, 90 mg/kg | 52.4 | 0.5 | 0.26 | 163.9 | .05 |
| Compound A, 120 mg/kg | 29.5 | 0.04 | 0.20 | 147.7 | .03 |

In conclusion, compound A in the MRL/lpr mouse model of SLE demonstrated a significant reduction in multiple measures of efficacy including protein in the urine, lymphadenopathy score, spleen weight and lymph node weight.

Example 2: Testing in Experimental Autoimmune Encephalitis

Figure 5:
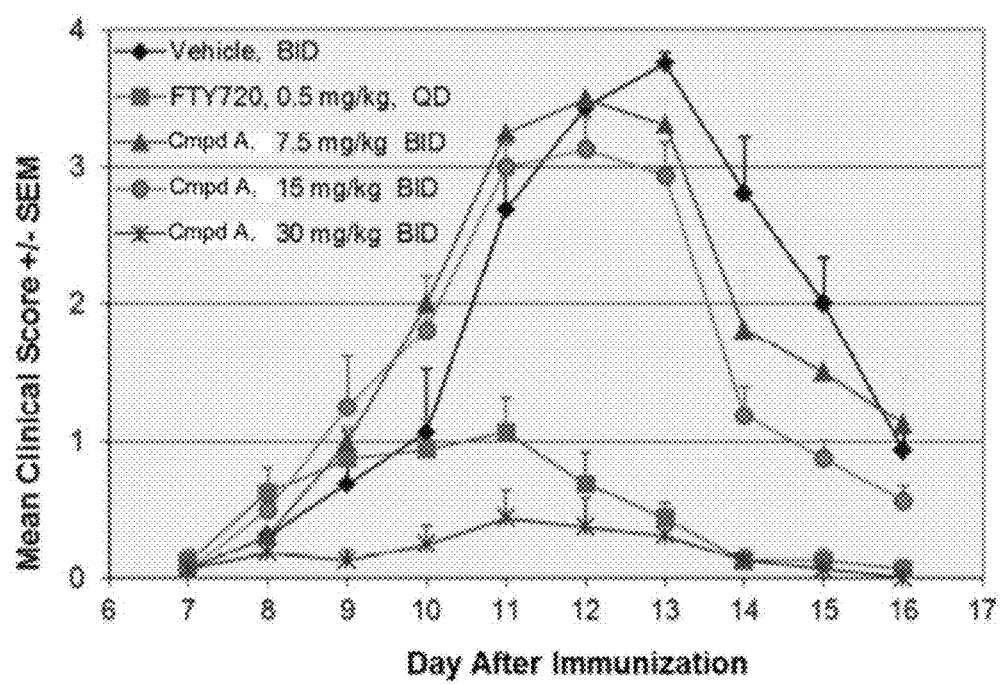
FIG. 5 illustrates efficacy of compound A in a rat model of encephalitis.

Compound A was tested in the experimental autoimmune encephalitis (EAE) model in Lewis rats. EAE was induced by MBP69-88/CFA immunization and pertussis toxin injection in Lewis rats (Hashim, et al., 1986, J Neurosci Res.; 16(3):467-78). Compound A was prepared as an oral suspension and dosed orally, twice per day (BID) at three doses, 7.5 and 15 and 30 mg/kg for total daily doses of 15, 30 and 60 mg/kg. The efficacy was compared to animals that received the positive control FTY720 (also known as fingolimod; a compound approved for use in humans) dosed once per day at a dose of 0.5 mg/kg. The treatment started on Day 8, when 48% of the rats had signs of EAE. Compound A showed excellent efficacy and a clear dose response. At 15 and 30 mg/kg BID, it significantly reduced maximum EAE severity as well as end severity compared to the vehicle control group, see FIG. 5. At the highest dose (30 mg/kg BID) it significantly reduced EAE incidence (Table 3). These results demonstrate that Compound A was efficacious at reducing EAE severity in the study in a dose-dependent manner.

TABLE 3

| Group | Treatment (p.o., all groups) | EAE incidence (%) | Median day of onset (all rats) | Mean day of onset +/− SEM (sick rats) |
|---|---|---|---|---|
| 1 | Vehicle, BID | 100.0% | 9.0 | 9.3 +/− 0.6 |
| 2 | FTY720, 0.5 mg/kg, QD | 87.5% | 8.0 | 8.0 +/− 0.3 |
| 3 | Compound A, 7.5 mg/kg, BID | 100.0% | 9.0 | 9.0 +/− 0.5 |
| 4 | Compound A, 15 mg/kg, BID | 100.0% | 8.0 | 8.5 +/− 0.4 |
| 5 | Compound A, 30 mg/kg, BID | 50.0%* | 13.5 | 9.0 +/− 0.9 |

*p < 0.05 vs. vehicle

In conclusion, compound A in the experimental autoimmune encephalitis model demonstrated a dose-dependent decrease in clinical score and at the highest dose employed, appeared superior to fingolimod, a compound approved for use in humans.

Example 3: Testing in Model of Uveitis

Figure 6:
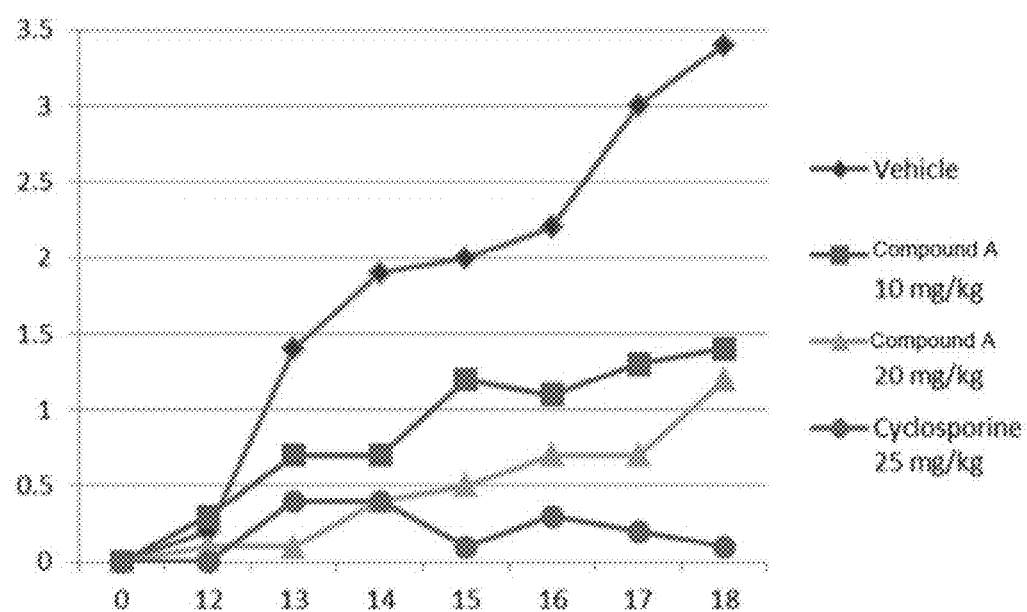
FIG. 6 illustrates clinical scores after administration of compound A in a rat uveitis model.
Figure 7:
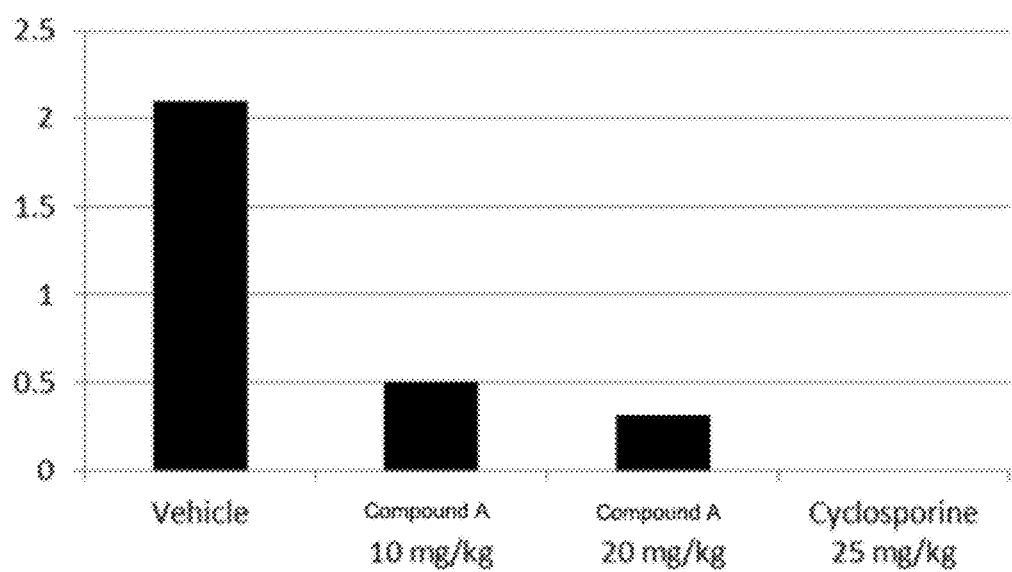
FIG. 7 illustrates histological scores of compound A in a rat uveitis model.

The animal model used in this testing was the Lewis rat model of experimental autoimmune uveitis, a well-known model of uveitis (Nussenblatt R B, et al, 1981, J Clin Invest. 67(4): 1228-1231; Mochizuki M, et al, 1985, Invest Ophthalmol Vis Sci. 26(2): 226-232). Compound A was prepared as an oral suspension and dosed orally, once per day at two doses, 10 and 20 mg/kg. The efficacy was compared to animals that received the positive control cyclosporine dosed at 25 mg/kg. This dose of cyclosporine was designed to inhibit the model by 95-100% and is equivalent to an exposure that is not tolerated in humans. Efficacy in the model was assessed by clinical grading and by assessment of the sections of the eyes prepared for histology at the completion of the experiment. Compound A was effective in this model showing a dose dependent decrease in disease severity as assessed by both clinical score (FIG. 6), and histopathological score (FIG. 7)

In conclusion, compound A in an experimental autoimmune model of uveitis elicited a greater than 50% reduction in clinical scores and a greater than 75% reduction in histopathological scores at very modest doses.

Example 4a: Evaluate the Efficacy and Safety of Compound A Compared to Placebo in Subjects with Chronic, Moderately-to-Severely Active Systemic Lupus Erythematosus (SLE)

Study design: Allocation: randomized
Endpoint Classification: Safety/Efficacy Study
Intervention Model: Parallel Assignment
Masking: Double Blind (Subject, Caregiver, Investigator, Outcomes Assessor)
Primary Purpose: Treatment
Primary Outcome Measures:
Achievement of response in a systemic lupus erythematosus (SLE) responder index [Time Frame: Day 169 (or 6 months)] [Designated as safety issue: No]
Number and percentage of participants achieving a response in an SLE responder index at Day 169 (or 6 months)
Secondary Outcome Measures:
Achievement of response in a systemic lupus erythematosus (SLE) responder index [Time Frame: Day 365 (or 1 year)] [Designated as safety issue: No]
Number and percentage of participants achieving a response in an SLE responder index at Day 365 (or 1 year)

| Arms | Assigned Interventions |
|---|---|
| Experimental: Compound A Low-dose Group Compound A will be given at the predetermined dosing intervals as specified in the protocol | Low dose of Compound A administered at the predetermined intervals |
| Experimental: Compound A High-dose Group Compound A will be given at the predetermined dosing intervals as specified in the protocol | High dose of Compound A administered at predetermined intervals |
| Placebo Comparator: Matching Placebo Group Placebo matching Compound A will be given at the predetermined dosing intervals as specified in the protocol | Other: Placebo Matching placebo to Compound A administered at predetermined intervals |

Eligibility
Ages Eligible for Study: 18 Years to 75 Years
Gender Eligible for Study: Both
Accepts Healthy Volunteers: No
Inclusion Criteria:
Fulfills at least 4 of the 11 American College of Rheumatology (ACR) criteria for systemic lupus erythematosus (SLE) including a positive antinuclear antibody (ANA) greater than or equal to 1:80 or elevated anti-double-stranded DNA or anti-Smith antibody at screening
Pediatric or adult SLE with chronic disease activity for greater than or equal to 24 weeks
Weight greater than or equal to 40 kg
Active moderate to severe SLE disease based on SLE disease activity score (SLEDAI) and British Isles Lupus Assessment Group Index (BILAG) and Physicians Global Assessment
No evidence of cervical malignancy on Pap smear within 2 years of randomization
Female subjects must be willing to avoid pregnancy
Negative tuberculosis (TB) test or newly positive TB test due to latent TB for which treatment must be initiated at or before randomization
Exclusion Criteria:
Active severe SLE-driven renal disease or unstable renal disease prior to screening
Active severe or unstable neuropsychiatric SLE
Clinically significant active infection including ongoing and chronic infections
History of human immunodeficiency virus (HIV)
Confirmed Positive tests for hepatitis B or positive test for hepatitis C
History of severe herpes infection such as herpes encephalitis, ophthalmic herpes, disseminated herpes
Live or attenuated vaccine within 4 weeks prior to screening
Subjects with significant hematologic abnormalities

Example 4b: Evaluate the Efficacy and Safety of Compound A in Subjects with Uveitis Study design: Allocation: randomized
Endpoint Classification: Safety/Efficacy Study
Intervention Model: Parallel Assignment
Masking: Double Blind (Subject, Caregiver, Investigator, Outcomes Assessor)
Primary Purpose: Treatment
Primary Outcome Measures:
Control of intraocular inflammation [Time Frame: at 6-month visit][Designated as safety issue: No]
Absence of intraocular inflammation (e.g. less than trace AC cells; no vitreous haze; inactive chorioretinal lesions).
Evaluation of Adverse Events [Time Frame: Baseline to Final Visit (Final Visit could occur at any point up to 282 weeks)] [Designated as safety issue: Yes]
Significant laboratory value changes [Time Frame: Baseline to Final Visit (Final Visit could occur at any point up to 282 weeks)] [Designated as safety issue: Yes]
Significant vital sign changes [Time Frame: Baseline to Final Visit (Final Visit could occur at any point up to 282 weeks)] [Designated as safety issue: Yes]
Secondary Outcome Measures:
Control of intraocular inflammation [Time Frame: 12-month clinical visit][Designated as safety issue: No]
Proportion of subjects at each study time point with no new active, inflammatory chorioretinal or inflammatory retinal vascular lesion in both eyes relative to Baseline for subjects who had inactive uveitis when they entered the study. [Time Frame: Final Visit (Final Visit could occur at any point up to 282 weeks)] [Designated as safety issue: No]

Proportion of subjects at each study time point with no new active, inflammatory chorioretinal or inflammatory retinal vascular lesion in both eyes relative to Week 8 for subjects who had active uveitis when they entered the study. [Time Frame: Final Visit (Final Visit could occur at any point up to 282 weeks)] [Designated as safety issue: No]

Proportion of subjects at each study time point with a Grade <=0.5+ in AC cells in both eyes on Slit Lamp Exam according to SUN criteria. [Time Frame: Final Visit (Final Visit could occur at any point up to 282 weeks)] [Designated as safety issue: No]

Proportion of subjects at each study time point with a Grade <=0.5+ in vitreous haze in both eyes on indirect ophthalmoscopy according to NEI/SUN criteria. [Time Frame: Final Visit (Final Visit could occur at any point up to 282 weeks)] [Designated as safety issue: No]

Proportion of subjects at each study time point without a worsening of BCVA by >=15 letters on the ETDRS in both eyes relative to Baseline for subjects who had inactive uveitis when they entered the study. [Time Frame: Final Visit (Final Visit could occur at any point up to 282 weeks)] [Designated as safety issue: No]

Proportion of subjects at each study time point without a worsening of BCVA by >=15 letters on the ETDRS in both eyes relative to Week 8 for subjects who had active uveitis when they entered the study. [Time Frame: Final Visit (Final Visit could occur at any point up to 282 weeks)] [Designated as safety issue: No]

Percent change in central retinal thickness (1 mm subfield) in each eye at each study time point relative to Baseline for subjects who had inactive uveitis when they entered the study. [Time Frame: Baseline to Final Visit (Final Visit could occur at any point up to 282 weeks)][Designated as safety issue: No]

Percent change in central retinal thickness (1 mm subfield) in each eye at each study time point relative to Week 8 for subjects who had active uveitis when they entered the study. [Time Frame: Week 8 to Final Visit (Final Visit could occur at any point up to 282 weeks)][Designated as safety issue: No]

Change in NEI Visual Functioning Questionnaire (VFQ-25) score at each study time point relative to Baseline for subjects who had inactive uveitis when they entered the study. [Time Frame: Baseline to Final Visit (Final Visit could occur at any point up to 282 weeks)][Designated as safety issue: No]

Change in NEI Visual Functioning Questionnaire (VFQ-25) score at each study time point relative to week 8 for subjects who had active uveitis when they entered the study. [Time Frame: Week 8 to Final Visit (Final Visit could occur at any point up to 282 weeks)][Designated as safety issue: No]

Proportion of subjects at each study time point achieving a >=50% reduction in immunosuppression load relative to Baseline for subjects who had inactive uveitis when they entered the study. [Time Frame: Final Visit (Final Visit could occur at any point up to 282 weeks)] [Designated as safety issue: No]

Proportion of subjects at each study time point achieving a >=50% reduction in immunosuppression load relative to Week 8 for subjects who had active uveitis when they entered the study. [Time Frame: Final Visit (Final Visit could occur at any point up to 282 weeks)] [Designated as safety issue: No]

Other Outcome Measures:

Elevation of IOP [Time Frame: At 3-month, 6-month, and 12-month visit][Designated as safety issue: Yes]

Ocular hypertension and IOP>30 and 10 mm Hg increase or greater in IOP will be assessed.

Progression of cataract or need for cataract surgery [Time Frame: At 3-month, 6 month, and 12-month visit] [Designated as safety issue: Yes]

| Arms | Assigned Interventions |
|---|---|
| Experimental: Compound A Low-dose Group Compound A will be given at the predetermined dosing intervals as specified in the protocol | Low dose of Compound A administered at the predetermined intervals |
| Experimental: Compound A High-dose Group Compound A will be given at the predetermined dosing intervals as specified in the protocol | High dose of Compound A administered at predetermined intervals |
| Placebo Comparator: Matching Placebo Group Placebo matching Compound A will be given at the predetermined dosing intervals as specified in the protocol | Other: Placebo Matching placebo to Compound A administered at predetermined intervals |

DETAILED DESCRIPTION

Background:

Intermediate and posterior uveitis are thought to be severe intraocular inflammation that may lead to permanent visual loss. It is estimated that these forms of uveitis comprise the fifth or sixth leading cause of blindness and tend to affect working class age patients, thus causing loss of work hours and diminished productivity and quality of life. Because the posterior segment of the eye is not adequately treated by corticosteroid drops often systemic drug therapy is used including oral corticosteroids or prednisone. Prednisone can have a myriad of side effects in approximately one-quarter to one-third of cases treated in tertiary care centers such as ours, additional medications such as immunosuppressive drugs are required to control the disease and/or to allow for appropriate tapering of oral prednisone to subsequent levels that have a low side effect profile when delivered over a long period of time. Typically, chronic prednisone therapy in doses of 7.5 mg daily or less are thought to have a low enough side effect profile to be amenable to long-term therapy. However frequently immunosuppressive drugs are required to get the dosing to this level. There are occasions when patients are intolerant of any dose of oral corticosteroids or are intolerant of the higher doses of oral corticosteroids (30-60 mg daily) and therefore this treatment modality is avoided due to prednisone's attendant side effects. Although periocular and intravitreal corticosteroids injections may be performed, with these modalities the standard of care is to wait until the disease reactivates before instituting such therapy and therefore a chronic suppressive dose is not obtained. The fluocinolone acetonide implant (Retisert®, Bausch and Lomb, Tampa, Fla.) is FDA-approved for the treatment of intermediate and posterior uveitis and it is equally effective in controlling uveitis as high-dose oral corticosteroids but avoids the systemic side effects associated with the use of high doses of oral corticosteroids. However, this form of local therapy has high rates of ocular side effects, including ocular hypertension causing glaucoma and/or requiring glaucoma surgery and cataracts. Furthermore, every two and half to three years the implant is exhausted of corticosteroid and therefore repeat surgical insertion of another implant may be required.

Eligibility

Ages Eligible for Study: 18 Years and older

Gender Eligible for Study: Both

Accepts Healthy Volunteers: No

Inclusion Criteria:
  Active sight-threatening intermediate or posterior uveitis.
  Patients must be age 18 years or older and sign an informed consent.
  The ocular media must be clear enough to obtain OCT and fundus photographs.
  No elective intraocular surgery should be planned for the first 3 months after enrollment.

Exclusion Criteria:
  Infectious uveitis
  History of scleritis
  Active or suspected viral infection of the cornea or conjunctiva
  History of mycobacterial or fungal disease
  HIV positivity
  Age <18 years old
  Uncontrolled IOP
  Advanced glaucoma
  Aphakia with rupture of the posterior lens capsule
  ACIOL with rupture of the posterior lens capsule
  Media opacity that would preclude evaluation of the posterior pole via fundus photography or OCT assessment
  Planned elective ocular surgery within 3 months of enrollment

Example 4c: Evaluate the Efficacy and Safety of Compound A in Subjects with Autoimmune Encephalitis Study design: Allocation: randomized Endpoint Classification: Safety/Efficacy Study Intervention Model: Parallel Assignment Masking: Double Blind (Subject, Caregiver, Investigator, Outcomes Assessor)

Primary Purpose: Treatment

Primary Outcome Measures:

To assess the safety and tolerability of Compound A in the treatment of Autoimmune Encephalitis. [Time Frame: 12 months] [Designated as safety issue: Yes]

The natural history of Autoimmune Encephalitis is a progressive deterioration in cortical function; therefore, any evidence of stabilization or improvement in measures of motor function, cognition and/or seizure frequency will be evidence of efficacy and will be assessed at [Time Frame: 12 months] [Designated as safety issue: No]

Secondary Outcome Measures:

The percentage of patients with a 50% reduction in seizure frequency (responder rate) at 6 months post treatment (as compared to the patient's baseline seizure frequency) will be determined. [Time Frame: 12 months] [Designated as safety issue: No]

| Arms | Assigned Interventions |
|---|---|
| Experimental: Compound A Low-dose Group Compound A will be given at the predetermined dosing intervals as specified in the protocol | Low dose of Compound A administered at the predetermined intervals |
| Experimental: Compound A High-dose Group Compound A will be given at the predetermined dosing intervals as specified in the protocol | High dose of Compound A administered at predetermined intervals |
| Placebo Comparator: Matching Placebo Group Placebo matching Compound A will be given at the predetermined dosing intervals as specified in the protocol | Other: Placebo Matching placebo to Compound A at predetermined intervals |

Eligibility

Ages Eligible for Study: 18 Years and older

Gender Eligible for Study: Both

Accepts Healthy Volunteers: No

Inclusion Criteria:
  Encephalopathy symptoms (change of mental state and consciousness level) persist for more than 24 hours;
  At least one or more clinical features of the followings: fever, epilepsy, focal neurological deficiency symptoms, changes in CSF (cerebrospinal fluid inflammatory), changes in EEG (electroencephalogram), radiographic abnormalities;
  Clinical suspected encephalitis, but conventional detected methods cannot make etiology clear Exclusion Criteria:

The metabolic encephalopathy;

Infectious encephalitis with clinically clear pathogen, referring the specific pathogenic microorganisms, including: bacteria, virus, fungus, parasite, spirochete and so on;

Non-infectious encephalitis with clinically clear diagnosis, including: multiple sclerosis, optic neuromyelitis, acute disseminated encephalomyelitis and so on.

The examples and embodiments described herein are for illustrative purposes only and various modifications or changes suggested to persons skilled in the art are to be included within the spirit and purview of this application and scope of the appended claims.

What is claimed is:

1. A method of treating encephalitis in a subject in need thereof comprising administering to the subject a composition comprising a compound, or a pharmaceutically acceptable salt thereof, selected from the group consisting of:

$N^4$-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-N2-ethyl-5-fluoropyrimidine-2,4-diamine, $N^4$-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-5-fluoro-$N^2$,$N^2$-dimethylpyrimidine-2,4-diamine, $N^2$-cyclopropyl-N4-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-5-fluoropyrimidine-2,4-diamine, $N^4$-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-5-fluoro-$N^2$-methylpyrimidine-2,4-diamine, N⁴-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-5-fluoro-N²-isopropylpyrimidine-2,4-diamine, N⁴-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-N²-ethylpyrimidine-2,4-diamine, N⁴-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-N²,N²-dimethylpyrimidine-2,4-diamine, 5-{[(8S)-6,8-dimethyl-6,9-diazaspiro[4.5]dec-9-yl]carbonyl)}-N-(5-fluoro-2-methylpyrimidin-4-yl)-6,6-dimethyl-1,4,5,6-tetrahydropyrrolo[3,4-c]pyrazol-3-amine, N⁴-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-N²-ethyl-5-fluoropyrimidine-2,4-diamine, N⁴-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)-N²-ethyl-5-fluoropyrimidine-2,4-diamine, N²-ethyl-5-fluoro-N⁴-(5-{[(2S,5R)-4-(3-methoxypropyl)-2,5-dimethylpiperazin-1-yl]carbonyl})-6,6-dimethyl-1,4,5,6-tetrahydropyrrolo[3,4-c]pyrazol-3-yl)pyrimidine-2,4-diamine, N⁴-(6,6-dimethyl-5-{[(2S,5R)-2,4,5-trimethylpiperazin-1-yl]carbonyl}-1,4,5,6-tetrahydropyrrolo[3,4-c]pyrazol-3-yl)-N²-ethyl-5-fluoropyrimidine-2,4-diamine, 4-[(6,6-dimethyl-5-{[(2S,5R)-2,4,5-trimethylpiperazin-1-yl]carbonyl}-1,4,5,6-tetrahydropyrrolo[3,4-c]pyrazol-3-yl)amino]pyrimidine-2-carbonitrile, N-(2-ethyl-5-fluoropyrimidin-4-yl)-6,6-dimethyl-5-{[(2S)-2,4,5,5-tetramethylpiperazin-1-yl]carbonyl})-1,4,5,6-tetrahydropyrrolo[3,4-c]pyrazol-3-amine, N-(2-ethyl-5-fluoropyrimidin-4-yl)-5-{[(2S,5R)-4-(3-methoxypropyl)-2,5-dimethylpiperazin-1-yl]carbonyl}-6,6-dimethyl-1,4,5,6-tetrahydropyrrolo[3,4-c]pyrazol-3-amine, 2-((5S)-4-{[3-[(2-ethyl-5-fluoropyrimidin-4-yl)amino]-6,6-dimethyl-4,6-dihydropyrrolo[3,4-c]pyrazol-5(1H)-yl]carbonyl}-1,5-dimethylpiperazin-2-yl)ethanol, 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, N-(5-fluoro-2-methylpyrimidin-4-yl)-6,6-dimethyl-5-{[(2S)-2,4,5,5-tetramethylpiperazin-1-yl]carbonyl})-1,4,5,6-tetrahydropyrrolo[3,4-c]pyrazol-3-amine, N-(5-fluoro-2-propylpyrimidin-4-yl)-6,6-dimethyl-5-{[(2S)-2,4,5,5-tetramethylpiperazin-1-yl]carbonyl})-1,4,5,6-tetrahydropyrrolo[3,4-c]pyrazol-3-amine, N-(5-fluoro-2-isopropylpyrimidin-4-yl)-6,6-dimethyl-5-{[(2S)-2,4,5,5-tetramethylpiperazin-1-yl]carbonyl})-1,4,5,6-tetrahydropyrrolo[3,4-c]pyrazol-3-amine, N-[5-fluoro-2-(methoxymethyl)pyrimidin-4-yl]-6,6-dimethyl-5-{[(2S)-2,4,5,5-tetramethylpiperazin-1-yl]carbonyl})-1,4,5,6-tetrahydropyrrolo[3,4-c]pyrazol-3-amine, 5-{[(2S,5R)-2,5-dimethyl-4-(tetrahydro-2H-pyran-4-ylmethyl)piperazin-1-yl]carbonyl}-N-(2-ethyl-5-fluoropyrimidin-4-yl)-6,6-dimethyl-1,4,5,6-tetrahydropyrrolo[3,4-c]pyrazol-3-amine, 5-{[(2S,5R)-2,5-dimethyl-4-(tetrahydro-2H-pyran-4-yl)piperazin-1-yl]carbonyl)}-N-(4-methoxypyrimidin-2-yl)-6,6-dimethyl-1,4,5,6-tetrahydropyrrolo[3,4-c]pyrazol-3-amine, 5-{[(2S,5R)-2,5-dimethyl-4-(tetrahydro-2H-pyran-4-yl)piperazin-1-yl]carbonyl}-6,6-dimethyl-N-(4-methylpyrimidin-2-yl)-1,4,5,6-tetrahydropyrrolo[3,4-c]pyrazol-3-amine, 5-{[(2S,5R)-2,5-dimethyl-4-(tetrahydro-2H-pyran-4-yl)piperazin-1-yl]carbonyl}-6,6-dimethyl-N-4-(trifluoromethyl)pyrimidin-2-yl)-1,4,5,6-tetrahydropyrrolo[3,4-c]pyrazol-3-amine, 5-{[(2S,5R)-2,5-dimethyl-4-(tetrahydro-2H-pyran-4-ylmethyl)piperazin-1-yl]carbonyl}-6,6-dimethyl-N-(4-methylpyrimidin-2-yl)-1,4,5,6-tetrahydropyrrolo[3,4-c]pyrazol-3-amine, N-(2-ethoxy-5-fluoropyrimidin-4-yl)-6,6-dimethyl-5-{[(2S,5R)-2,4,5-trimethylpiperazin-1-yl]carbonyl})-1,4,5,6-tetrahydropyrrolo[3,4-c]pyrazol-3-amine, N-(2-ethoxy-5-fluoropyrimidin-4-yl)-6,6-dimethyl-5-{[4-ethyl(2S,5R)-2,5-dimethylpiperazin-1-yl]carbonyl})-1,4,5,6-tetrahydropyrrolo[3,4-c]pyrazol-3-amine, N-(2-ethoxy-5-fluoropyrimidin-4-yl)-6,6-dimethyl-5-{[(2S)-2,4,5,5-tetramethylpiperazin-1-yl]carbonyl})-1,4,5,6-tetrahydropyrrolo[3,4-c]pyrazol-3-amine, N-(2-ethoxy-5-fluoropyrimidin-4-yl)-5-{[(2S,5R)-4-(2-methoxyethyl)-2,5-dimethylpiperazin-1-yl]carbonyl}-6,6-dimethyl-1,4,5,6-tetrahydropyrrolo[3,4-c]pyrazol-3-amine, N-(2-ethoxy-5-fluoropyrimidin-4-yl)-5-{[(2S,5R)-4-(3-methoxypropyl)-2,5-dimethylpiperazin-1-yl]carbonyl}-6,6-dimethyl-1,4,5,6-tetrahydropyrrolo[3,4-c]pyrazol-3-amine, N-[5-fluoro-2-(2,2,2-trifluoroethoxy)pyrimidin-4-yl]-5-{[(2S,5R)-4-(3-methoxypropyl)-2,5-dimethylpiperazin-1-yl]carbonyl}-6,6-dimethyl-1,4,5,6-tetrahydropyrrolo[3,4-c]pyrazol-3-amine, N-[5-fluoro-2-(2,2,2-trifluoroethoxy)pyrimidin-4-yl]-6,6-dimethyl-5-{[(2S,5R)-2,4,5-trimethylpiperazin-1-yl]carbonyl}-1,4,5,6-tetrahydropyrrolo[3,4-c]pyrazol-3-amine, N-[5-fluoro-2-(2,2,2-trifluoroethoxy)pyrimidin-4-yl]-6,6-dimethyl-5-{[(2S)-2,4,5,5-tetramethylpiperazin-1-yl]carbonyl})-1,4,5,6-tetrahydropyrrolo[3,4-c]pyrazol-3-amine, 5-{[(2S,5R)-2,5-dimethyl-4-(tetrahydro-2H-pyran-4-ylmethyl)piperazin-1-yl]carbonyl}-N-(2-ethoxy-5-fluoropyrimidin-4-yl)-6,6-dimethyl-1,4,5,6-tetrahydropyrrolo[3,4-c]pyrazol-3-amine, 5-{[(2S,5R)-2,5-dimethyl-4-(tetrahydro-2H-pyran-4-yl)piperazin-1-yl]carbonyl}-N-(2-ethoxy-5-fluoropyrimidin-4-yl)-6,6-dimethyl-1,4,5,6-tetrahydropyrrolo[3,4-c]pyrazol-3-amine, 2-((5S)-4-{[3-[(2-ethoxy-5-fluoropyrimidin-4-yl)amino]-6,6-dimethyl-4,6-dihydropyrrolo[3,4-c]pyrazol-5(1H)-yl]carbonyl}-1,5-dimethylpiperazin-2-yl)ethanol, 2-((5S)-4-{[3-[(2-ethoxy-5-fluoropyrimidin-4-yl)amino]-6,6-dimethyl-4,6-dihydropyrrolo[3,4-c]pyrazol-5(1H)-yl]carbonyl}-1,5-dimethylpiperazin-2-yl)ethanol, 5-[(4-fluoro-1-methylpiperidin-4-yl)carbonyl]-N-[5-fluoro-2-(2,2,2-trifluoroethoxy)pyrimidin-4-yl]-6,6-dimethyl-1,4,5,6-tetrahydropyrrolo[3,4-c]pyrazol-3-amine, 5-{[(2S,5R)-2,5-dimethyl-4-(tetrahydro-2H-pyran-4-ylmethyl)piperazin-1-yl]carbonyl}-N-[5-fluoro-2-(methoxymethyl)pyrimidin-4-yl]-6,6-dimethyl-1,4,5,6-tetrahydropyrrolo[3,4-c]pyrazol-3-amine, and 2-((5S)-4-{[3-{[5-fluoro-2-(methoxymethyl)pyrimidin-4-yl]amino}-6,6-dimethyl-4,6-dihydropyrrolo[3,4-c]pyrazol-5(1H)-yl]carbonyl}-1,5-dimethylpiperazin-2-yl)ethanol.

2. The method of claim 1, wherein the compound is $N^4$-(5-{[(2S,5R)-2,5-dimethyl-4-(tetrahydro-2H-pyran-4-ylmethyl)piperazin-1-yl]carbonyl}-6,6-dimethyl-1,4,5,6-tetrahydropyrrolo[3,4-c]pyrazol-3-yl)-$N^2$-ethyl-5-fluoropyrimidine-2,4-diamine, or a pharmaceutically acceptable salt thereof.

3. The method of claim 1, wherein the compound is $N^4$-(5-{[(2S,5R)-2,5-dimethyl-4-(tetrahydro-2H-pyran-4-yl)piperazin-1-yl]carbonyl}-6,6-dimethyl-1,4,5,6-tetrahydropyrrolo[3,4-c]pyrazol-3-yl)-$N^2$-ethyl-5-fluoropyrimidine-2,4-diamine, or a pharmaceutically acceptable salt thereof.

4. The method of claim 1, wherein the compound is 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof.

5. The method of claim 1, wherein the compound is 5-{[(2S,5R)-2,5-dimethyl-4-(tetrahydro-2H-pyran-4-ylmethyl)piperazin-1-yl]carbonyl}-N-(2-ethyl-5-fluoropyrimidin-4-yl)-6,6-dimethyl-1,4,5,6-tetrahydropyrrolo[3,4-c]pyrazol-3-amine, or a pharmaceutically acceptable salt thereof.

6. The method of claim 1, wherein the compound is 5-{[(2S,5R)-2,5-dimethyl-4-(tetrahydro-2H-pyran-4-yl)piperazin-1-yl]carbonyl}-N-(4-methoxypyrimidin-2-yl)-6,6-dimethyl-1,4,5,6-tetrahydropyrrolo[3,4-c]pyrazol-3-amine, or a pharmaceutically acceptable salt thereof.

7. The method of claim 1, wherein the compound is 5-{[(2S,5R)-2,5-dimethyl-4-(tetrahydro-2H-pyran-4-yl)piperazin-1-yl]carbonyl}-6,6-dimethyl-N-[4-(trifluoromethyl)pyrimidin-2-yl]-1,4,5,6-tetrahydropyrrolo[3,4-c]pyrazol-3-amine, or a pharmaceutically acceptable salt thereof.

8. The method of claim 1, wherein the compound is 5-{[(2S,5R)-2,5-dimethyl-4-(tetrahydro-2H-pyran-4-yl)piperazin-1-yl]carbonyl}-N-(2-ethoxy-5-fluoropyrimidin-4-yl)-6,6-dimethyl-1,4,5,6-tetrahydropyrrolo[3,4-c]pyrazol-3-amine, or a pharmaceutically acceptable salt thereof.

9. The method of claim 1, wherein the compound is $N^4$-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-N2-ethyl-5-fluoropyrimidine-2,4-diamine, or a pharmaceutically acceptable salt thereof.

10. The method of claim 1, wherein the compound is $N^4$-(6,6-dimethyl-5-{[(2S)-2,4,5,5-tetramethylpiperazin-1-yl]carbonyl}-1,4,5,6-tetrahydropyrrolo[3,4-c]pyrazol-3-yl)-$N^2$-ethylpyrimidine-2,4-diamine, or a pharmaceutically acceptable salt thereof.

11. The method of any one of claims 1-10, wherein the encephalitis is autoimmune encephalitis, acute disseminated encephalitis, acute demyelinating encephalitis, NMDA receptor associated encephalitis, voltage-gated potassium channel-complex antibody derived encephalitis, hashimoto's encephalitis, or Rasmussen encephalitis.

12. A method of treating encephalitis in a subject in need thereof comprising administering to the subject a composition comprising a compound having the formula 5-{[(2S,5R)-2,5-dimethyl-4-(tetrahydro-2H-pyran-4-ylmethyl)piperazin-1-yl]carbonyl}-N-(5-fluoro-2-methylpyrimidin-4-yl)-6,6-dimethyl-1,4,5,6-tetrahydropyrrolo[3,4-c]pyrazol-3-amine, or a pharmaceutically acceptable salt thereof, and a pharmaceutically acceptable excipient.

13. The method of claim 12, wherein the encephalitis is autoimmune encephalitis, acute disseminated encephalitis, acute demyelinating encephalitis, NMDA receptor associated encephalitis, voltage-gated potassium channel-complex antibody derived encephalitis, hashimoto's encephalitis, or Rasmussen encephalitis.

* * * * *